(12) United States Patent
Zurawski

(10) Patent No.: US 10,064,858 B2
(45) Date of Patent: Sep. 4, 2018

(54) METHODS AND COMPOSITIONS FOR TREATING BACTERIAL INFECTIONS WITH IRON CHELATORS

(75) Inventor: Daniel Zurawski, Germantown, MD (US)

(73) Assignee: THE UNITED STATES OF AMERICA, AS REPRESENTED BY THE SECRETARY OF THE ARMY, Washington, DC (US)

( * ) Notice: Subject to any disclaimer, the term of this patent is extended or adjusted under 35 U.S.C. 154(b) by 0 days.

(21) Appl. No.: 13/982,432

(22) PCT Filed: Jan. 31, 2012

(86) PCT No.: PCT/US2012/023377
§ 371 (c)(1),
(2), (4) Date: Jul. 29, 2013

(87) PCT Pub. No.: WO2012/106364
PCT Pub. Date: Aug. 9, 2012

(65) Prior Publication Data
US 2013/0310346 A1    Nov. 21, 2013

Related U.S. Application Data

(60) Provisional application No. 61/462,696, filed on Jan. 31, 2011.

(51) Int. Cl.
| | |
|---|---|
| *A61K 31/496* | (2006.01) |
| *A61K 38/16* | (2006.01) |
| *A61K 45/06* | (2006.01) |
| *A61K 31/16* | (2006.01) |
| *A61K 31/395* | (2006.01) |
| *A61K 31/4192* | (2006.01) |
| *A61K 31/4412* | (2006.01) |
| *A61K 31/44* | (2006.01) |
| *A61K 31/4422* | (2006.01) |
| *A61K 31/65* | (2006.01) |

(52) U.S. Cl.
CPC ............ *A61K 31/496* (2013.01); *A61K 31/16* (2013.01); *A61K 31/395* (2013.01); *A61K 31/4192* (2013.01); *A61K 31/44* (2013.01); *A61K 31/4412* (2013.01); *A61K 31/4422* (2013.01); *A61K 31/65* (2013.01); *A61K 38/16* (2013.01); *A61K 45/06* (2013.01); *Y02A 50/473* (2018.01)

(58) Field of Classification Search
CPC .................................................. A61K 31/496
USPC ........................................................ 514/514
See application file for complete search history.

(56) References Cited

U.S. PATENT DOCUMENTS

| | | |
|---|---|---|
| 5,198,419 A | 3/1993 | Ando et al. |
| 5,688,516 A | 11/1997 | Raad et al. |
| 6,855,711 B1 | 2/2005 | Warshawsky et al. |
| 8,058,442 B2 | 11/2011 | Youdim et al. |
| 2003/0134779 A1 | 7/2003 | Diarra et al. |
| 2004/0142037 A1 | 7/2004 | Engelmayer et al. |
| 2005/0043369 A1 | 2/2005 | Markham et al. |
| 2005/0049181 A1 | 3/2005 | Madhyastha |
| 2005/0143286 A1* | 6/2005 | Singh et al. ............... 514/2 |
| 2005/0175684 A1 | 8/2005 | Gwathmey |
| 2006/0234927 A1 | 10/2006 | Youdim et al. |
| 2007/0082904 A1* | 4/2007 | Tam ............... C07D 213/81 |
| | | 514/235.2 |
| 2007/0142292 A1* | 6/2007 | Varadhachary et al. ....... 514/12 |

OTHER PUBLICATIONS

Chan et al. Effects of Chelators (Deferoxamine, Deferiprone, and Deferasirox) on the Growth of Klebsiella Pneumoniae and Aeromonas Hydrophila Isolated From Transfusion Dependent Thalassemia Patients. Proceedings 17th ICOC (2009) vol. 33, p. 353-360).*
Zavascki et al. Multidrug-resistant *Pseudomonas aeruginosa* and *Acinetobacter baumannii*: resisstance mechanism and implications fortherapy. Expert Rev. Anti Infect Ther (2010), vol. 8, pp. 71-93.*
Van Asbeck B S et al. "Inhibition of bacterial multiplication by the iron chelator deferoxamine: potentiating effect of ascorbic acid", European Journal of Clinical Microbiology 1983, vol. 2, No. 5, Oct. 1983 (Oct. 1983), pp. 426-431, XP008169505, ISSN: 0722-2211.
Extended European Search Report dated Jun. 10, 2014 for EP 12742682.3.
Int'l Search Report and Written Opinion for PCT/US2012/23377 dated May 21, 2012.
Int'l Prelim. Report on Patentability for PCT/US2012/23377 dated Aug. 6, 2013.
Chaston et al. Iron Chelators for the Treatment of Iron Overload Disease: Relationship Between Structure, Redox Activity, and Toxicity. American Journal of Hematology, 2003, vol. 73, pp. 200-210; abstract; p. 202, col. 2, para 3; p. 203, Fig 1 Downloaded from: http://www.ncbLnlm.nih.gov/pubmed/12827659.
Moreau-Marquis et al. Tobramycin and FDA-Approved Iron Chelators Eliminate *Pseudomonas aeruginosa* Biofilms on Cystic Fibrosis Cells, Am. J. Respir Cell Mol. Biol. vol. 41. pp. 305-313, 2009.
O'May et al. Iron-binding Compounds Impair *Pseudomonas aeruginosa* Biofilm Formation, Especially Under Anaerobic Conditions, Jour. of Med. Microbiology (2009), 58, 765-773.
Reid et al., Iron Chelation Directed Against Biofilms as an Adjunct to Conventional Antibiotics, Am. J. Physiol. Lung Cell Mol. Physiol 296: L857-L858, 2009.

(Continued)

*Primary Examiner* — Melenie L McCormick
*Assistant Examiner* — Taina D Matos Negron
(74) *Attorney, Agent, or Firm* — McAndrews, Held & Malloy, Ltd.

(57) ABSTRACT

The present invention provides methods and compositions for treating or preventing bacterial infections, where a pharmaceutically acceptable iron chelator that reduces biological availability of iron for one or more strains of bacteria, such as VK28 or an analog or derivative thereof is administered to a patient in need of treatment. The method also provides methods and compositions where an iron chelator and an antibiotic are administered to a patient in need of treatment for a bacterial infection.

9 Claims, 49 Drawing Sheets

(56) References Cited

OTHER PUBLICATIONS

International Search Report and Written Opinion for International Patent Application No. PCT/US2012/23377, dated May 21, 2012.
Chaston et al., "Iron Chelators for the Treatment of Iron Overload Disease: Relationship Between Structure, Redox Activity, and Toxicity." American Journal of Hematology, vol. 73, pp. 200-210; abstract; p. 202, col. 2, para 3, Fig. 1, 2003.
Moreau-Marquis et al., "Tobramycin and FDA-Approved Iron Chelators Eliminate *Pseudomonas aeruginosa* Biofilms on Cystic Fibrosis Cells." American Journal of Respiratory Cell and Molecular Biology, vol. 41, pp. 305-313, 2009.
O'May et al., "Iron-binding compounds impair *Pseudomonas aeruginosa* biofilm formation, especially under anaerobic conditions." Journal of Medical Microbiology (2009), vol. 58, pp. 765-773.
Reid et al., "Iron chelation directed against biofilms as an adjunct to conventional antibiotics." American Journal of Physiology Lung and Molecular Physiology, 296, L857-L858, 2009.

\* cited by examiner

METHODS AND COMPOSITIONS FOR TREATING BACTERIAL INFECTIONS WITH IRON CHELATORS

CROSS-REFERENCE TO RELATED APPLICATION

This application is a 371 national stage application of PCT Application Serial No. PCT/US2012/023377 filed Jan. 31, 2012, entitled "Methods and Compositions for Treating Bacterial Infections with Iron Chelators" which claims the benefit of priority from U.S. Provisional Patent Application Ser. No. 61/462,696 entitled "VK28 and Derivatives Thereof, as Antibiotics, and Their Use With Conventional or Novel Antibiotics, and Compositions Thereof" filed on Jan. 31, 2011. Each application is incorporated by reference in their entireties.

RIGHTS IN THE INVENTION

The present invention was made with support from the United States Government and, specifically, the Walter Reed Army Institute of Research, and, accordingly, the United States government has certain rights in this invention.

TECHNICAL FIELD

The present technology is directed generally to methods for treating bacterial infections by administration of an iron chelator such as VK28, and to compositions comprising an iron chelator and an antibiotic.

BACKGROUND

All forms of life need iron, but in particular, bacteria cannot grow unless they have a source of iron to draw from in the environment. The human body and its immune system actually restrict iron levels to keep bacterial growth in check; however, some pathogenic bacteria have found a way around the immune system by secreting siderophores, small molecules that bind and sequester iron from the environment and carry it back to the bacteria. These bacteria also have a receptor that binds to the siderophore, which brings the iron inside, passing through its membranes to the cytoplasm, so it can be used in a number of critical chemical reactions that keep the bacteria functioning and growing. Therefore, if the iron can be taken out of the body with a chelator (which acts like a sponge for iron), the bacteria will be more susceptible to antibiotics because they are in a stressed condition.

SUMMARY OF THE INVENTION

As one aspect of the present invention, a method for preventing or treating a bacterial infection is provided. The method comprises administering an effective amount of a pharmaceutically acceptable iron chelator that reduces biological availability of iron for one or more strains of bacteria to a patient in need of treatment for a bacterial infection.

As another aspect of the present invention, a composition comprises an effective amount of a pharmaceutically acceptable iron chelator that reduces biological availability of iron for one or more strains of bacteria, or an analog or derivative thereof, and an antibiotic. The composition can be a topical formulation, an oral formulation, or an injectable or intravenous formulation.

As yet another aspect of the present invention, a topical composition comprising pharmaceutically acceptable iron chelator that reduces biological availability of iron for one or more strains of bacteria. The composition can be in the form of a gel-like topical formulation or a cream-based topical formulation.

As another aspect of the present invention, a method of treating a patient infected with drug-resistant bacteria is provided. The method comprises the steps of determining whether the patient is infected by bacteria having resistance to one or more antibiotics; administering an effective amount of a pharmaceutically acceptable iron chelator that reduces biological availability of iron for one or more strains of bacteria to the patient; and administering to the patient said one or more antibiotics to which the bacteria has resistance.

In the foregoing methods and compositions, the bacterial infection to be treated may be a wound (such as a skin laceration, particularly a cut or scrape incurred outdoors) or a surgical incision. For example, the method can involve preventing a bacterial infection before or after surgery, particularly by administering the iron chelator to a patient having a heightened risk of a bacterial infection, such as a patient having a wound or a patient undergoing surgery. In some embodiments, the iron chelator may be administered as a prophylactic to prevent bacterial infections. In some preferred embodiments, the iron chelator is selected from the group consisting of VK28, Compound 4, deferiprone, Apo6619, triapine or a pharmaceutically acceptable salt thereof, and rifampin or a pharmaceutically acceptable salt thereof; and mixtures thereof. All of those compounds are discussed in more detail below.

An iron chelator can be administered by itself to a patient, or it may be co-administered with an effective amount of one or more antibiotics to the patient. The antibiotic can be selected from the group consisting of tetracyclines, aminoglycosides, sulfonamides, fluoroquinolones, rifamycins, beta-lactams, oxazolidinones, lincosarnids, peptidyl transferases, glycopeptides, and combinations thereof. Preferably, the antibiotic is a rifamycin, more preferably rifampin. Preferred combinations of iron chelator and antibiotic include Compound 4 and rifampin, deferiprone and rifampin, Apo6619 and rifampin, and triapine and rifampin. Alternative combinations include VK28 and tetracycline and VK28 and rifampin.

It is also contemplated that a combination of iron chelators can be administered to a patient having a bacterial infection. For example, the patient can be administered a composition comprising two or more iron chelators, for example, a combination of any two or more of VK28, Compound 4, deferiprone, Apo6619, triapine, pharmaceutically acceptable salts thereof (or they may be separately administered).

BRIEF DESCRIPTION OF THE FIGURES

FIG. 1 shows the growth curves of AB5711 cultures treated with different iron chelators.

FIG. 8 shows graphs of growth curves depicting the results of time-kill assays.

FIG. 9 shows growth curves depicting the results of time-kill assays against different multi-drug resistant bacteria, namely *E. coli* and MRSA.

FIG. 10 shows the growth curves depicting the results of time-kill assays in combination treatments.

FIG. 39 are pictures depicting the wellplates treated with different concentrations of iron chelator and antibiotic, as labeled along the x-axis and y-axis.

DETAILED DESCRIPTION OF THE PREFERRED EMBODIMENTS

Figure 1A:
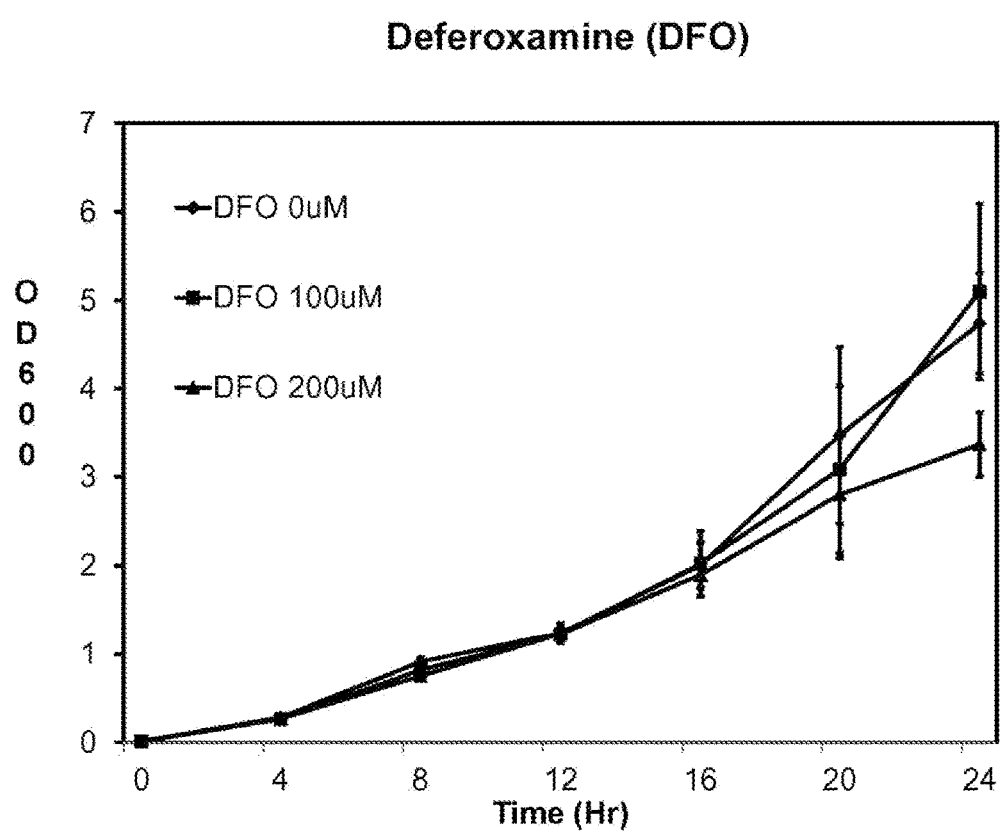
FIG. 1A shows the growth curves of AB5711 cultures treated with 0 μm DFO (♦), 100 μM DFO (■), or 200 μM DFO (▲).

In the following detailed description, for purposes of explanation, numerous specific details are set forth in order to provide a thorough understanding of the various embodiments of the present invention. It will be apparent, however, that the various embodiments of the present disclosure may be practiced without these specific details.

For some embodiments, the present disclosure provides a method of treating a bacterial infection or preventing a bacterial infection, wherein said method is described herein. In some embodiments, the present disclosure provides a prophylactic treatment for bacterial infections wherein said method is described herein. The prophylactic treatment can include treating a patient with the compositions described herein before the presence of a bacterial infection is detected. The bacterial infection may be in a wound. The method can involve preventing a bacterial infection before or after surgery. The present disclosure also provides a method of treating a bacterial infection, wherein said method comprises administering an effective amount of VK28, or a derivative thereof, to a patient in need. The present disclosure also provides a method of treating a bacterial infection, wherein said method comprises administering VK28, or a derivative thereof, and an antibiotic to a patient in need. The present disclosure also provides a method of preventing a bacterial infection, wherein said method comprises administering VK28, or a derivative thereof, to a patient. The present disclosure also provides a method of preventing a bacterial infection, wherein said method comprises administering VK28, or a derivative thereof, and an antibiotic to a patient. The present disclosure also provides a composition comprising VK28, or a derivative thereof, wherein said composition is suitable for topical administration. The composition may be in the form of a gel-like topical formulation or a cream-based topical formulation and can include liquid and ointment formulations. The present disclosure also provides a composition comprising VK28, or a derivative thereof, and an antibiotic. This composition can also be in the form of a gel-like topical formulation or a cream-based topical formulation, or be in a form suitable for oral administration, or be in a form suitable for injection or i.v. administration. For example, the composition can comprise VK28 and tetracycline. The present disclosure also provides an antibacterial composition comprising VK28 and deferiprone.

The present methods and compositions employ one or more pharmaceutically acceptable iron chelators which are effective to reduce the biological availability of iron for one or more strains of bacteria. The iron chelator may reduce the availability by binding iron outside the bacteria and preventing or reducing the ability of the bacteria to absorb the bound iron, and/or the iron chelator may bind iron in the cytoplasm of the bacteria such that the iron is not available for bacterial enzymes, and/or employ some other mechanism so that bacteria are deprived of iron. The pharmaceutically acceptable iron chelators do not have significant toxicity or untolerable adverse effects. It will be recognized that whether an iron chelator is pharmaceutically acceptable will depend on its intended route of administration. For example, an iron chelator administered topically or locally may be pharmaceutically acceptable for that route of administration, whereas it may not be acceptable when administered orally or systemically. Accordingly, a pharmaceutically acceptable iron chelator may be topically acceptable or orally acceptable. As mentioned above, some compounds called siderophores act as iron chelators, but they increase the biological availability of iron for bacteria. The iron chelators contemplated for the present methods are not siderophores, though it is contemplated that siderophore analogs or derivatives may be prepared that do not bind to bacteria or are not uptaken by the bacteria yet still bind to iron; such siderophore analogs and derivatives may be employed in the present methods and compositions. Alternatively, iron chelators may be rationally designed so that they bind iron inside and/or outside the bacterial cell membrane and render the bound iron unavailable to the bacteria for its biological processes. Such rationally designed iron chelators are preferred for the present methods and compositions. By way of example, rationally designed iron chelators may include a nitrogen-containing unsaturated or aromatic ring, for example, a 3-hydroxy-4-oxo-pyridine or a quinoline, for example, an 8-hydroxyquinoline. Preferred iron chelators are those which have been approved by a health regulatory agency (such as the US Food and Drug Administration) for other indications such as defersirox. Assays for determining whether an iron chelator reduces the biological availability for iron for one or more strains of bacteria may be used to determine iron chelators suitable for use in the present methods and compositions. Exemplary assays are disclosed in the examples below.

One example of a pharmaceutically acceptable iron chelator that reduces the biological availability of iron for one or more strains of bacteria VK28. VK28 is an iron chelator that was originally formulated for Alzheimer's disease and Parkinson's disease. VK28 (available from Varinel Inc.) has the structure:

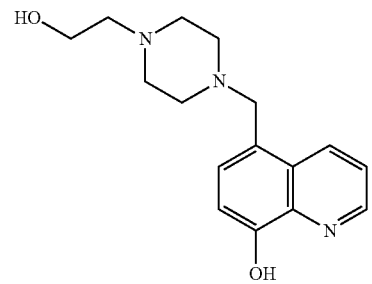 [SMILES: OCCN1CCN(Cc2ccc(O)c3ncccc23)CC1]

The structure and synthesis of VAR10100 (also referred to as VK28) are described in International Publication No. WO 00/74664 and U.S. Pat. No. 6,855,711, entitled "Pharmaceutical Compositions Comprising Iron Chelators for the Treatment of Neurodegenerative Disorders and Some Novel Iron Chelators" (assigned to Yeda Research and Development Co. Ltd. and Technion Research and Development Foundation Ltd), issued Feb. 15, 2005. The chemical structure for VK28 is set forth as compound (15) in this reference, and identified therein as 5-(4-(2-hydroxyethyl)piperazin-1-ylmethyl)-8-hydroxyquinoline)). Synthesis of VK28 is set forth in Example 14 therein. The teachings set forth in U.S. Pat. No. 6,855,711 are incorporated herein by reference in their entirety. VK28 (also referred to as VK-28) is commercially available from Sigma-Aldrich, Inc.

Other preferred iron chelators include analogs and derivatives of VK28, deferiprone (ApoL1), Apo6619, Compound 4 and triapine. Other potential iron chelators for use include dimercaptosuccinic acid, 2,3-dimercapto-1-propanesulfonic acid (DMPS), alpha lipoic acid (ALA), as well as iron chelators disclosed in, for example, U.S. Pat. No. 6,855,711 (Warshawsky et al.), "Pharmaceutical Compositions Comprising Iron Chelators for the Treatment of Neurodegenerative Disorders and Some Novel Iron Chelators," issued 15 Feb. 2005, and U.S. Pat. No. 8,058,442 (Youdim et al.), "Neuroprotective Iron Chelators and Pharmaceutical Compositions Comprising Them," issued 15 Nov. 2011. U.S. Pat.

No. 6,855,711 discloses many other pharmaceutically acceptable iron chelators that may be employed in the present methods and compositions, such as, for example, the 8-hydroxyquinoline derivatives as represented by the Compounds 7, 9-17, 19-21 and 23-26 in Appendix A of that reference. U.S. Pat. No. 8,058,442 disclosed many other pharmaceutically acceptable iron chelators that may be employed in the present methods and compositions, such as, for example, the 8-hydroxyquinoline derivatives disclosed therein.

Deferiprone (available from ApoPharma Inc.) has the structure:

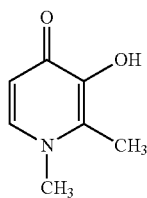

Deferiprone (3-hydroxy-1,2-dimethyl-4(1H)-pyridone) is also commercially available from Sigma-Aldrich.

Apo6619 is known by the chemical name (1-cyclopropyl-3-hydroxy-6-methyl-4-oxo-1,4-dihydro-pyridine-2-carboxylic acid methylamide), and it has the structure:

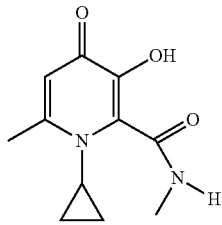 [SMILES: CNC(=O)c1c(O)c(=O)cc(C)n1C1CC1]

Its synthesis is described in Example 3 of US Patent Application Publication No. 20070082904, which discloses other iron chelators which may be used in the present methods and compositions. US Patent Application Publication No. 20080096886 discloses processes for the preparation of iron chelators which may be used in the present methods and compositions.

It is contemplated that other iron chelators that may be employed in the present methods and compositions include 3-hydroxypyridin-4-one compounds of the formula:

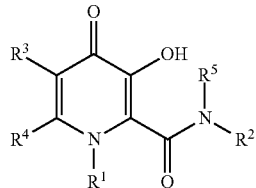

or a pharmaceutically acceptable salt thereof, wherein $R^1$ is X with the proviso that $R_2$ is Y; or $R^1$ is T with the proviso that $R^2$ is W; or $R^1$ is X with the proviso that $R^2R^5N$ when taken together, form a heterocyclic ring selected from piperidinyl, morpholinyl, pyrrolidinyl or piperazinyl, wherein the group piperidinyl, morpholinyl, pyrrolidinyl or piperazinyl is either unsubstituted or substituted with one to three $C_1$-$C_6$ alkyl groups; X is $C_3$-$C_6$ cycloalkyl; Y is selected from the group consisting of $C_3$-$C_6$ cycloalkyl, $C_1$-$C_6$ alkyl and $C_1$-$C_6$ alkyl monosubstituted with a $C_3$-$C_6$ cycloalkyl; T is $C_1$-$C_6$ alkyl: W is $C_3$-$C_6$ cycloalkyl; $R^3$ is selected from the group consisting of hydrogen and $C_1$-$C_6$ alkyl; $R^4$ is selected from the group consisting of hydrogen and $C_1$-$C_6$ alkyl; and $R^5$ is selected from the group consisting of hydrogen and $C_1$-$C_6$ alkyl. Preferably, $R^1$ is X with the proviso that $R^2$ is Y. X is $C_3$-$C_6$ cycloalkyl; Y is $C_1$-$C_6$ alkyl; $R^3$ is hydrogen; $R^4$ is $C_1$-$C_6$ alkyl and $R^5$ is hydrogen. More preferably, $R^4$ is methyl, X is cyclopropyl and Y is methyl, so that the compound is 1-cyclopropyl-3-hydroxy-6-methyl-4-oxo-1,4-dihydro-pyridine-2-carboxylic acid methylamide. Direction for the synthesis of such compounds is found in US Patent Application Publication No. 20070082904.

Deferasirox (marketed as EXJADE by Novartis) is a rationally-designed oral iron chelator. It has been approved by the FDA to reduce chronic iron overload in patients who are receiving long-term blood transfusions for conditions such as beta-thalassemia and other chronic anemias. There are, however, concerns regarding renal failure and cytopenias in patients receiving deferasirox oral suspension tablets. Deferasirox is known by the chemical name [4-[(3Z,5E)-3,5-bis(6-oxo-1-cyclohexa-2,4-dienylidene)-1,2,4-triazolidin-1-yl]benzoic acid and has the structure:

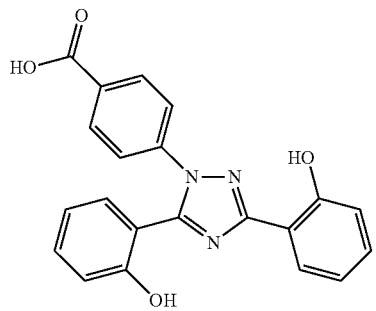 [SMILES: O=C(O)c1ccc(-n2nc(-c3ccccc3O)nc2-c2ccccc2O)cc1]

U.S. Pat. No. 6,465,504 (Lattmann et al.) and U.S. Pat. No. 6,596,750 (Lattmann et al.) disclose the synthesis of deferasirox and other pharmaceutically acceptable iron chelators that may be employed in the present methods and compositions.

Triapine is known by the chemical name 3-aminopyridine-2-carboxaldehyde thiosemicarbazone, and it has the structure:

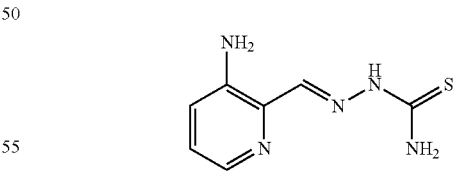

Triapine is also known as 3AP, and it is being developed by Vion Pharmaceuticals as a cancer treatment, but it is contemplated herein as a suitable iron chelator. Its synthesis is disclosed in U.S. Pat. No. 5,869,676 (Vion Pharmaceuticals, now available from Nanotherapeutics Inc.) Triapine is undergoing clinical trials in cooperation with the National Cancer Institute. It is contemplated that other iron chelators that may be employed in the present methods and compositions include 3-aminopyridine compounds such as 3-AMP, also disclosed in U.S. Pat. No. 5,869,676.

Among the analogs and derivatives of VK28 contemplated for the present methods and compositions are Compound 4 in PCT Application No. PCT/US2012/23330 entitled "Neuroprotective and Antibacterial Iron Chelators and Compositions Comprising Them", filed on Jan. 31, 2012 and assigned to Varinel Inc. (bearing Attorney Docket No. VAR-008 in the offices of Ben-Ami & Associates, Rehovot, Israel). That reference describes the structure and synthesis of Compound 4, along with the structure and synthesis of numerous other pharmaceutically acceptable iron chelators. The structure of this compound, hereinafter referred to as "Compound 4", is:

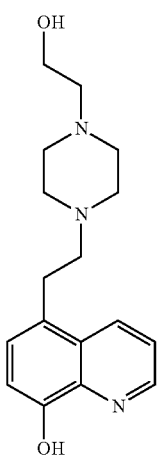

4

Other iron chelators for use in the present methods and compositions employ a compound of the formula I:

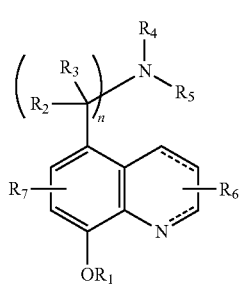

I wherein
$R_1$ is selected from:
(i) H;
(ii) $C_1$-$C_8$ alkyl substituted by one or more radicals selected from hydroxy, $C_1$-$C_8$ alkoxy, cyano, carboxy, aminocarbonyl, $C_1$-$C_8$ alkylaminocarbonyl, di($C_1$-$C_8$)alkylaminocarbonyl, and $C_1$-$C_8$ alkoxycarbonyl;
(iii) —$COR_8$, wherein $R_8$ is $C_1$-$C_8$ alkyl, $C_2$-$C_8$ alkenyl, $C_2$-$C_8$ alkynyl, $C_3$-$C_8$ cycloalkyl, aryl, heteroaryl, or heterocyclyl wherein said alkyl, alkenyl, alkynyl, aryl, heteroaryl, or heterocyclyl group is optionally substituted by one or more of the following groups: halogen atoms, $C_1$-$C_8$ alkyl, hydroxy, amino, $C_1$-$C_8$ alkylamino, di($C_1$-$C_8$)alkylamino, mercapto, $C_1$-$C_8$ alkylthio, cyano, $C_1$-$C_8$ alkoxy, carboxy, $C_1$-$C_8$ (alkoxy)carbonyl, $C_1$-$C_8$ (alkyl)carbonyloxy, $C_1$-$C_8$ (alkyl)sulfonyl, $C_1$-$C_8$ (alkyl)carbonylamino, aminocarbonyl, $C_1$-$C_8$ (alkyl)aminocarbonyl, or di($C_1$-$C_8$)alkylaminocarbonyl, or a straight or branched $C_1$-$C_5$ alkyl may be substituted by amino at the α-position to the CO group, and the alkyl is optionally further substituted at a different position by hydroxy, amino, guanidino, mercapto, methylthio, carboxy, aminocarbonyl, phenyl, 4-hydroxyphenyl, 2-indolyl or 5-imidazolyl such as to form an amino acid residue derived from glycine, alanine, valine, leucine, isoleucine, serine, threonine, lysine, arginine, cysteine, methionine, aspartic, glutamic, asparagine, glutamine, phenylalanine, tyrosine, tryptophan or histidine, or the amino group and the alkyl chain form a 5-membered ring to form a proline residue.

(iv) —$COOR_9$, wherein $R_9$ is $C_1$-$C_8$ alkyl optionally substituted by halogen, $C_1$-$C_8$ alkoxy, phenyl optionally substituted by nitro, hydroxy, carboxy, or $C_3$-$C_6$ cycloalkyl; $C_2$-$C_4$ alkenyl; $C_2$-$C_4$ alkynyl; $C_5$-$C_7$ cycloalkyl; or phenyl optionally substituted by halogen, amino, nitro, $C_1$-$C_8$ alkyl, $C_1$-$C_8$ (alkoxy)carbonyl, or $C_1$-$C_8$ alkoxy;
(v) —$CH_2$—O—CO—$R_{10}$, or —$CH(CH_3)$—O—CO—$R_{10}$, wherein $R_{10}$ is $C_1$-$C_8$ alkyl optionally substituted by halogen, $C_1$-$C_8$ alkoxy; $C_2$-$C_4$ alkenyl optionally substituted by phenyl; $C_3$-$C_6$ cycloalkyl; phenyl optionally substituted by $C_1$-$C_8$ alkoxy; or heteroaryl selected from furyl, thienyl, isoxazolyl, or pyridyl optionally substituted by halogen or $C_1$-$C_8$ alkyl;
(vi) —$PO(OR_{11})_2$, —$CH_2$—O—$PO(OR_{11})_2$ or —$CH(CH_3)$—O—$PO(OR_{11})_2$, wherein $R_{11}$ is independently selected from H, $C_1$-$C_8$ alkyl, or $C_1$-$C_8$ alkyl optionally substituted by hydroxy, $C_1$-$C_8$ alkoxy, or $C_1$-$C_8$ (alkyl)carbonyloxy; and
(vii) —$CONR_{12}R_{13}$, wherein $R_{12}$ and $R_{13}$ are independently selected from H, $C_1$-$C_8$ alkyl, $C_2$-$C_8$ alkenyl, $C_2$-$C_8$ alkynyl, $C_3$-$C_8$ cycloalkyl, aryl, arylalkyl, heteroaryl, or heterocyclyl wherein said alkyl, alkenyl, alkynyl, aryl, heteroaryl, heteroarylalkyl, heterocyclyl or heterocyclylalkyl group is optionally substituted by one or more of the groups: halogen atoms, $C_1$-$C_8$ alkyl, hydroxy, amino, $C_1$-$C_8$ alkylamino, di($C_1$-$C_8$)alkylamino, mercapto, $C_1$-$C_8$ alkylthio, cyano, $C_1$-$C_8$ alkoxy, carboxy, $C_1$-$C_8$ (alkoxy)carbonyl, $C_1$-$C_8$ (alkyl)carbonyloxy, $C_1$-$C_8$ (alkyl)sulfonyl, $C_1$-$C_8$ (alkyl)carbonylamino, aminocarbonyl, $C_1$-$C_8$ (alkyl)aminocarbonyl, and di($C_1$-$C_8$)alkylaminocarbonyl, or a straight or branched $C_1$-$C_5$ alkyl may be substituted by a carboxy group at the α-position to the amino group, and the alkyl is optionally further substituted at a different position by hydroxy, amino, guanidino, mercapto, methylthio, carboxy, aminocarbonyl, phenyl, 4-hydroxyphenyl, 2-indolyl or 5-imidazolyl such as to form an amino acid residue derived from glycine, alanine, valine, leucine, isoleucine, serine, threonine, lysine, arginine, cysteine, methionine, aspartic, glutamic, asparagine, glutamine, phenylalanine, tyrosine, tryptophan or histidine, or the amino group and the alkyl chain form a 5-membered ring to form a proline residue; or $R_{12}$ and $R_{13}$ together with the N atom to which they are attached form a 5 to 7 membered saturated ring optionally further containing a heteroatom selected from O, S and N, optionally substituted by $C_1$-$C_8$ alkyl;

$R_2$ and $R_3$ each independently is selected from a group consisting of H, $C_1$-$C_8$ alkyl, halogen, halo($C_1$-$C_8$)alkyl, OH, $C_1$-$C_8$ alkoxy, amino, $C_1$-$C_8$ alkylamino, di($C_1$-$C_8$) alkylamino, $C_1$-$C_8$ (alkyl)carbonylamino, carboxy, or $C_1$-$C_8$ (alkyl)carbonyloxy;

$R_4$ and $R_5$ together with the nitrogen atom to which they are attached form a 5-8 membered heterocyclic ring that may contain one or more nitrogen, oxygen, or sulfur atoms and may be optionally substituted at any available position in the ring with one or more radicals selected from the group consisting of H, $C_1$-$C_8$ alkyl, halogen, halo($C_1$-$C_8$)alkyl, cyano, cyano($C_1$-$C_8$)alkyl, ($C_1$-$C_8$)alkoxy, ($C_1$-$C_8$)alkoxy ($C_1$-$C_8$)alkyl, hydroxy, hydroxy($C_1$-$C_8$)alkyl, amino, ($C_1$-$C_8$)alkylamino, di($C_1$-$C_8$)alkylamino, amino($C_1$-$C_8$)alkyl, ($C_1$-$C_8$)alkylamino($C_1$-$C_8$)alkyl, di($C_1$-$C_8$)alkylamino($C_1$-$C_8$)alkyl, oxo, formyl, acyl, carboxy, ($C_1$-$C_8$)alkoxycarbonyl, carboxy($C_1$-$C_8$)alkyl, acyloxy, acyloxy($C_1$-$C_8$)alkyl, acylamino, acylamino($C_1$-$C_8$)alkyl, ($C_1$-$C_8$)alkylsulfonyl, and arylsulfonyl radicals;

$R_6$ is H, $C_1$-$C_8$ alkyl, mercapto, $C_1$-$C_8$ alkylthio, amino, $C_1$-$C_8$ alkylamino, $C_1$-$C_8$ alkylimino, di($C_1$-$C_8$)alkylamino, hydroxy, or $C_1$-$C_8$ alkoxy; or imino, oxo or thioxo at the 2- or 4-positions;

$R_7$ is H, halogen, $C_1$-$C_8$ alkyl, $C_3$-$C_8$ cycloalkyl, halo($C_1$-$C_8$)alkyl, cyano, ($C_1$-$C_8$)alkoxy, hydroxy, amino, ($C_1$-$C_8$) alkylamino, di($C_1$-$C_8$)alkylamino, nitro, acyloxy, acylamino, ($C_1$-$C_8$)alkylthio, ($C_1$-$C_8$)alkylsulfenyl, or ($C_1$-$C_8$) alkylsulfonyl;

each of the dotted lines indicates an optional bond; and
n is an integer from 1 to 8,
and pharmaceutically acceptable salts thereof,
but excluding the compound wherein $R_1$, $R_2$, $R_3$, $R_6$, $R_7$ are H; n is 1; and $R_4$ and $R_5$ together with the N atom to which they are attached form a piperazino ring substituted at the 4-position by 2-hydroxyethyl. Additional detail about such compounds and their synthesis are found in PCT Application No. PCT/US2012/23330 entitled "Neuroprotective and Antibacterial Iron Chelators and Compositions Comprising Them", filed on Jan. 31, 2012 and assigned to Varinel Inc. (bearing Attorney Docket No. VAR-008 in the offices of Ben-Ami & Associates).

Other iron chelators for use in the present methods and compositions employ the compounds a compound of the formula II:

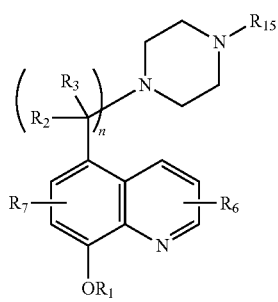

II wherein
$R_1$, $R_2$, $R_3$ and $R_7$ each is as defined in formula I;
$R_6$ is H, $C_1$-$C_8$ alkyl, mercapto, $C_1$-$C_8$ alkylthio, amino, $C_1$-$C_8$ alkylamino, $C_1$-$C_8$ alkylimino, di($C_1$-$C_8$)alkylamino, hydroxy, or $C_1$-$C_8$ alkoxy;

$R_{15}$ is H, $C_1$-$C_8$ alkyl, halogen, halo($C_1$-$C_8$)alkyl, cyano, cyano($C_1$-$C_8$)alkyl, ($C_1$-$C_8$)alkoxy, ($C_1$-$C_8$)alkoxy($C_1$-$C_8$) alkyl, hydroxy, hydroxy($C_1$-$C_8$)alkyl, amino, ($C_1$-$C_8$)alkylamino, di($C_1$-$C_8$)alkylamino, amino($C_1$-$C_8$)alkyl, ($C_1$-$C_8$) alkylamino($C_1$-$C_8$)alkyl, di($C_1$-$C_8$)alkylamino($C_1$-$C_8$)alkyl, oxo, formyl, acyl, carboxy, carboxy($C_1$-$C_8$)alkyl, ($C_1$-$C_8$) alkyloxycarbonyl, acyloxy, acyloxy($C_1$-C8)alkyl, acylamino, acylamino($C_1$-$C_8$)alkyl, ($C_1$-$C_8$)alkylsulfonyl or arylsulfonyl, n is an integer from 1 to 8, and
pharmaceutically acceptable salts thereof, but excluding the compound wherein $R_1$, $R_2$, $R_3$, $R_6$, $R_7$ are H; n is 1 and $R_{15}$, is 2-hydroxyethyl. Formula II provides compounds where $R_4$ and $R_5$ together with the N atom to which they are attached form a piperazino ring that may substituted at the 4 position.

In certain embodiments, the compounds of the invention are the compounds of formula II wherein $R_{15}$ is 2-hydroxyethyl and in particular the compounds wherein $R_1$ is H, $R_2$, $R_3$, $R_6$ and $R_7$ each is as defined above, $R_{15}$ is 2-hydroxyethyl and n is an integer from 2 to 5, preferably 2 or 3. Additional detail about such compounds and their synthesis are found in PCT Application No. PCT/US2012/23330 entitled "Neuroprotective and Antibacterial Iron Chelators and Compositions Comprising Them", filed on Jan. 31, 2012 and assigned to Varinel Inc. (bearing Attorney Docket No. VAR-008 in the offices of Ben-Ami & Associates).

For the above noted compound I and II, the terms used are defined below:

The term "halogen" as used herein refers to fluoro, chloro, bromo and iodo, and is preferably Cl or F.

The term "$C_1$-$C_8$ alkyl", alone or as part of a radical containing an alkyl group, typically means a straight or branched alkyl having 1 to 8, preferably 1 to 6, 5, 4, 3, 2 or 1 carbon atoms and includes, without being limited to, methyl, ethyl, n-propyl, isopropyl, n-butyl, sec-butyl, isobutyl, tert-butyl, n-pentyl, 1-methylbutyl, 2,2-dimethylpropyl, n-hexyl, n-heptyl, n-octyl, and the like. The alkyl radical may be substituted, without being limited to, by one or more OH, SH, COOH, $CONH_2$, CN, cycloalkyl (e.g., cyclohexyl, optionally substituted by alkyl), aryl (e.g., phenyl, optionally substituted by $NO_2$), alkoxy, alkoxycarbonyl, alkylcarbonyloxy, and heteroaryl or heterocyclyl (e.g., furyl, thienyl, piperidino). The term "halo($C_1$-$C_8$)alkyl" refers to $C_1$-$C_8$ alkyl, preferably $C_1$-C5 alkyl substituted by one or more F atoms or by one or more F and Cl atoms. In certain embodiments the haloalkyl is pentafluoropentyl. In certain embodiments, the haloalkyl is methyl substituted by 1, 2 or 3 F atoms or by F and Cl such as —$CH_2F$, —$CHF_2$, —$CF_3$, or —$CClF_2$. In certain embodiments, the haloalkyl is ethyl substituted by 1 to 5 F atoms such as —$CHFCH_3$, —$CF_2CH_3$, —$CF_2CFH_2$, —$CF_2CF_2H$, —$CH_2CF_3$, or —$CF_2CF_3$.

The terms "$C_2$-$C_8$ alkenyl" and "$C_2$-$C_8$ alkynyl" typically mean a straight or branched radical having 2-8, preferably 2, 3 or 4, carbon atoms and one double or triple bond: respectively, and include, without being limited to, vinyl, allyl, prop-1-en-1-yl, prop-2-en-1-yl, but-3-en-1-yl, 2,2-dimethylvinyl, 2-ethenylbutyl, oct-3-en-1-yl, and the like, and ethynyl, propargyl, but-3-yn-1-yl, pent-3-yn-1-yl, and the like. The alkenyl radical may be substituted, for example, by aryl, e.g., phenyl.

The terms "$C_1$-$C_8$ alkoxy" and "$C_1$-$C_8$ alkylthio" as used herein typically mean a straight or branched radical having 1-8, preferably 1, 2, or 3 carbon atoms, and being preferably a substituent of an alkyl, phenyl or heteroaryl radical. Examples of alkoxy include methoxy, ethoxy, propoxy, isopropoxy, butoxy, pentoxy, and the like and of alkylthio include methylthio, ethylthio, propylthio, isopropylthio, butylthio and the like.

The term "$C_3$-$C_8$ cycloalkyl" refers herein to a cycloalkyl radical comprising one or two rings such as cyclopropyl, cyclobutyl, cyclopentyl, cyclohexyl, cycloheptyl, cyclooctyl, adamantyl, bicyclo[3.2.1]octyl, bicyclo[2.2.1]heptyl, and the like, that may be substituted, for example, by one or more alkyl groups.

The term "aryl" refers to a $C_6$-$C_{14}$ aryl, namely, to an aromatic carbocyclic group having 6 to 14 carbon atoms consisting of a single ring or multiple rings either condensed or linked by a covalent bond such as, but not limited to, phenyl, naphthyl, carbazolyl, phenanthryl, and biphenyl. In certain embodiments, the aryl radical is phenyl optionally substituted by halogen, $C_1$-$C_8$ alkyl, $C_1$-$C_8$ alkoxy, nitro, $C_3$-$C_8$ cycloalkyl, cyano, hydroxy, mercapto, ($C_1$-$C_8$)alkylthio, ($C_1$-$C_8$)alkylsulfenyl, ($C_1$-$C_8$)alkylsulfonyl, carboxy, ($C_1$-$C_8$)alkoxycarbonyl, ($C_1$-$C_8$)alkylcarbonyl, amino, ($C_1$-$C_8$)alkylamino, di($C_1$-$C_8$)alkylamino, formyl, aminocarbonyl, ($C_1$-$C_8$)alkylaminocarbonyl, di($C_1$-$C_8$)alkylaminocarbonyl, acylamino, and/or ($C_1$-$C_8$)alkylsulfonylamino. In some preferred embodiments, the aryl radical is phenyl, optionally substituted by halogen, e.g.: F, alkyl, e.g., methyl, alkoxy, e.g., methoxy, and/or nitro.

The term "heteroaryl" refers to a radical derived from a mono- or poly-cyclic heteroaromatic ring containing one to three heteroatoms selected from the group consisting of N, O and S. When the heteroaryl is a monocyclic ring, it is preferably a radical of a 5-6-membered ring such as, but not limited to, pyrrolyl, furyl, thienyl, pyrazolyl, imidazolyl, oxazolyl, isoxazolyl, thiazolyl, isothiazolyl, pyridyl, pyrimidinyl, 1,3,4-triazinyl, 1,2,3-triazinyl, and 1,3,4-triazinyl. Polycyclic heteroaryl radicals are preferably composed of two rings such as, but not limited to, benzofuryl, isobenzofuryl, benzothienyl, indolyl, quinolinyl, isoquinolinyl, imidazo[1,2-a]pyridyl, benzimidazolyl, benzothiazolyl and benzoxazolyl. It is to be understood that when a polycyclic heteroaromatic ring is substituted, the substitutions may be in any of the carbocyclic and/or heterocyclic rings. In some embodiments, the heteroaryl is furyl, thienyl: isoxazolyl, pyridyl (optionally substituted by Cl), indolyl, or imidazolyl.

The term "heterocyclyl" refers to a radical derived from a mono- or poly-cyclic non-aromatic ring containing one to three heteroatoms selected from the group consisting of N, O and S. Examples of such radicals include, without limitation, piperidinyl, 4-morpholinyl, pyrrolidinyl.

As used herein, "n" is an integer from 1 to 8, preferably from 1 to 5. In certain embodiments, n is 1, 2 or 3.

Another example of a pharmaceutically acceptable iron chelator is M30. The structure and synthesis of M30 are described in WO 2004/041151 and U.S. Pat. No. 8,058,442 (assigned to Yeda Research and Development Co. Ltd. and Technion Research and Development Foundation Ltd). M30 has the structure:

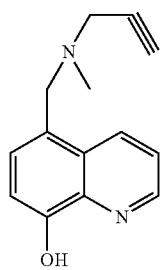 [SMILES: C#CCN(C)Cc1ccc(O)c2ncccc12]

M30 is an iron chelator that has another pharmacophores which may also work in the present methods and compositions. Another iron chelator which may work in the present methods and compositions is VAR10303, the structure and synthesis of which are described in PCT Application No. PCT/IB2011/053590 assigned to Varinel Inc.

Not every iron chelator is suitable for inclusion in the present methods and compositions, and it is contemplated that one of ordinary skill in the art can recognize suitable iron chelators in light of the present disclosure and through routine experimentation. For example, deferoxamine (available as Desferal from Novartis Ag) has the structure:

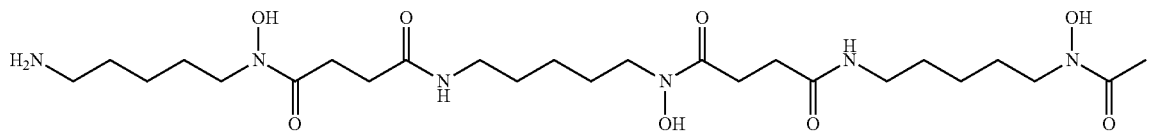 [SMILES: CC(=O)N(O)CCCCCNC(=O)CCC(=O)N(O)CCCCCNC(=O)CCC(=O)N(O)CCCCCN]

Deferoxamine is approved by the FDA, but it is a siderophore, a molecule secreted by bacteria to capture iron, so it is generally not effective to treat bacterial infection, as many bacteria have a receptor to capture this molecule or like molecules. However it is contemplated that analogs or derivatives of deferoxamine may be prepared which reduce the biological availability of iron for one or more strains of bacteria.

2,2-dipyridyl (available from Sigma) has the structure:

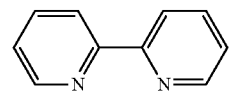

However, 2,2-dipyridyl is not a pharmaceutically acceptable iron chelator, though analogs or derivatives may be prepared which are pharmaceutically acceptable.

For treating and/or preventing bacterial infections, VK28, or an analog or derivative thereof, or another a pharmaceutically acceptable iron chelator that reduces biological availability of iron for one or more strains of bacteria may be administered topically, orally, via injection, intravenously (i.v.) or intranasally as an aerosol.

In one aspect, topical compositions containing a topically acceptable iron chelator are provided. In another aspect, pharmaceutical compositions containing a pharmaceutically acceptable iron chelator and an antibiotic are provided.

Compositions containing a pharmaceutically acceptable iron chelator that reduces biological availability of iron for one or more strains of bacteria such as VK28, or a derivative thereof, and an antibiotic may be formulated for topical, oral, injection, intravenous or intranasal administration by incorporating the iron chelator and antibiotic into a pharmaceutically acceptable carrier using conventional or otherwise appropriate, pharmaceutical preparation methodologies. One having ordinary skill in the art will recognize suitable pharmaceutical carriers that may be employed, as well as methods for preparing the compositions herein.

For topical use, for example, the composition may be formulated into a gel-like or cream-based formulation. Suitable carriers for such purpose include, for example purposes only, Pluronic® 127 (Sigma product no. P2443) and Poloxamer 407 (Sigma product no. 16758), both available from Sigma-Aldrich, Inc. At 4° C. these are liquid, but >30° C. they form a gel. VK28, or other iron chelator, may, for example, be mixed in a 1:1 ratio with the poloxamer. Alternatively, it can be a ratio in the range from about 10:1 to about 1:10. In addition, VK28 may be incorporated into a suitable topical cream base or into a wound healing cream such as a NeosporinR-like or Triderma MDR-type formulations—for example, a formulation that stimulates collagen rebuilding, growth factors (VEGF, FGF), etc. In some embodiments, the topical formulation can be an ointment, including, for example, an oil in water emulsion or an water in oil emulsion. In some embodiments the ointment is based on petroleum derived oils or derivatives thereof or other suitable oil phase, including, but not limited to, for example, monoglycerides, diglycerides, triglycerides fatty acids, fatty alcohols, vegetable oils, mineral oils, their derivatives and mixture thereof. A suitable ointment can include low molecular weight cocoa butter, cottonseed oil, sodium pyruvate, tocopheryl acetate, and petroleum jelly. Formulations of ointments are known by one skilled in the art. The iron chelator can be provided in a liposome, a lipid carrier, a nanoparticle, a nanovesicle or other delivery vehicle.

The iron chelator is employed in an amount effective for the treatment and/or prevention of bacterial infection. The effective dosage seen in vitro is up to 2 mM based on molarity or up to 1 mg/mL. 2 mM or 1 mg/mL is an extremely high dosage for translating into in vivo. Previous experiments by Varinel Inc. have shown toxicity with VK28 at 30 mg/kg in a mouse or 70 mg/kg in a rat when delivered systemically/intravenously. Based on these results, for systemic delivery, the maximum dose for a human without adverse side-effects would be approximately 60 mg/kg. Higher doses are suitable for topical administration. The iron chelator can present in an amount that is up to about 10% by weight, alternatively up to about 20% by weight of the topical composition. In some embodiments, the topical composition can comprise about 0.1% to about 20% of at least one iron chelator, alternatively about 1% to about 20%, alternatively about 5% to about 20%, alternatively about 5% to about 10%, and include, but are not limited to, for example, about 1%, about 2%, about 3%, about 4%, about 5%, about 6%, about 7%, about 8%, about 9%, about 10%, about 12%, about 15%, about 20%, and includes percentages and ranges there between and in increments of about 0.1%, about 0.25%, about 0.5%, about 1% and the like. Determination of an effective amount of VK28, or derivative thereof, to employ is well within the skill of one having ordinary skill in the art having knowledge of the teachings set forth herein.

In some aspects of the present invention, one or more iron chelators (for example Compound 4, VK28, or its analogs or derivatives, or Apo6619) may be used in a composition or method for treating a bacterial infection with one or more antibiotics. The antibiotic(s) may be selected from conventional antibiotics such as (1) tetracyclines (for example, Doxycycline, Chlortetracycline, Clomocycline, Demeclocycline, Lymecycline, Meclocycline, Metacycline, Minocycline, Oxytetracycline, Penimepicycline, Rolitetracycline, Tetracycline), (2) aminoglycosides (for example, gentamicin, kanamycin, amikacin, arbekacin, etc.), (3) sulfonamides including in combination with Trimethoprim, (4) fluoroquinolones, (5) rifamycins, (6) beta-lactams (for example all carbapenems, penicillins, and cephalosporins), (7) oxazolidinones (for example, Linezolid, Torezolid, Eperezolid, Posizolid, Radezolid), (8) Lincosamids (for example, including clindamycin and lincomycin), (9) peptidyl transferases (for example, amphenicols), and/or (10) glycopeptides (for example, including Vancomycin or Teicoplanin). Exemplary antibiotics falling within categories (1)-(10) were tested, and none were inhibited by VK28. In a study of 30 antibiotics to determine if VK28 inhibited their activity, it was found that VK28 only inhibited the activity of one antibiotic, namely thiamphenicol, which is used in Brazil for eye infections. Methods and compositions comprising one or more iron chelators with one or more of each of the foregoing antibiotics are hereby disclosed.

Dosages of antibiotics as used in the present technology are readily known to one skilled in the art. When an antibiotic is used in combination with an iron chelator, the dosage of antibiotic may be reduced as compared to the dosage if used alone, if desired.

Alternatively or additionally, the iron chelator (for example Compound 4, VK28, or its analogs or derivatives, Apo6619) may be coupled with other non-traditional/unconventional antibacterial approaches such as (1) anti-biofilm drugs (for example, dispersin B, 2-aminoimidazoles), (2) antibodies (polyclonal or monoclonal) that kill bacteria or disrupt bacterial growth (for example, block iron uptake or disrupt biofilms), (3) quorum sensing molecules that disrupt biofilms, (4) bacteriophage and pyocins, (5) gallium nitrate and gallium maltolate formulations, and/or (6) another iron chelator such as deferiprone or deferasirox (EXJADE).

Selection of a suitable antibiotic to employ herein is well within the skill of the art in light of the present disclosure. Some combinations of particular iron chelators with particular antibiotics are surprisingly effective for the treatment of drug-resistant bacterial infections. For example, for an infection with *A. baumannii*, a preferred method is to administer an effective amount of rifampin with a pharmaceutically acceptable iron chelator that is effective to reduce availability of iron for biological processes of *A. baumannii*, more preferably deferiprone, Compound 4 or VK28. For an infection with *P. aeruginosa*, a preferred method may include an effective amount of deferiprone with an antibiotic, such as amikacin, doxycycline, cefotaxine, colistin, or rifampin.

Also contemplated for the present methods and compositions are pharmaceutically acceptable salts of the iron chelators and/or the antibiotics. Pharmaceutically acceptable salts are formed with metals or amines, such as alkali and alkaline earth metals or organic amines, or a quaternary salt. Pharmaceutically acceptable acid addition salts include salts derived from inorganic acids and organic acids. Also contemplated are salts of amino acids. See, for example, Berge S. M., et al., "Pharmaceutical Salts," J. Pharm. Sci., 66:1-19 (1977). Acid addition salts of basic compounds can be prepared by contacting the free base form with a sufficient amount of the desired acid to produce the salt. The base addition salts of acidic compounds can be prepared by contacting the free acid form with a sufficient amount of the desired base to produce the salt.

In some embodiments, methods of treating or preventing bacterial infections are provided comprising administering a patent in need of treatment a pharmaceutically acceptable iron chelator that reduces biological availability of iron for one or more strains of bacteria and an antibiotic other than an aminoglycoside. Compositions comprising a pharmaceutically acceptable iron chelator that reduces biological availability of iron for one or more strains of bacteria and an antibiotic other than an aminoglycoside are also contemplated.

In some embodiments, methods of treating or preventing bacterial infections are provided comprising administering a patent in need of treatment VK28, or a derivative, or a pharmaceutically acceptable salt thereof, and rifampin. Compositions comprising VK28, or a derivative, or a pharmaceutically acceptable salt thereof, and rifampin are also contemplated. In some embodiments, methods of treating or preventing bacterial infections are provided comprising administering a patent in need of treatment compound 4 (as described herein) or a pharmaceutically acceptable salt thereof, and rifampin. Compositions comprising compound 4 (as described herein) or a pharmaceutically acceptable salt thereof, and rifampin are also contemplated. In some embodiments, methods of treating or preventing bacterial infections are provided comprising administering a patent in need of treatment deferiprone or a pharmaceutically acceptable salt thereof, and rifampin. Compositions comprising deferiprone or a pharmaceutically acceptable salt thereof, and rifampin are also contemplated. In some embodiments, methods of treating or preventing bacterial infections are provided comprising administering a patent in need of treatment Apo6619 or a pharmaceutically acceptable salt thereof, and rifampin. Compositions comprising Apo6619 or a pharmaceutically acceptable salt thereof, and rifampin are also contemplated. In any of the foregoing methods and compositions, the bacterial infection may be *Acinetobacter baumannii* (Ab), *Escherichia coli* (Ec), *Klebsiella pneumoniae* (Kp), Methicillin-Resistant *Staphylococcus aureus* (MRSA), or *Pseudomonas aeruginosa* (Pa). The present methods and compositions may be used to treat infections of various types of bacteria, such as *Acinetobacter baumannii* (Ab), *Escherichia coli* (Ec), *Klebsiella pneumoniae* (Kp), Methicillin-Resistant *Staphylococcus aureus* (MRSA), *Pseudomonas aeruginosa* (Pa), and others. In some embodiments, the present methods and compounds are used for treating infections of multi-drug resistant organisms (MDROs). By way of example, the present methods and compounds are used to treat or prevent infections of one or more of *Acinetobacter baumannii, Escherichia coli* (Ec), *Klebsiella pneumoniae* (Kp), Methicillin-Resistant *Staphylococcus aureus* (MRSA), *Pseudomonas aeruginosa* (Pa). In some embodiments, particular iron chelators alone or in combination with particular antibiotics may be used for particular types of bacteria.

In some embodiments, methods are providing for potentiating an antibiotic against a bacterial strain having resistance to that antibiotic. The methods comprise administering a pharmaceutically acceptable iron chelator that reduces biological availability of iron to the bacterial strain in combination with the antibiotic.

Accordingly, in some embodiments, the present methods include the step of determining a type of bacterial infection, for example, determining what strain of bacteria infects a patient. The methods can then include the step of selecting an iron chelator based upon the determination of the bacterial infection type. The methods can also include the step of administering the selected iron chelator. For example, if it is determined that the bacterial infection is caused by *Acinetobacter baumannii* (Ab), the method can comprise administering an iron chelator and antibiotic, preferably selected from the group consisting of the following combinations: deferiprone or a pharmaceutically acceptable salt thereof, and rifampin or a pharmaceutically acceptable salt thereof; compound 4 or a pharmaceutically acceptable salt thereof, and rifampin or a pharmaceutically acceptable salt thereof; triapine or a pharmaceutically acceptable salt thereof, and rifampin or a pharmaceutically acceptable salt thereof; Apo6619 or a pharmaceutically acceptable salt thereof, and rifampin or a pharmaceutically acceptable salt thereof; Apo6619 or a pharmaceutically acceptable salt thereof, and colistin or a pharmaceutically acceptable salt thereof; Apo6619 or a pharmaceutically acceptable salt thereof, and cefotaxine or a pharmaceutically acceptable salt thereof; Apo6619 or a pharmaceutically acceptable salt thereof, and amikacin or a pharmaceutically acceptable salt thereof. If it is determined that the bacterial infection is caused by *Pseudomonas aeruginosa* (PA), then the method can comprise administering a selected iron chelator, preferably deferiprone or a pharmaceutically acceptable salt thereof, and a selected antibiotic, preferably an antibiotic selected from the group consisting of rifampin, doxycycline, colistin, cefotaxine, pharmaceutically acceptable salts thereof, and combinations thereof. Alternatively, if the bacterial infection is determined to be caused by PA the method can comprise administering compound 4 or a pharmaceutically acceptable salt thereof and an antibiotic, preferably an antibiotic selected from the group consisting of rifampin, doxycycline, colistin, cefotaxine, pharmaceutically acceptable salts thereof, and combinations thereof. If it is determined that the bacterial infection is caused by *Escherichia coli* (EC), the method can comprise administering an antibiotic, preferably rifampin or a pharmaceutically acceptable salt thereof, and an iron chelator selected from the group consisting of compound 4, VK28 or an analog or derivative thereof, deferiprone, Apo6619, triapine, pharmaceutically acceptable salts thereof, and combinations thereof. It is contemplated that more than one iron chelator and/or more than one antibiotic may be selected and administered after determining the bacterial strain causing the bacterial infection in the patient.

Techniques for determining the genus and/or species of bacteria infecting a patient, including such as *Acinetobacter baumannii* (Ab), *Escherichia coli* (Ec), *Klebsiella pneumoniae* (Kp), and *Pseudomonas aeruginosa* (Pa), are known to one skilled in the art and can include, but are not limited to, classical phenotypic identification methods, for example, e.g. culturing of samples in select media under conditions readily known in the art and undergoing morphological/pathological and biochemical detection methods including, e.g. Gram staining and morphological examination. Additionally, molecular biology techniques may be employed for detection of the different bacteria strains, including, but not limited to, for example, PCR, DNA-hybridization, western blot analysis, enzymatic tests, other clinical laboratory techniques, among others. Suitable techniques for detecting type and strain of bacteria and bacterial antibiotic resistances can be found at, for example, the website of the Clinical and Laboratory Standards Institute, http://www.clsi.org/. Additionally, suitable commercial instruments for microbial screening and identification may be used to determine the bacterial species and strains, including, for example, PROFILE® 1 (New Horizons, Diagnostics, Inc), Phoenix™ Automated Microbiology System (BD Biosciences, Sparks, Md.), VITEK® 2 (bioMérieux, Inc, Durham, N.C.), PLEX-ID, available from Abbott Ibis Biosciences (Abbott Park, Ill.).

In some embodiments, the iron chelator and the antibiotic are selected from the group consisting of the following combinations: VK28, or a derivative, or a pharmaceutically acceptable salt thereof, and rifampin or a pharmaceutically acceptable salt thereof; compound 4 or a pharmaceutically acceptable salt thereof, and rifampin or a pharmaceutically acceptable salt thereof; deferiprone or a pharmaceutically acceptable salt thereof, and rifampin or a pharmaceutically acceptable salt thereof; Apo6619 or a pharmaceutically acceptable salt thereof, and rifampin or a pharmaceutically acceptable salt thereof; VK28, or a derivative, or a pharmaceutically acceptable salt thereof, and tetracycline or a pharmaceutically acceptable salt thereof; compound 4 or a pharmaceutically acceptable salt thereof, tetracycline or a pharmaceutically acceptable salt thereof, deferiprone or a pharmaceutically acceptable salt thereof, and tetracycline or a pharmaceutically acceptable salt thereof; and Apo6619 or a pharmaceutically acceptable salt thereof, and tetracycline or a pharmaceutically acceptable salt thereof.

In other embodiments, when the bacterial infection is caused by *Acinetobacter baumannii* (Ab), the iron chelator and the antibiotic are selected from the group consisting of the following combinations: deferiprone or a pharmaceutically acceptable salt thereof, and rifampin or a pharmaceutically acceptable salt thereof; triapine or a pharmaceutically acceptable salt thereof, and rifampin or a pharmaceutically acceptable salt thereof; Apo6619 or a pharmaceutically acceptable salt thereof, and rifampin or a pharmaceutically acceptable salt thereof; Apo6619 or a pharmaceutically acceptable salt thereof, and colistin or a pharmaceutically acceptable salt thereof; Apo6619 or a pharmaceutically acceptable salt thereof, and cefotaxine or a pharmaceutically acceptable salt thereof; and Apo6619 or a pharmaceutically acceptable salt thereof, and amikacin or a pharmaceutically acceptable salt thereof.

In some embodiments, when the bacterial infection is caused by *Pseudomonas aeruginosa* (PA), the iron chelator is deferiprone or a pharmaceutically acceptable salt thereof, and the antibiotic is consisting of rifampin, doxycycline, colistin, cefotaxine, pharmaceutically acceptable salts thereof, and combinations thereof. In other embodiments, when the bacterial infection is caused by *Escherichia coli* (EC), the antibiotic is rifampin or a pharmaceutically acceptable salt thereof, and the iron chelator is selected from the group consisting of Compound 4, VK28 or an analog or derivative thereof, deferiprone, Apo6619, triapine, pharmaceutically acceptable salts thereof, and combinations thereof.

Figure 43:
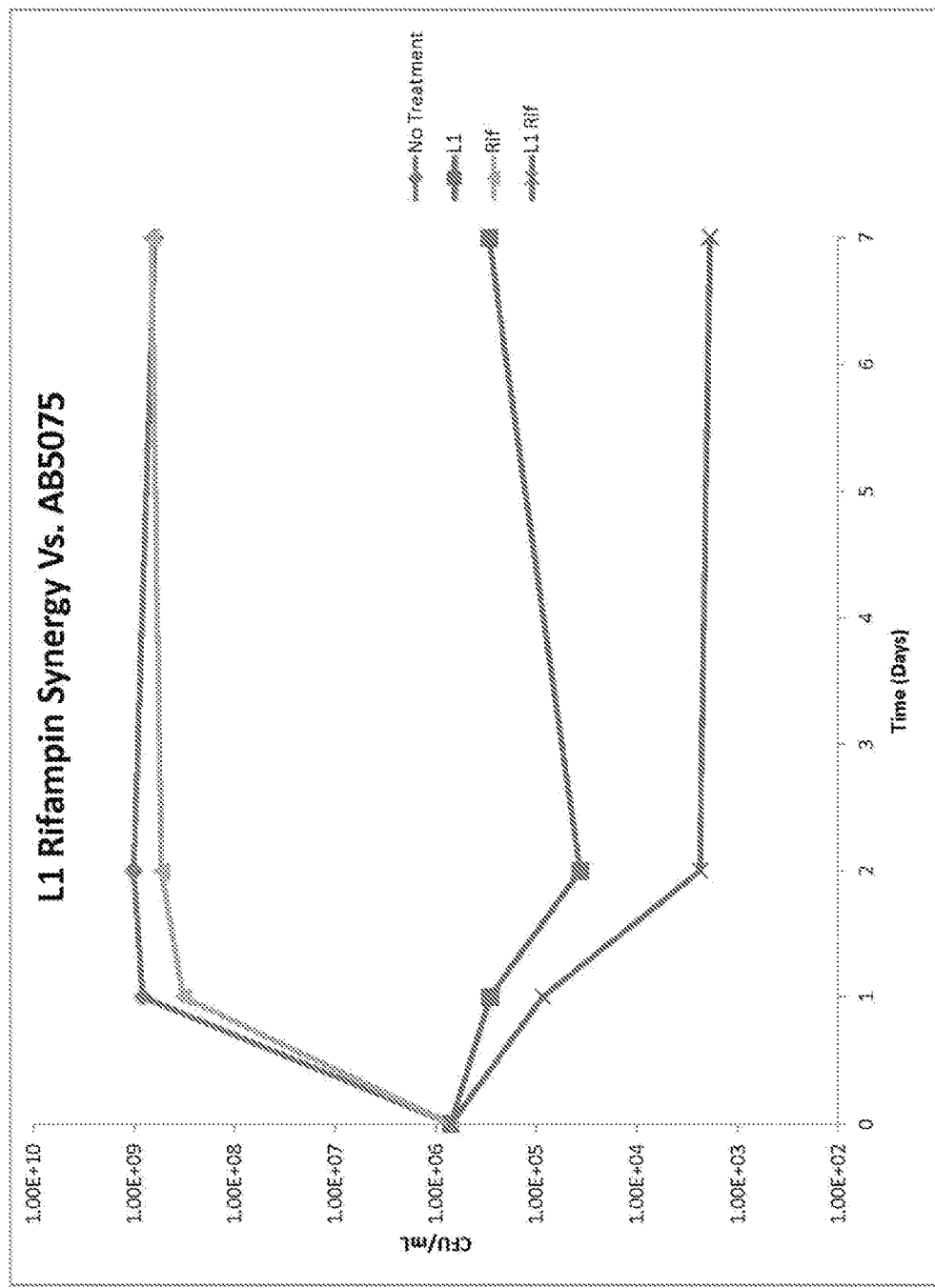
FIG. 43 is a kill-time assay that depicts that no rifampin resistance arises in the presence of an iron chelator over 7 day culturing *A. baumannii* strain AB5075.

Development of antibiotic-resistant strains is an ongoing problem in the treatment of bacterial infections. In some embodiments, the present technology provides methods and compositions for reducing, inhibiting or preventing formation of antibiotic-resistant bacterial strains. In some embodiments, the iron chelator of the present technology is administered to a patient as a prophylactic before antibiotic treatment or during antibiotic treatment. In some embodiments, the iron chelator is added concurrently with an antibiotic. The combination of iron chelator and an antibiotic prevents, inhibits or reduces the formation of antibiotic-resistance strains of the bacteria to the antibiotic being administered. For example, the addition of an iron chelator, ApoL1 with rifampin to cultures of AB5075, a stain of *A. baumannii* (Ab) that rapidly develops antibiotic resistance, as seen in FIG. 43, unexpectedly inhibits growth of an antibiotic resistant Ab strain over 7 days. Without the addition of an ApoL1, antibiotic-resistant strains of Ab develop in less than one day in the presence of rifampin alone.

In some embodiments, the present technology provides a method of providing an iron chelator to an established standard of care treatment of a bacterial infection. Methods are provided for supplementing or improving a process of treating or preventing a bacterial infection by administering a pharmaceutically acceptable iron chelator to the patient, wherein the process comprised administering one or more antibiotics. For example, the present technology can provide a method of providing an iron chelator in combination with an antibiotic approved for the treatment of a particular bacterial strain. For example, the standard of care for treating *M. tuberculosis* comprises administering rifampin, and methods are provided for supplementing or improving the standard of care for treating a bacterial infection, particularly a drug-resistant bacterial infection, by adding one or more pharmaceutically acceptable iron chelators. For example, in some embodiments, the iron chelator can be used in the treatment of *Mycobacterium tuberculosis* (*M. tuberculosis*). For *M. tuberculosis*, the standard of care is treatment with rifampin and isoniazid, and pyrazinamide. A problem in *M. tuberculosis* treatment is the formation of antibiotic resistant strains. Not to be bound by any theory, but addition of iron chelator to the standard of care for *M. tuberculosis* can provide treatment that may be increase the effectiveness of the antibiotic treatment. It can also be contemplated that the addition of an iron chelator to the treatment of *M. tuberculosis* may inhibit, prevent or delay the development of antibiotic resistant strains. Accordingly, methods are provided for preventing, reducing or inhibiting development of antibiotic resistant strains of bacteria by administering a pharmaceutically acceptable iron chelator that reduces biological availability of iron for one or more strains of bacteria, or a pharmaceutically acceptable salt thereof.

In some embodiments, methods of treating or preventing a bacterial infection are provided which comprise killing bacteria rather than preventing biofilm growth.

EXAMPLES

Example 1

This example shows that VK28 attenuates growth of a clinical isolate of *A. baumannii* AB5711 more effectively than other iron chelators in low iron media. *Acinetobacter baumannii* strain 5711 (AB5711) was grown overnight in LB media and sub-cultured into low iron media. The tested iron chelators were deferoxamine (DFO), deferiprone (DFP), 2,2-dipyridyl, and VK28. The iron chelators were added after 4 hr of growth.

Bacterial growth was estimated by absorption at $OD_{600}$ every 4 hr for 24 hr. Optical density (OD) at 600 nm ($OD_{600}$) as measured by a spectrophotometer is a widely used technique known by one skilled in the art to estimate the total number of bacterial cells present in a broth culture (CFU/ml). The exact amount of OD produced by a culture will depend on the concentration of cells present, the species and strain of microbe present, the growth conditions used, and the wavelength of the light being transmitted. Thus, the relationship between OD and cell concentrations will depend on the specific strain and growth conditions studied. For example, the $OD_{600}$ of 1 for *E. coli* is about $1 \times 10^9$ CFU/ml.

Figure 1B:
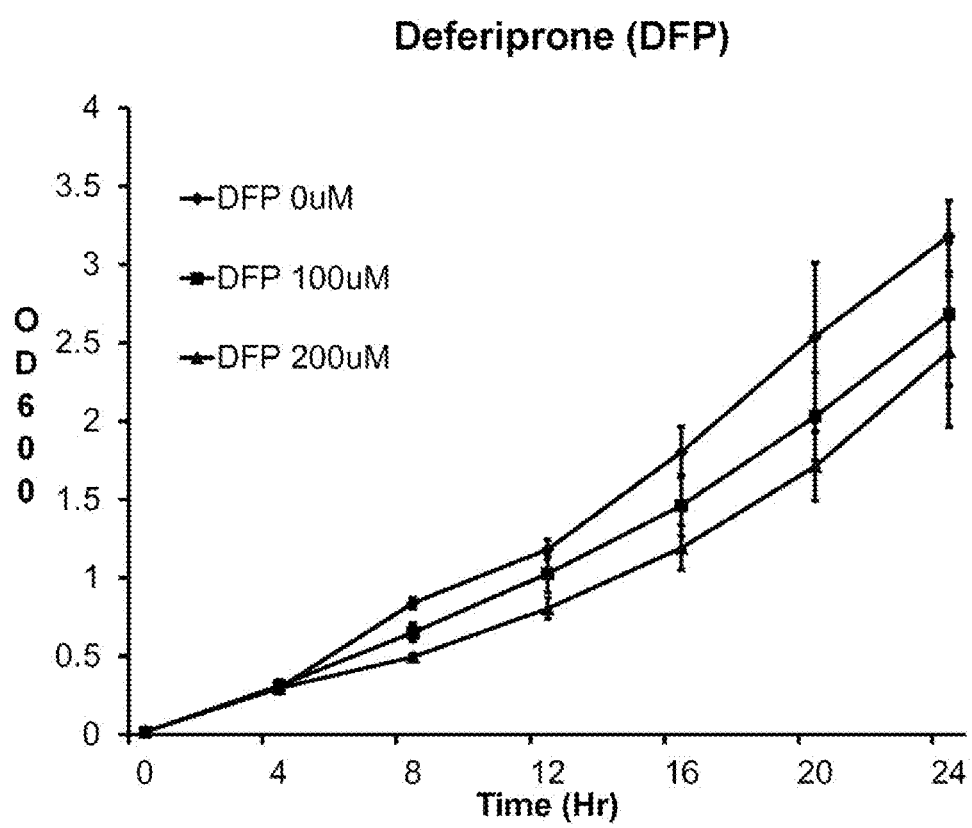
FIG. 1B shows the growth curves of AB5711 cultures treated with 0 μm DFP (♦), 100 μM DFP (■), or 200 μM DFP (▲).
Figure 1C:
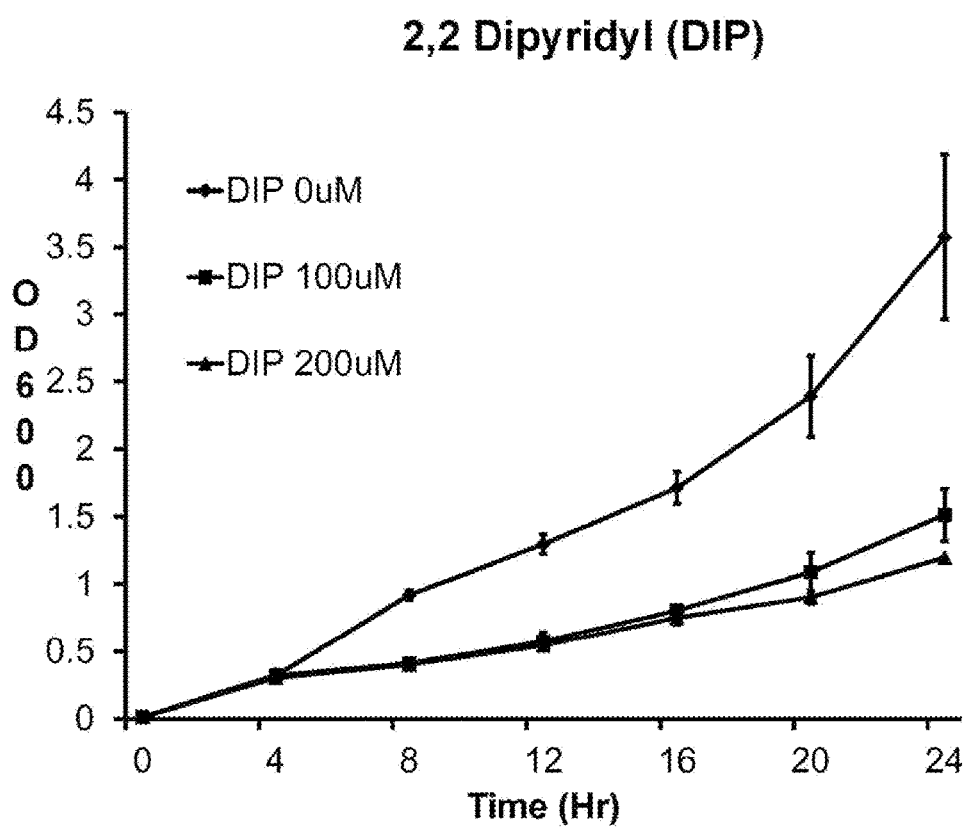
FIG. 1C shows the growth curves of AB5711 cultures treated with 0 μm DIP (♦), 100 μM DIP (■), or 200 μM DIP (▲).
Figure 1D:
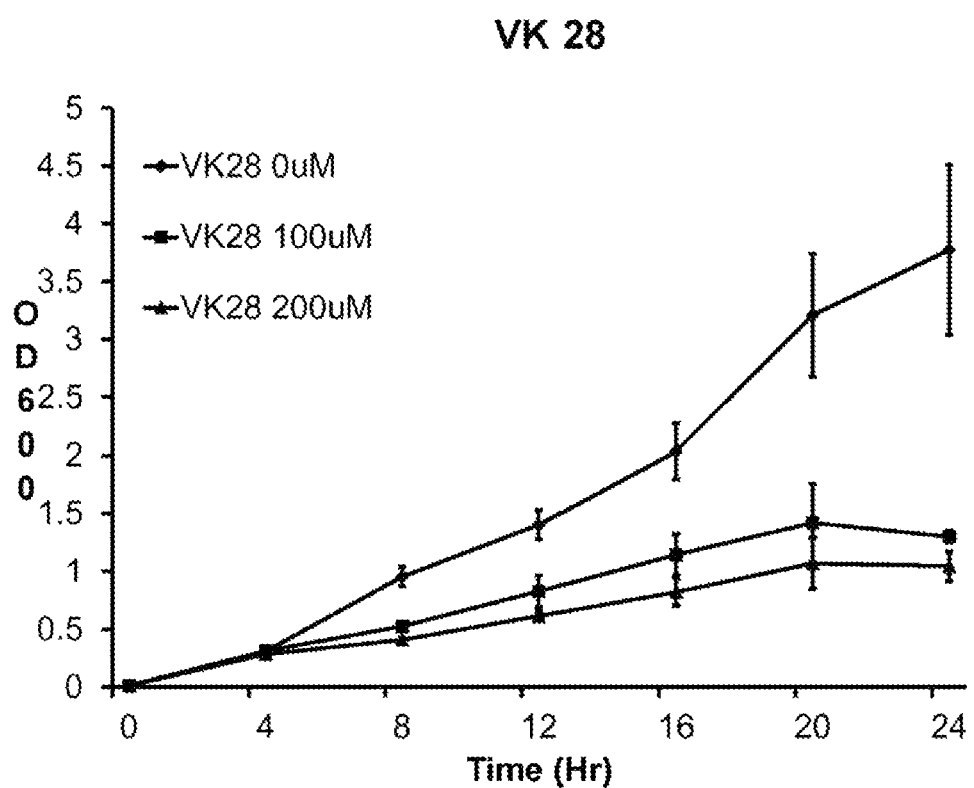
FIG. 1D shows the growth curves of AB5711 cultures treated with 0 μm VK28 (♦), 100 μM VK28 (■), or 200 μM VK28 (▲).

FIG. 1A shows the growth curves of AB5711 cultures treated with 0 μm DFO (♦), 100 μM DFO (■), or 200 μM DFO (▲). FIG. 1A shows that deferoxamine had little effect, particularly at a concentration of 100 μM. This is consistent with deferoxamine's function—as a siderophore. FIG. 1B shows the growth curves of AB5711 cultures treated with 0 μm DFP (♦), 100 μM DFP (■), or 200 μM DFP (▲). FIG. 1B shows that deferiprone (DFP) somewhat reduced bacterial growth. FIG. 1C shows the growth curves of AB5711 cultures treated with 0 μm DIP (♦), 100 μM DIP (■), or 200 μM DIP (▲). FIG. 1D shows the growth curves of AB5711 cultures treated with 0 μm VK28 (♦), 100 μM VK28 (■), or 200 μM VK28 (▲). FIGS. 1C and 1D show that 2,2 dipyridyl (DIP) and VK28, respectively, each reduced bacterial growth to a significant extent.

Example 2

This example studies bioluminescent *A. baumannii* challenged with iron chelators. AB0057 is a strain of *Acineto-* bacter baumannii available from Robert Bonomo, Case Western Reserve University, Cleveland, Ohio.

Figure 38:
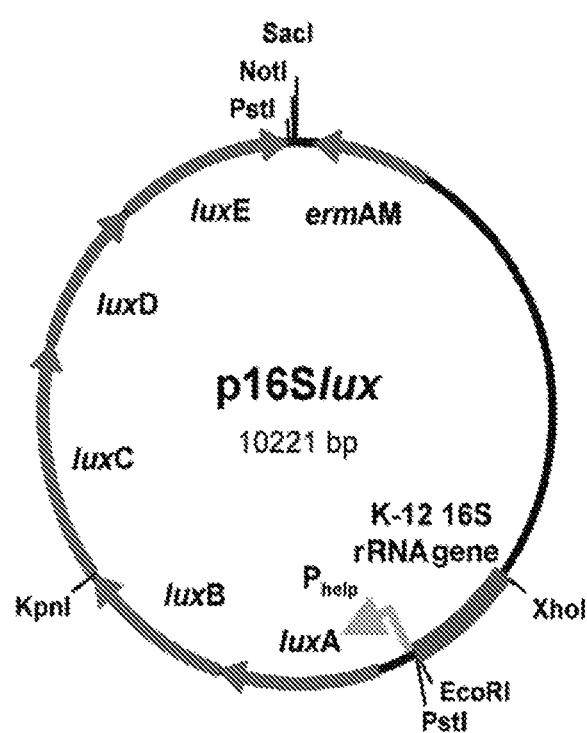
FIG. 38 illustrates the p16Slux plasmid.

As a precursor to conducting this in vitro assay, AB0057 was transformed with a bioluminescent plasmid. The p16Slux plasmid is illustrated in FIG. 38, and further details regarding its development and use are set forth in Christian U. Riedel et al., "Construction of p16Slux, a Novel Vector for Improved Bioluminescent Labeling of Gram-Negative Bacteria," Appl. Environ. Microbiol. 2007 November; 73(21): 7092-7095.

Figure 2:
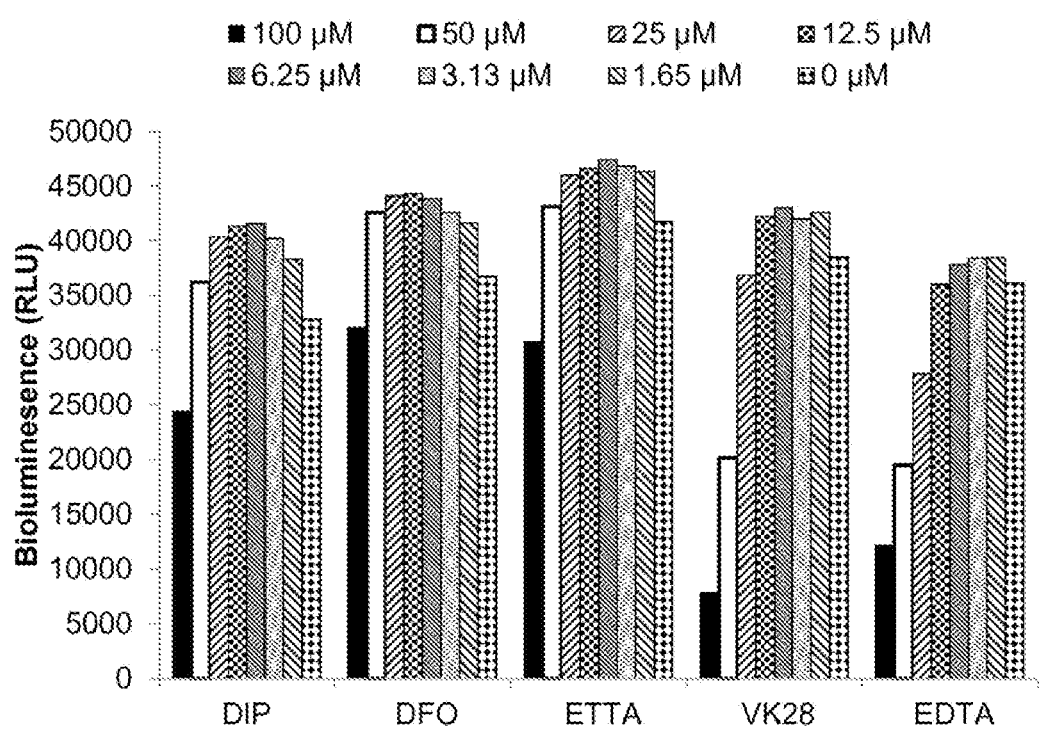
FIG. 2 shows the reduction in bioluminescent AB0057 (y-axis) in the presence of varying concentrations of the different iron chelators (x-axis).

Bioluminescent AB0057 were grown overnight in LB media and sub-cultured into low iron media in a 96-well plate containing varying concentrations of iron chelators for 4 hours. Bacterial growth was measured by bioluminescence (relative light units). The iron chelators VK28 and DFO were tested along with chelators DIP, ETTA, and EDTA as controls. The chelators were tested a concentrations of 0 μM, 1.65 μM, 3.13 μM, 6.25 μM, 12.5 μM, 25 μM, 50 μM, and 100 μM. FIG. 2 shows the reduction in bioluminescent AB0057 after 4_ hours in the presence of varying concentrations of the different iron chelators (x-axis). Bioluminescence (y-axis) was generally lower at higher concentrations of iron chelators, but especially surprisingly lower for VK28 at 100 μm. These results show that VK28 is an iron chelator that limits A. baumannii growth in low iron media, and it is more efficacious than other iron chelators.

Example 3

Figure 3:
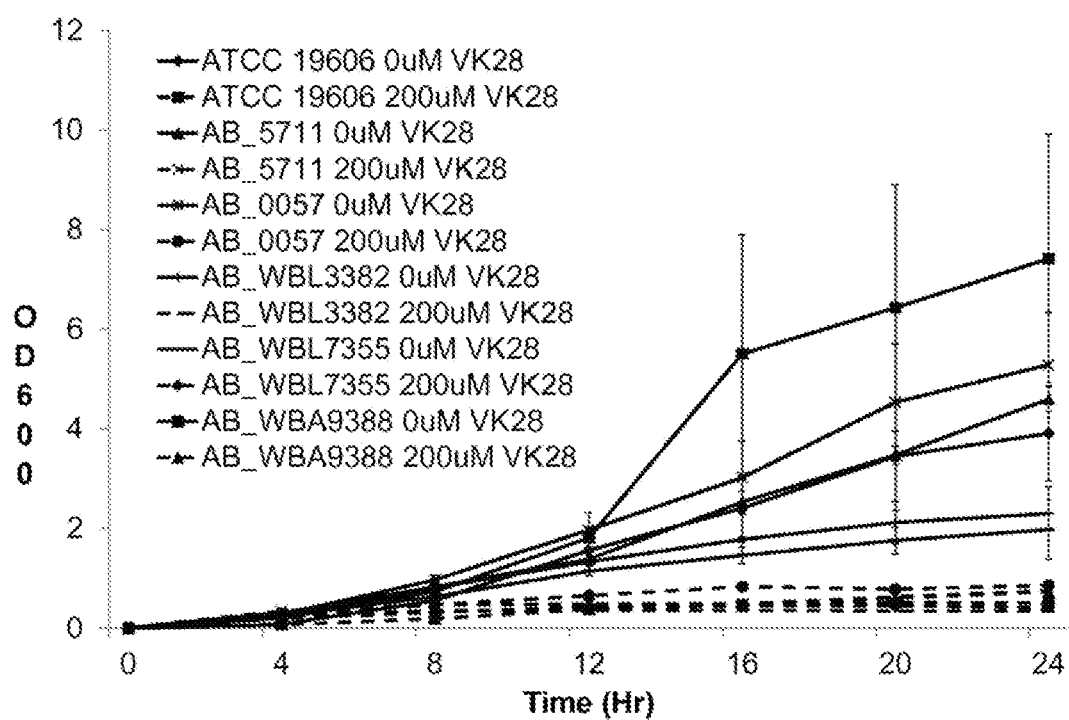
FIG. 3 is a graph demonstrating the growth curve of six clinical strains of *A. baumannii* (shown as $OD_{600}$ values) with no iron chelator or with 200 μM of VK28.

This example shows VK28 is effective against multiple strains of Acinetobacter baumannii. Five clinical isolates of A. baumannii were obtained from Walter Reed Army Medical Center (WRAMC) and compared to the laboratory strain AB19606 from the ATCC. Strains were challenged with either 0 μM or 200 μM VK28 in low-iron M9 media after 4 hr of growth. Growth was estimated by absorbance at 600 nm every 4 hr for 24 hr. Dashed lines represent the same strains treated with 200 μM VK28. FIG. 3 shows $OD_{600}$ values for the six strains of A. baumannii with no iron chelator or with 200 μM of VK28. VK28 greatly decreases the $OD_{600}$ values (dotted lines) indicating, that it effective at limiting the growth of multiple clinical isolates of A. baumannii, regardless of antibiotic resistance.

Example 4

This example provides further evidence that the removal of iron is responsible for bacterial growth inhibition. A. baumannii isolate 5711 was grown in low iron M9 media supplemented with 0 μM, 10 μM, or 100 μM $FeCl_3$ with and without the addition of 200 μM VK28 following 4 hr of growth. Growth was estimated by absorbance at 600 nm every 4 hr for 24 hr.

Figure 4:
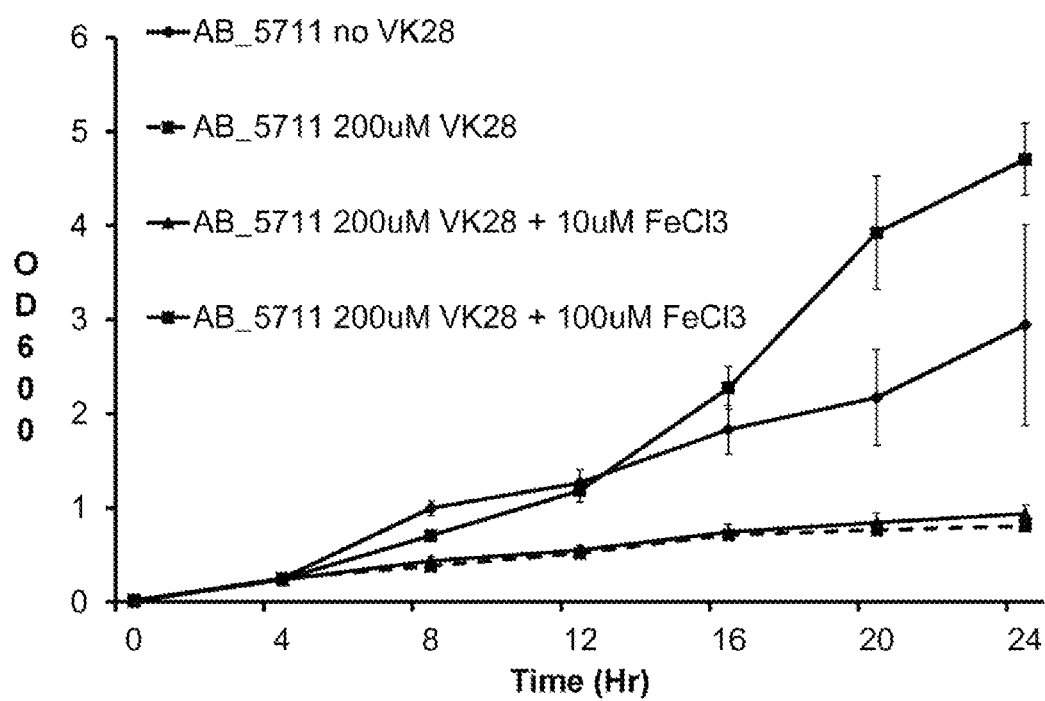
FIG. 4 shows the growth curves of AB 5711 grown with no VK28 (♦), with 200 μM VK28 (■), with 200 μM VK28 and 10 μM $FeCl_3$ (▲), and with 200 μM VK28 and 100 μM $FeCl_3$ (-♦-).

FIG. 4 shows the growth curves of AB 5711 grown with no VK28 (♦), with 200 μM VK28 (■), with 200 μM VK28 and 10 μM $FeCl_3$ (▲), and with 200 μM VK28 and 100 μM $FeCl_3$ (-■-) These results demonstrate that when free iron is added back into the medium, bacteria are rescued from the VK28 growth inhibition. These results suggest that iron chelation is responsible bacteriostatic activity.

Example 5

This example further demonstrates the bacteriostatic activity of VK28. A. baumannii was grown in low-iron M9 media and challenged with 200 μM VK28 at 0 hr (■), 4 hr (▲), 8 hr (■), 12 hr (■), 16 hr (•), and 20 hr (■) post-inoculation. Growth was estimated by absorbance at 600 nm every 4 hr for 24 hr.

Figure 5:
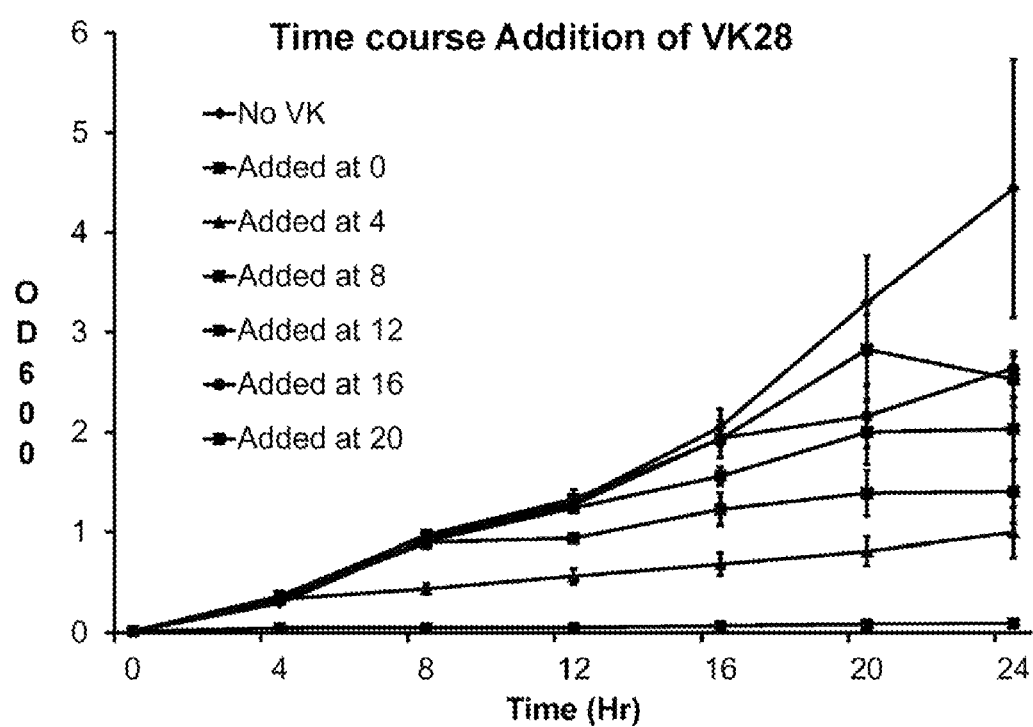
FIG. 5 shows the growth curves of *A. baumannii* grown in low-iron M9 media and challenged with 200 μM VK28 at 0 hr (■), 4 hr (▲), 8 hr (■), 12 hr (■), 16 hr (•), and 20 hr (■) post-inoculation.

FIG. 5 shows the results and demonstrates that the addition of VK28 at different times after initial infection is effective to halt the continued multiplication of bacteria.

Example 6

This example shows that VK28 is an effective in vitro growth inhibitor to multiple species of MDR-bacteria. Isolates of Extended Spectrum Beta-Lactamase (ESBL) Escherichia coli, Klebsiella pneumoniae, Pseudomonas aeruginosa, and Methicillin-Resistant Staphylococcus aureus (MRSA) were challenged with either 0 μM, 100 μM or 200 μM VK28 in low-iron M9 media after 4 hr of growth. Growth was estimated by absorbance at 600 nm at 24 hr post inoculation.

Figure 6:
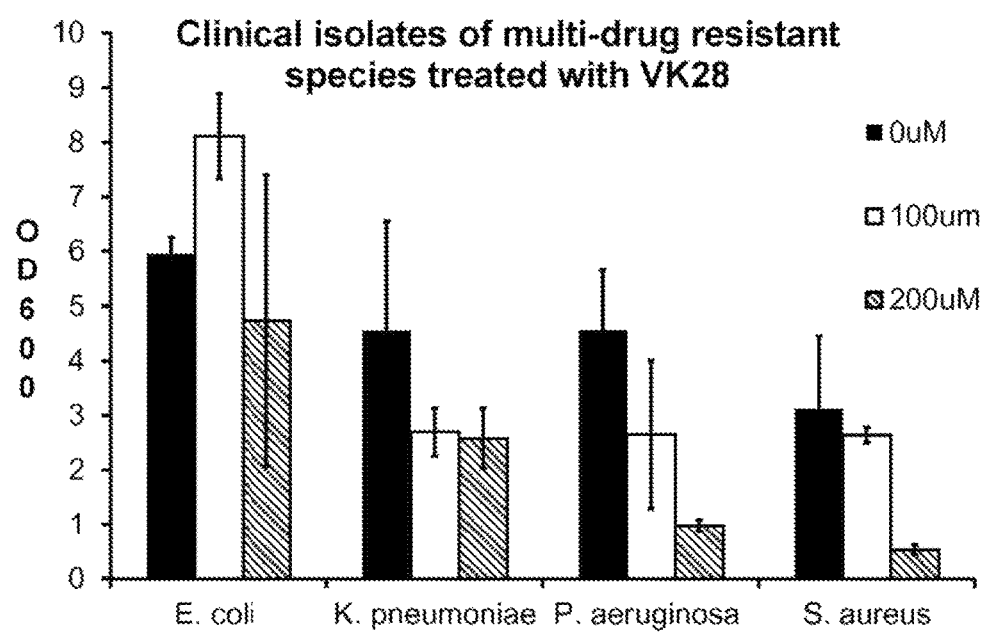
FIG. 6 shows the $OD_{600}$ (growth) for all four bacterial species after challenge with either 0 μM (black bar), 100 μM (white bar) or 200 μM (stripe bar) VK28 at 24 hours post inoculation.

FIG. 6 shows the $OD_{600}$ for all four bacterial species after challenge with either 0 μM (black bar), 100 μM (white bar) or 200 μM (stripe bar) VK28 at 24 hours post inoculation. These results demonstrate that growth of all four bacterial strains was reduced by the addition of 200 μM VK28. In particular, the $OD_{600}$ of P. aeruginosa was significantly reduced by the addition of 200 μM VK28 (stripe bar), and the $OD_{600}$ of MRSA was significantly reduced by the addition of VK28 at concentrations of both 100 μM (white bar) and 200 μM (stripe bar). These results demonstrate that VK28 is efficacious against other multi-drug resistant bacteria such as MRSA, Klebsiella, and Pseudomonas.

Example 7

This example shows that VK28 works in synergy with tetracycline against A. baumannii. Tetracycline-resistant A. baumannii was grown in low-iron M9 media and challenged with 400 μM Vk28, 16 ug/mL tetracycline (Tet16), or in a combination of VK28 and antibiotic at the same concentrations.

Figure 7:
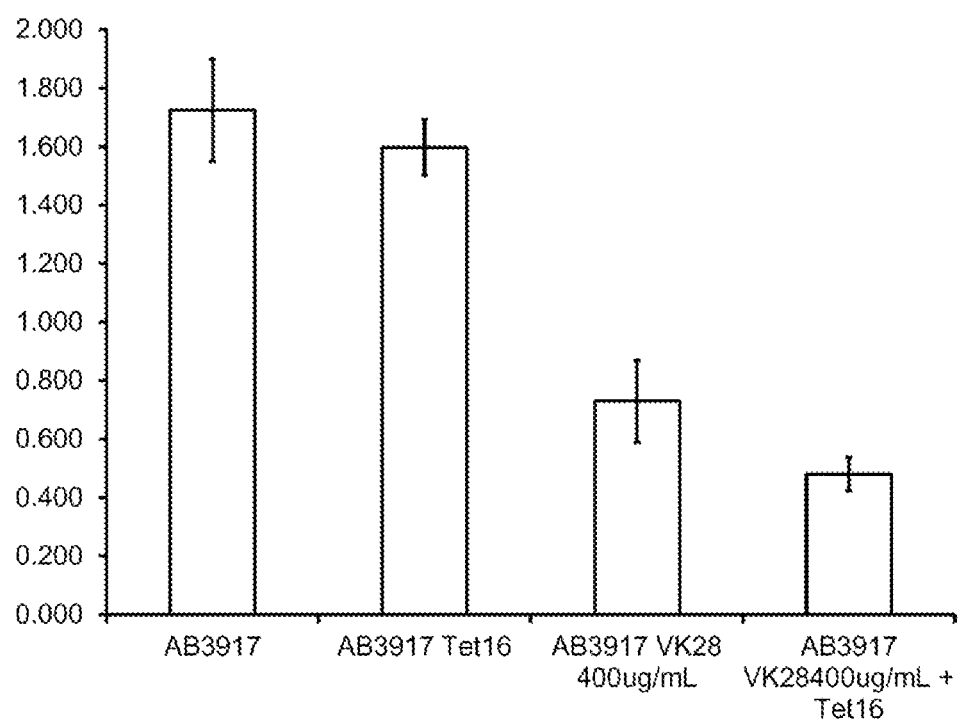
FIG. 7 is a bar graph that synergic growth inhibition of iron chelators with tetracycline against tetracycline-resistant *A. baumannii*.

FIG. 7 shows the results. Growth was estimated by absorbance at 600 nm at 24 hr. (y-axis). The administration of tetracycline alone resulted in little reduction of bacteria, while the addition of VK28 resulted in a significant reduction in bacteria. VK28 works in synergy with tetracycline against A. baumannii regardless of the presence of a Tet resistance gene. When tetracycline and VK28 were administered together, the reduction in bacteria was greater than the added reductions from separate administration of tetracycline and VK28. This indicates that tetracycline and VK28 acted synergistically in reducing tetracycline-resistant A. baumannii. These results are suggestive that VK28 could re-sensitize bacteria to first generation antibiotics.

Example 8

The minimal inhibitory concentration (MIC) of non-toxic iron chelators was determined against standard strains of MDR bacteria and clinical isolates according to the guidelines of the Clinical and Laboratory Standards Institute (CLSI).

Individual MICs were determined following the microdilution method recommended by CLSI in cationic-adjusted Mueller-Hinton Broth (CAMHB), or M9 media. The MIC was defined as the lowest drug concentration that caused 100% inhibition of visible bacterial growth after 24 hours incubation. Tests were performed in triplicate. MIC of iron chelators were determined for noscomial ESKAPE pathogens. Table 1 shows the results for a number of bacterial strains including AB19606, SA43300, BAA-2146, PA PAO1, and EC35718 and indicates that the pharmaceutically acceptable iron chelators ApoL1, Apo6619, and VK28 were effective at useful concentrations in inhibiting one or more strains of multi-drug resistant bacteria.

TABLE 1

| Bacterial Strain | MIC of Iron Chelators (ug/mL) | | | | |
|---|---|---|---|---|---|
| | DIP | DFO | ApoL1 | Apo6619 | VK28 |
| 17978 | 64 | >500 | 125 | 250 | 125 |
| 19606 | 64 | >500 | 125 | 250 | 125 |
| 25923 | 500 | >500 | >500 | >500 | 250 |
| 43300 | 250 | >500 | >500 | >500 | 250 |
| PAO1 | 250 | >500 | 250 | >500 | >500 |
| 27853 | 250 | >500 | >500 | >500 | >500 |
| BAA-2146 | 250 | >500 | 250 | >500 | >500 |
| 700603 | 500 | >500 | 500 | >500 | >500 |
| 35218 | 64 | >500 | 500 | 250 | >500 |
| 43888 | 64 | >500 | 500 | 250 | >500 |

In Tables 1 and 2, "17978" is ATCC 17978: *Acinetobacter baumannii*; "19606" is ATCC 19606: *A. baumannii*; "25923" is ATCC 25923: *S. aureus*; "43300" is ATCC 43300: *S. aureus* (MRSA); "PAO1" is *P. aeruginosa* PAO1; "27853" is ATCC 27853: *P. aeruginosa*; "BAA-2146" is BAA 2146 *K. pneumonia*; "700603" is ATCC 700603: *K. pneumonia*; "35218" is ATCC 35218: *E. coli*; and "43888" is ATCC 43888: *E. coli* 0157:H7. Similar assays indicated that ApoL1 has an MIC against WBA 2090 *E. faecilium* of 600-700 ug/mL.

Table 2 shows the MIC of iron chelators against clinical isolates of *A. baumannii, Staphylococcus aureus, Escherichia coli, Pseudomonas aeruginosa*, and *Klebsiella pneumoniae* as determined in RPMI1640 media. This media is closer to the iron levels in the human body. MICs are in ug/mL.

TABLE 2

| Bacterial Strain | MIC of Iron Chelators (ug/mL) | | | | |
|---|---|---|---|---|---|
| | DIP | DFO | ApoL1 | Apo6619 | VK28 |
| 17978 | 32 | >500 | 64 | 64 | 32 |
| 19606 | 32 | >500 | 125 | 125 | 8 |
| 25923 | — | — | — | — | 32 |
| 43300 | — | — | — | — | 16 |
| PAO1 | 250 | >500 | 125 | 500 | 16 |
| 27853 | 250 | >500 | 500 | >500 | 16 |
| BAA-2146 | 125 | >500 | 250 | 500 | 16 |
| 700603 | 250 | >500 | 250 | 500 | 16 |
| 35718 | 64 | >500 | 500 | 250 | 32 |
| 43888 | 64 | >500 | 250 | 250 | 8 |

The MIC of VK28 and deferiprone (DFP) ranged from 100-500 µg/mL for *Staphylococcus aureus, Acinetobacter baumannii, Escherichia coli, Pseudomonas aeruginosa*, and *Klebsiella pneumoniae*. The other chelators tested were significantly higher (>700 µg/mL). When using media that better represents iron levels in the human body, the MIC improved 2 to 4-fold for VK28 and deferiprone.

Table 3 shows the MIC of iron chelators determined for clinical isolates of bacterial strains of *A. baumannii* in CAMHB media as described above.

TABLE 3

| Bacterial Strain | MIC of Iron Chelators (µg/ml) | | | |
|---|---|---|---|---|
| | Compound 4 | VK28 | ApoL1 | Apo6619 |
| AB967 | 500 | 250 | 250 | 250 |
| AB2828 | 500 | 250 | 500 | 500 |
| AB3340 | 500 | 250 | 250 | 250 |
| AB3560 | 500 | 250 | 500 | 500 |
| AB3638 | 500 | 250 | 250 | 500 |
| AB3785 | 500 | 250 | 250 | 500 |
| AB3806 | 1000 | 500 | 500 | 1000 |
| AB3917 | 500 | 500 | 250 | 500 |
| AB3927 | 500 | 250 | 250 | 250 |
| AB4025 | 500 | 250 | 250 | 500 |
| AB4026 | 500 | 250 | 250 | 500 |
| AB4027 | 500 | 250 | 250 | 500 |
| AB4052 | 1000 | 500 | 250 | 500 |
| AB4269 | 500 | 250 | 250 | 250 |
| AB4448 | 500 | 250 | 250 | 500 |
| AB4456 | 500 | 250 | 250 | 500 |
| AB4490 | 500 | 250 | 250 | 500 |
| AB4498 | 500 | 500 | 250 | 500 |
| AB4795 | 500 | 250 | 250 | 500 |
| AB4857 | 500 | 500 | 250 | 500 |
| AB4878 | 500 | 500 | 250 | 500 |
| AB4932 | 500 | 500 | 500 | 500 |
| AB4957 | 500 | 500 | 125 | 250 |
| AB4991 | 500 | 250 | 250 | 500 |
| AB5001 | 500 | 250 | 125 | 250 |
| AB5075 | 500 | 250 | 250 | 250 |
| AB5197 | 500 | 250 | 250 | 500 |
| AB5256 | 500 | 250 | 250 | 250 |
| AB5674 | 500 | 250 | 250 | 250 |
| AB5711 | 500 | 250 | 250 | 250 |

Table 4 shows the MIC of iron chelators determined for clinical isolates of bacterial strains of *A. baumannii, Staphylococcus aureus, Escherichia coli, Pseudomonas aeruginosa*, and *Klebsiella pneumoniae* in RPMI (low iron) media as described above.

TABLE 4

| Bacterial Strain | MIC of Iron Chelators (µg/ml) | | | |
|---|---|---|---|---|
| | Compound 4 | VK28 | ApoL1 | Apo6619 |
| AB967 | NG | NG | NG | NG |
| AB2828 | NG | NG | NG | NG |
| AB3340 | NG | NG | NG | NG |
| AB3560 | NG | NG | NG | NG |
| AB3638 | 64 | 8 | 125 | 250 |
| AB3785 | 32 | 8 | NG | 125 |
| AB3806 | 32 | 8 | 125 | 250 |
| AB3917 | 32 | 4 | NG | 250 |
| AB3927 | NG | NG | NG | NG |
| AB4025 | 32 | 8 | 125 | 250 |
| AB4026 | 32 | 8 | 125 | 250 |
| AB4027 | 32 | 8 | 125 | 250 |
| AB4052 | 64 | 8 | 125 | 250 |
| AB4269 | 32 | 8 | 125 | 125 |
| AB4448 | 64 | 8 | 125 | 250 |
| AB4456 | 32 | 8 | 125 | 250 |
| AB4490 | 32 | 8 | 125 | 250 |
| AB4498 | 64 | 8 | 125 | 250 |
| AB4795 | 32 | 4 | 125 | 250 |
| AB4857 | 64 | 8 | 125 | 250 |
| AB4878 | 64 | 8 | 250 | 250 |
| AB4932 | 125 | 8 | 64 | 250 |
| AB4957 | 125 | 8 | 125 | 250 |
| AB4991 | 8 | 8 | 125 | 125 |
| AB5001 | 32 | 8 | 125 | 250 |
| AB5075 | 64 | 8 | 125 | 250 |

TABLE 4-continued

| Bacterial | MIC of Iron Chelators (µg/ml) | | | |
|---|---|---|---|---|
| Strain | Compound 4 | VK28 | ApoL1 | Apo6619 |
| AB5197 | 32 | 4 | 125 | 250 |
| AB5256 | 125 | 8 | 125 | 250 |
| AB5674 | 32 | 8 | 125 | 250 |
| AB5711 | 64 | 8 | 64 | 250 |

NG = no growth in table 4.

Table 4 demonstrates bacteria grown in media containing iron levels similar to the human body (low iron RPMI). The MIC for many clinical isolates of bacterial strains is greatly reduced as compared with iron containing media. For a number of strains, the iron chelators produced no growth of bacteria (NG).

Table 5 demonstrates MIC for additional bacterial strain isolates of *A. baumannii* for bacteria grown in both higher iron containing media (CAMHB) and low iron M9 media.

TABLE 5

| CAMHB | | | M9 | |
|---|---|---|---|---|
| MIC DFP | MIC VK | Strain | DFP | VK28 |
| 150 >> 175 | 150 >> 200 | AB5711 | 50 << 100 | 25 << 50 |
| 150 >> 175 | 150 >> 200 | AB4456 | No Growth | No Growth |
| 150 >>175 | 150 >> 200 | AB4289 | 50 << 100 | 25 << 50 |
| 100 >>150 | 150 >> 200 | AB3627 | 50 << 100 | 12.5 << 25 |
| 150 >>175 | 250 >> 300 | AB0057 | 0 << 25 | 12.5 << 25 |
| 100 >> 150 | 150 >> 200 | AB4878 | 50 << 100 | 25 << 50 |
| 150 >> 175 | 150 >> 200 | 5256 | 50 << 100 | 12.5 << 25 |
| 100 >> 150 | 150 >> 200 | 5075 | 50 << 100 | 25 << 50 |
| 100 >> 150 | 150 >> 200 | 4991 | 50 << 100 | 25 << 50 |
| 150 >> 175 | 150 >> 200 | 4795 | 50 << 100 | 25 << 50 |
| 100 >> 150 | 200 >> 250 | 4932 | 50 << 100 | 25 << 50 |
| 175 >> 200 | 200 >> 250 | 4857 | No Growth | No Growth |
| 150 >> 175 | 200 >> 250 | 4490 | No Growth | No Growth |
| 150 >> 175 | 150 >> 200 | 3806 | 50 << 100 | 25 << 50 |
| 150 >> 175 | 150 >> 200 | 3560 | No Growth | No Growth |

This example demonstrates the MIC of the iron chelator Triapine for a number of bacteria strains. MIC were determined in CAMHB media as described above in Example 8. Table 6 shows the results of a number of bacteria strains, including *E. coli* EC35218 and EC43888, *P. aeruginosa* PA27853, *S. aureus* 43300, *A. baumannii* AB19606, and *K. pneumonia* KP700603.

TABLE 6

| | MIC (ug/mL) |
|---|---|
| PA27853 | 250 |
| EC35218 | 125 |
| EC43888 | 125 |
| AB19606 | 32 |
| KP700603 | 250 |
| SA43300 | 125 |

Example 9

Reductions in colony forming units (CFU)/mL were determined over time (time-kill assay) after exposure to VK28 and deferiprone (DFP), the two iron chelators that performed best in MIC assays when compared to controls. To better represent the iron content found in the human body, MIC and time-kill assays were also determined in minimal media and tissue culture media. Time-Kill assays were performed as previously described in G. P. Neupane et al., "In vitro time-kill activities of ciprofloxacin alone and in combination with the iron chelator deferasirox against *Vibrio vulnificus*," European Journal of Clinical Microbiology and Infectious Diseases, 407-410 (2010); and R. L. White, et al., "Comparison of Three Different In Vitro Methods of Detecting synergy: Time-Kill, Checkerboard, and E test," Journal of Antimicrobial Agents and Chemotherapy, 1914-1918 (1996). Initial inocula, for example $1\times10^6$ CFU/mL or $1\times10^7$ CFU/mL were challenged with iron chelator with and/or without an antibiotic. Cells were allowed to grow in CAMHB at 37° C. for 24 hours. Time-kill results were analyzed by determining the change in log 10 numbers of CFU/ml at 0, 6, and 24 h, compared to counts at 0 h. Antimicrobials were considered bactericidal at the lowest concentration that reduced the size of the original inoculum by >3 log 10 CFU/ml (99.9%) over each of the time periods and were considered bacteriostatic if the inoculum's size was reduced by 0 to <3 log 10 CFU/ml.

Figure 8A:
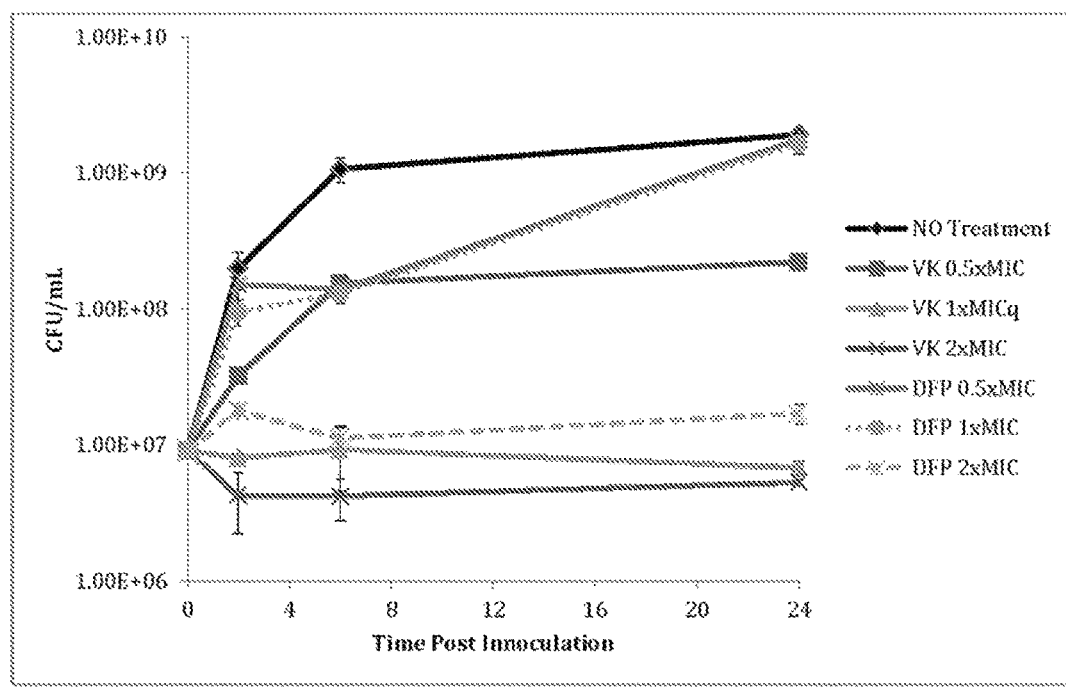
FIG. 8A shows the results of a time-kill assay of VK28(VK) or Deferiprone (DFP) against AB5075 a MDR-clinical isolate of *A. baumannii* in CAMHB.

FIG. 8A shows the results of a time-kill assay of VK28 (VK) or Deferiprone (DFP) against AB5075 a MDR-clinical isolate of *A. baumannii* in CAMHB. The untreated sample (♦) had about $1\times10^9$ CFU/mL after 6 and 24 hours. The sample treated with VK28 at 0.5 MIC (■) had an initial decrease in CFU/mL at 2 and 6 hours, but rebounded to about $1\times10^9$ CFU/mL at 24 hours. The sample treated with VK28 at 1×MIC (▲) did not increase in CFU over the 24 hour period, demonstrating a bacteriostatic effect for VK28. The sample treated with a VK28 at 2×MIC (X) had a decrease in CFU/mL after 2 hours that was sustained through the 24 hour period. Sample treated with DFP at 0.5×MIC (✖) and DFP at 1×MIC (-•-) had a reduced level of CFU/ml at 2 and 6 hours but did increase in CFU at 24 hours to levels as seen in the untreated sample. The sample treated with DFP at 2×MIC (-✖-), showed a decreased CFU/ml did not have a substantial increase in CFU/ml over the 24 hour period.

Figure 8B:
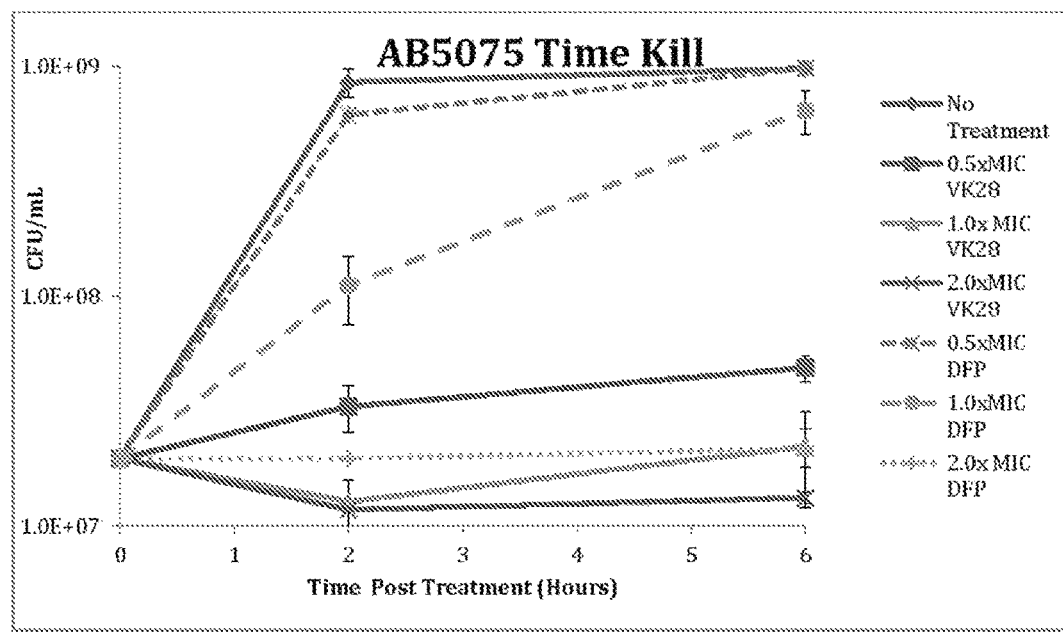
FIG. 8B shows the results of a time-kill assay of VK28(VK) or Deferiprone (DFP) against AB5075 in M9 minimal media over 24 hours.

FIG. 8B shows the results of a time-kill assay of VK28 (VK) or Deferiprone (DFP) against AB5075 in M9 minimal media over 24 hours. The untreated sample (♦) had greater than $1\times10^9$ CFU/mL after 9 hours that was sustained at 24 hours. The sample treated with VK28 at 0.5 MIC (■), VK28 at 1×MIC (▲), and VK28 at 2×MIC (x) had a slight inhibitory effect on the CFU/ml over the 24 hours. The sample treated with DFP at 0.5×MIC (•) and DFP at 1×MIC (+) had a slight reduction in CFU/ml levels over the 24 hour period. The sample treated with DFP at 2×MIC (-|-), showed a sustained level of CFU/ml obtained over the 24 hour period, demonstrating a bacteriostatic effect of DFP.

Example 10

In this example, time-kill assays were performed as described in Example 9 against different multi-drug resistant bacteria, namely *E. coli* and MRSA.

Figure 9A:
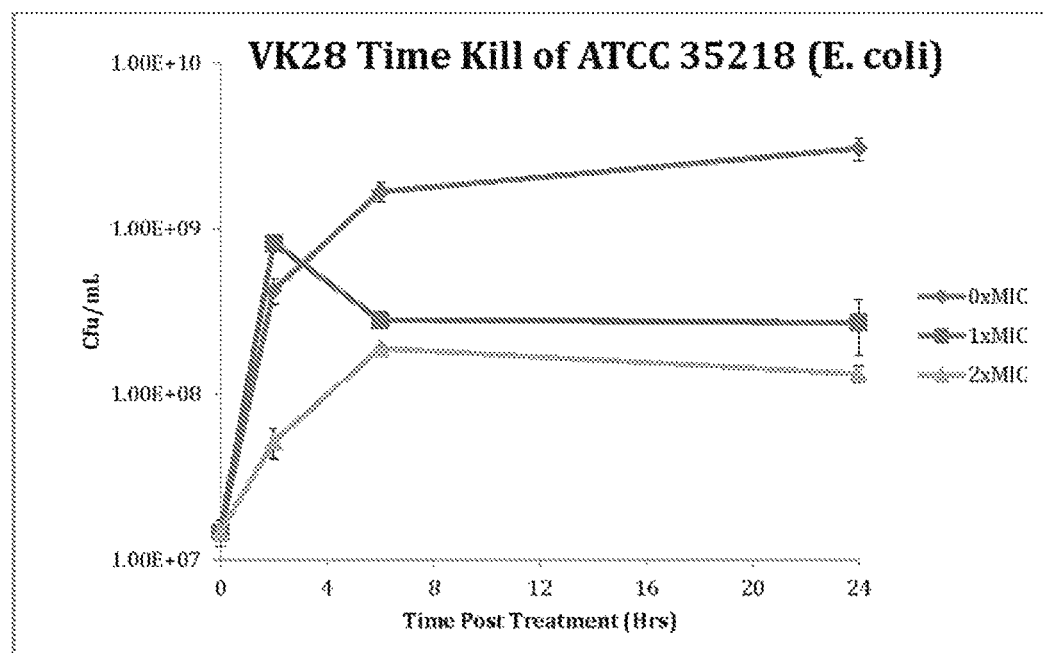
FIG. 9A shows the results of a time-kill assay of VK28 against *E. coli* EC35218 in CAMHB.

FIG. 9A shows the results of a time-kill assay of VK28 against *E. coli* EC35218 in CAMHB. The growth curve samples of treated with no VK28 (♦), 1×MIC VK28 (■), or 2×MIC VK28 (▲) demonstrate that 1×MIC and 2×MIC levels of VK28 decrease the growth of EC35218, demonstrating a bacteriostatic effect.

Figure 9B:
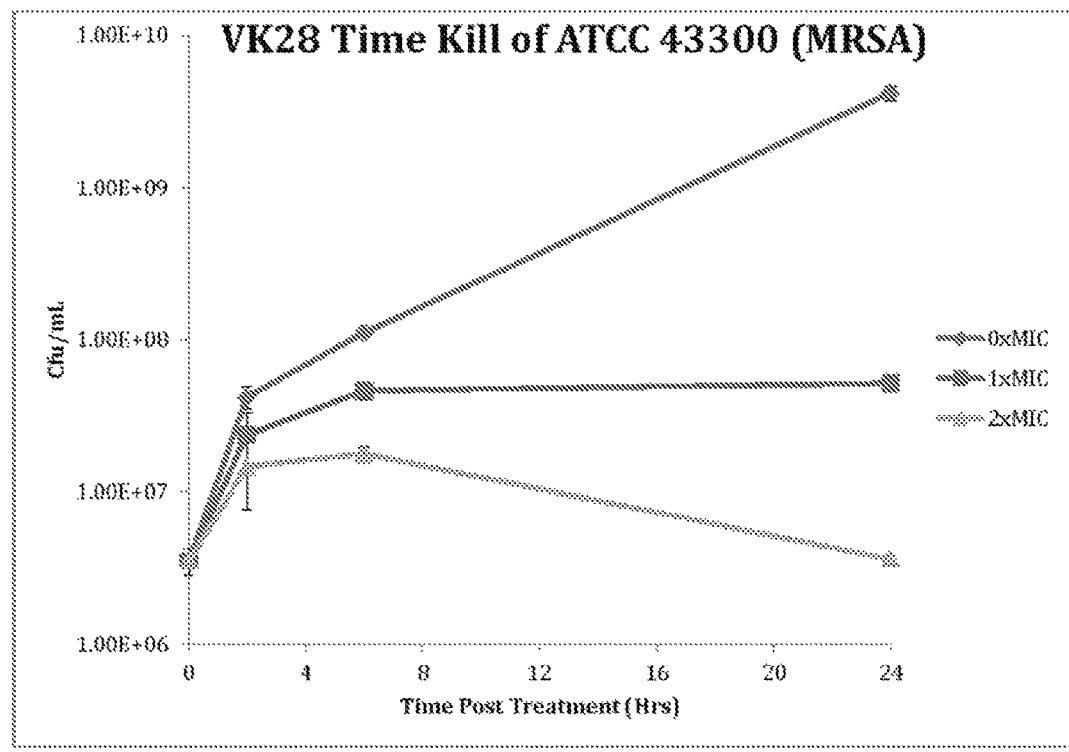
FIG. 9B shows the results of a time-kill assay of VK28 against MRSA ATCC SA43300 in CAMHB.

FIG. 9B shows the results of a time-kill assay of VK28 against MRSA ATCC SA43300 in CAMHB. The growth curve samples of treated with no VK28 (♦), 1×MIC VK28

(■), or 2×MIC VK28 (▲) demonstrate that 1×MIC and 2×MIC levels of VK28 decrease the growth of MRSA, demonstrating a bacteriostatic effect.

Example 11

In this example, time-kill assays were performed as described in Example 9 using ApoL1 as the iron chelator against two different E. coli strains. The initial inocula was 1×10^6 CFU/mL, and were challenged with ¾MIC Rifampicin and 1.5 MIC Iron Chelator alone and in combination. Time-kill results were analyzed by determining the change in log 10 numbers of CFU/mL at 6 and 24 hours.

Figure 10A:
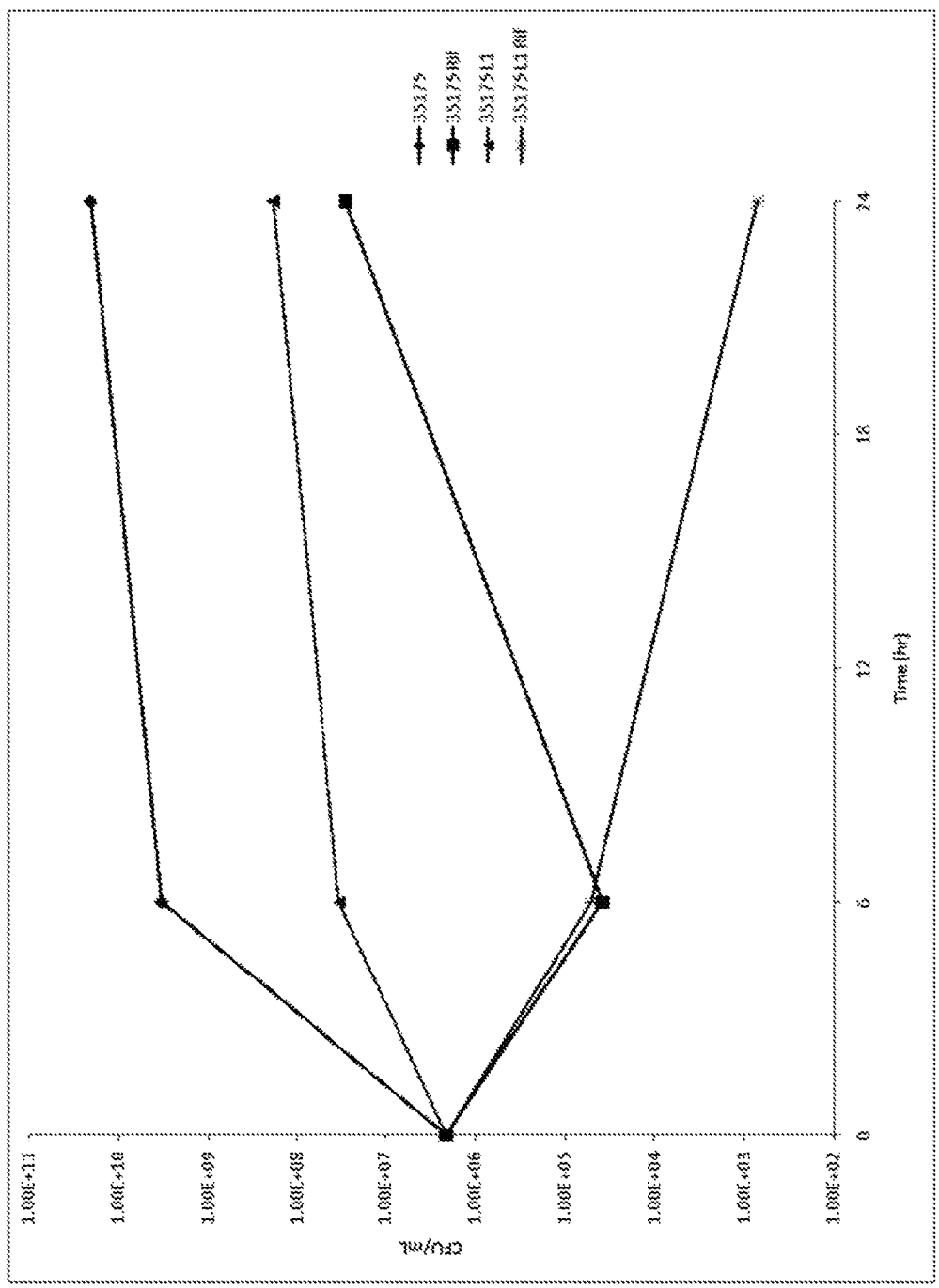
FIG. 10A shows the results of a time-kill assay of ApoL1 with and without rifampin against *E. coli* EC35218 in CAMHB.

FIG. 10A shows the results of a time-kill assay of ApoL1 with and without rifampin against E. coli EC35218 in CAMHB. The untreated sample (♦) had 1×10^9 CFU/mL after 6 and 24 hours. The sample treated with rifampin (■) had an initial decrease in CFU/mL at 6 hours, but rebounded to about 1×10^7 CFU/mL at 24 hours. The sample treated with ApoL1 (▲) had a slower increase in CFUs, indicating a bacteriostatic effect for ApoL1. The sample treated with a combination of ApoL1 and rifampin (✕) had a surprisingly large decrease in CFU/mL, a reduction greater than 3 log 10, indicating synergistic effect of the two agents and bactericidal effect.

Figure 10B:
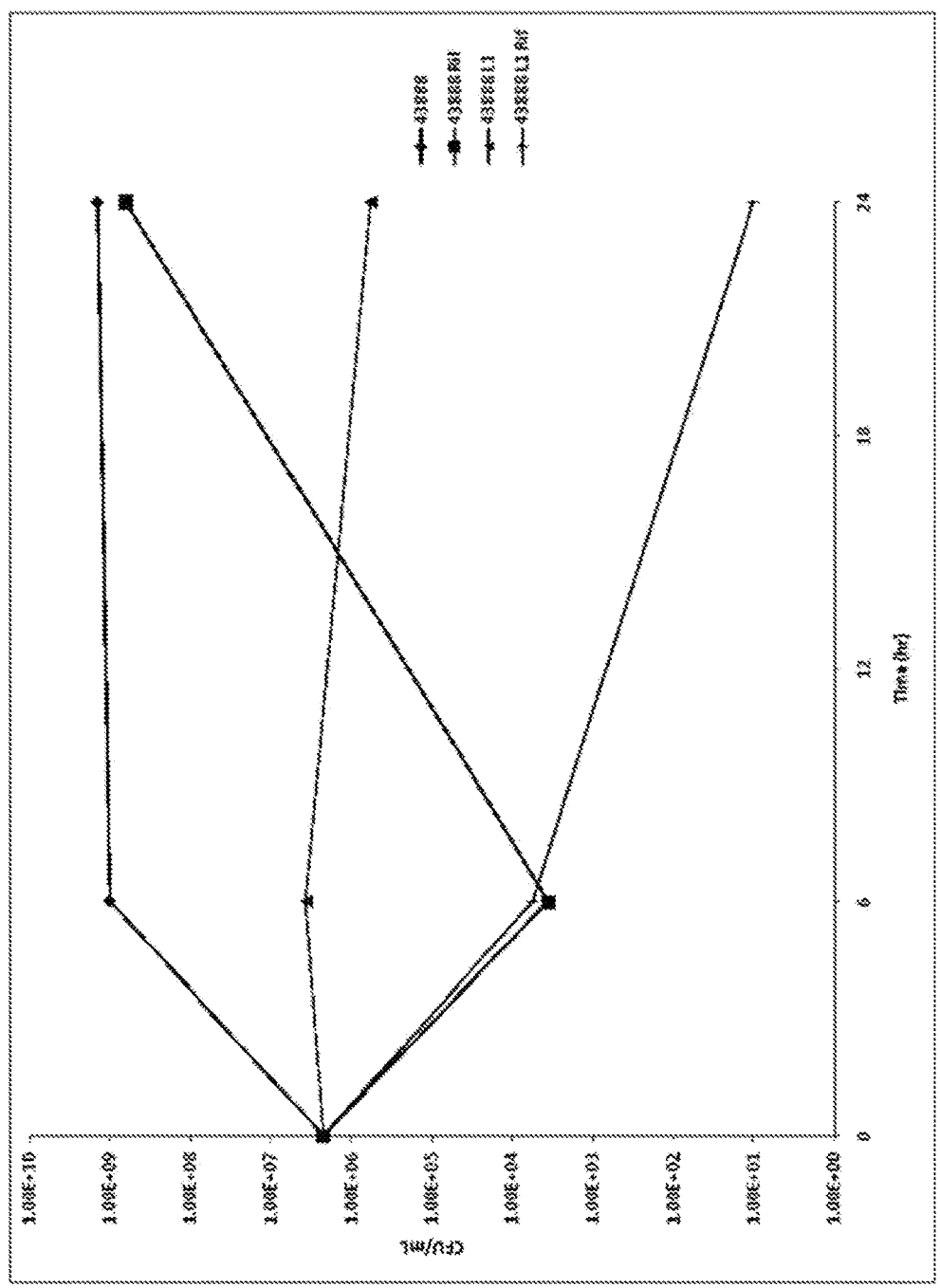
FIG. 10B shows the results of a time-kill assay of ApoL1 with and without rifampin against EC43888 in CAMHB.

FIG. 10B shows the results of a time-kill assay of ApoL1 with and without rifampin against EC43888 in CAMHB.

Example 12

Figure 39A:
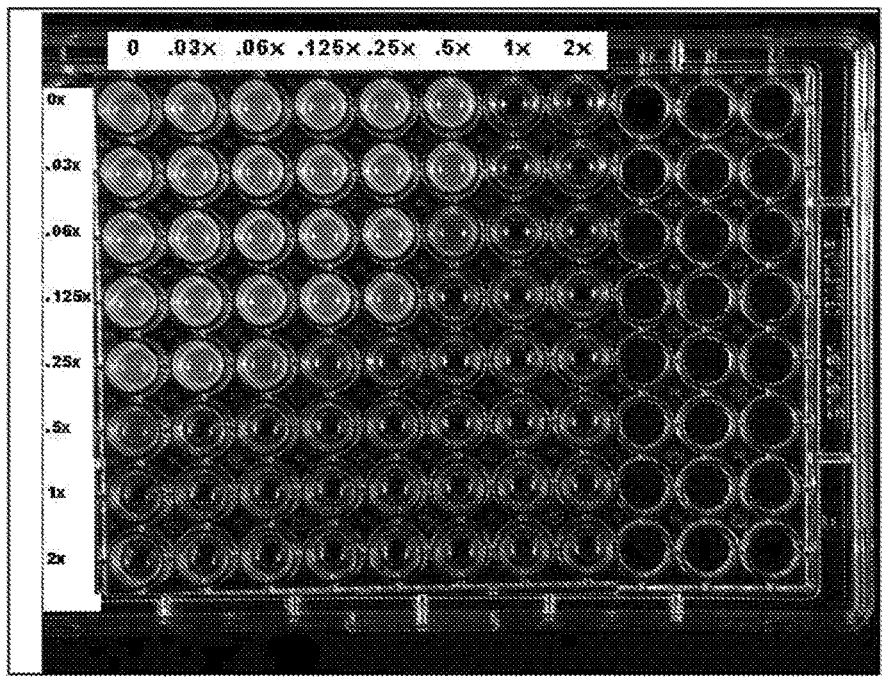
FIG. 39A shows the results of the checkerboard assay for the antibiotic rifampin and the iron chelator ApoL1 against AB19606.
Figure 39B:
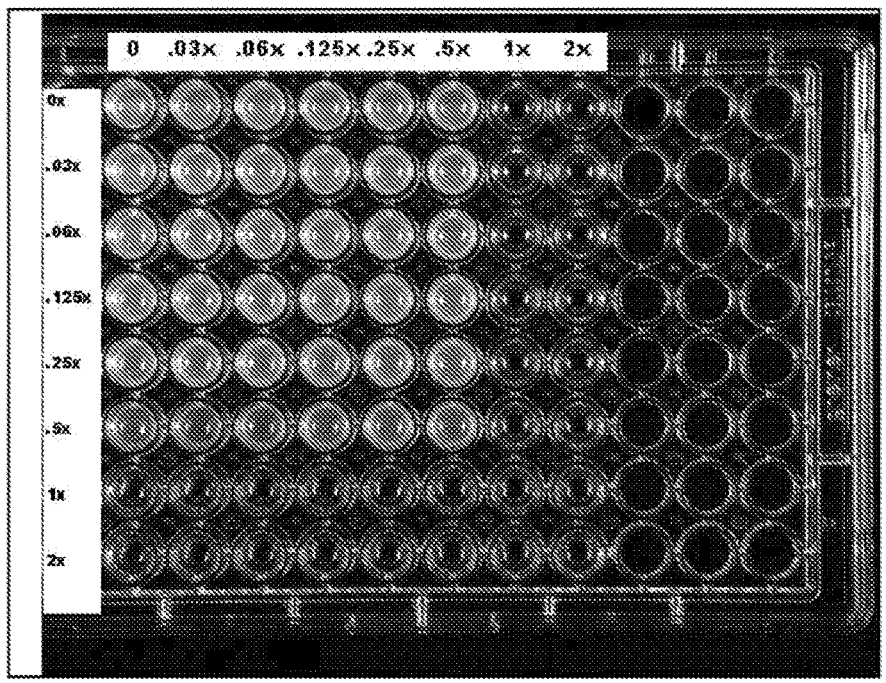
FIG. 39B shows the results of checkerboard assay for the antibiotic doxycycline and ApoL1 against AB19606.

Drug interactions were initially evaluated with the "checkerboard" microdilution design, which provided a matrix of all drug combinations assayed in terms of fractions of the previously determined MIC. The checkerboard microdilution design is described in R. J. Tallarida, "Drug Synergism: Its Detection and Applications," Journal of Pharmacology and Experimental Therapeutics, 865-872 (2001); and in R. L. White, et al., (1996), supra. FIGS. 39A and 39B show the wellplates having different concentrations of iron chelator and antibiotic, as labeled along the x-axis and y-axis. FIG. 39A shows the results of the checkerboard assay for the antibiotic rifampin and the iron chelator ApoL1 against AB19606, showing moderate synergy against that bacteria strain. FIG. 39B shows the results of checkerboard assay for the antibiotic doxycycline and ApoL1 against AB19606. This assay indicated indifference in that the combination of doxycycline and ApoL1 were not more effective than the compounds separately.

Example 13

The checkerboard assay was used to asses other combinations of iron chelators and antibiotics. The fractional inhibitory concentration index (FIC), which was calculated as follows: FIC=(MIC A in combination/MIC A)+(MIC B in combination/MIC B). Interaction was defined as synergistic if the FIC was <1.0, preferably <0.5, no interaction if the FIC was >1.0 and <4.0, and antagonistic if the FIC was >4.0.

Table 7 shows the FIC calculated from the checkerboard assay with the iron chelator deferiprone in combination with the antibiotics amikacin, doxycycline, cefotaxine, colisitin, and rifampin. The assay was run against the multi-drug resistant bacterial species AB 19606, AB 17978, KP ndm, PA PAO1, PA 27853, EC 35718, and EC 43888. Blank spaces indicate concentrations not tested. The results indicate that all of the tested iron chelators exhibited a synergistic effect with rifampin against all of the bacterial species. Against the species PA PAO1 and PA 27853, all the antibiotics except for Ami. Exhibited a synergistic effect with rifampin.

TABLE 7

| Deferiprone | Amikacin | Doxycycline | Cefotaxine | Colisitin | Rifampin |
|---|---|---|---|---|---|
| AB 19606 | 1.25 | 2.25 | 1.25 | 1.25 | 0.75 |
| AB 17978 | 1.25 | 1.25 | 1.25 | 1.25 | 0.75 |
| KP ndm |  |  |  | 1.25 | 0.75 |
| PA PAO1 |  | 0.75 | 0.75 | 0.75 | 0.75 |
| PA 27853 | 1.25 | 0.75 | 0.75 | 0.75 | 0.75 |
| EC 35218 |  | 1.25 | 1.25 | 1.25 | 0.75 |
| EC 43888 |  | 1.25 | 1.25 | 1.25 | 0.75 |

Table 8-9 shows the FIC calculated from the checkerboard assay with the iron chelator Apo6619 in combination with the antibiotics amikacin, doxycycline, cefotaxine, colisitin, and rifampin. The assay was run against the multi-drug resistant bacterial species AB 19606, AB 17978, EC 35218, and EC 43888.

TABLE 8

| Apo6619 | Amikacin | Doxycycline | Cefotaxine | Colisitin | Rifampin |
|---|---|---|---|---|---|
| AB 19606 | 1.25 | 2.25 | 1.25 | 1.25 | 0.75 |
| AB 17978 | 0.75 | 1.25 | 0.75 | 0.75 | 0.75 |
| EC 35218 |  | 1.25 | 1.25 | 1.25 | 1.75 |
| EC 43888 |  | 1.25 | 1.25 | 1.25 | 0.75 |

Table 9 shows the FIC calculated from the checkerboard assay with the iron chelator VK28 in combination with the antibiotics amikacin, doxycycline, cefotaxine, colisitin, and rifampin. The assay was run against the multi-drug resistant bacterial species AB 19606 and AB 17978.

TABLE 9

| VK28 | Amikacin | Doxycycline | Cefotaxine | Colistin | Rifampin |
|---|---|---|---|---|---|
| AB 19606 | 1.25 | 2.25 | 1.25 | 0.75 | 1.25 |
| AB 17978 | 1.25 | 1.25 | 0.75 | 0.75 | 0.75 |

In summary, VK28, Deferiprone, and Apo6619 exhibited strong synergy with rifampin when assessed by the time kill method, and moderate degrees of synergy when assessed by checkerboard.

Figure 22:
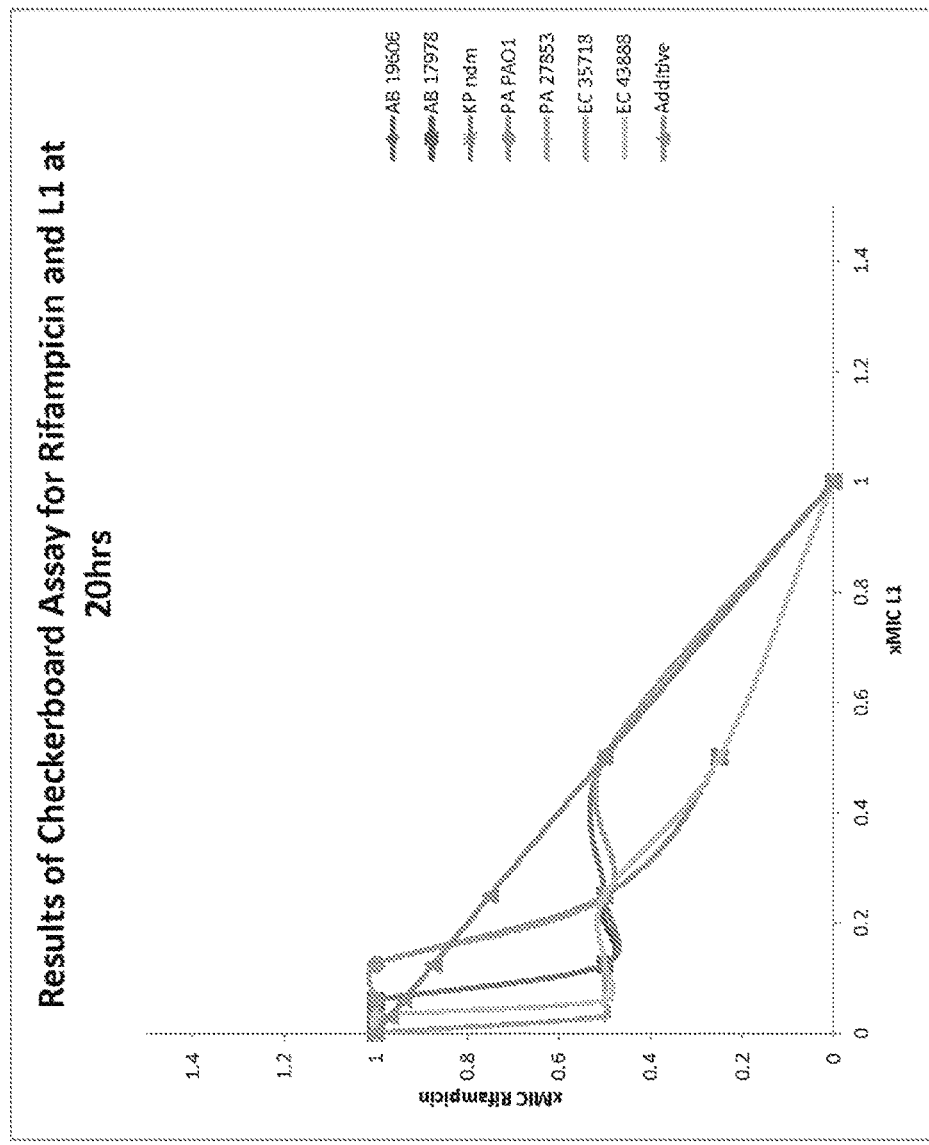
FIG. 22 is a isobologram graph of the MIC ApoL1 (x-axis) plotted against MIC Rifampicin (y-axis).
Figure 23:
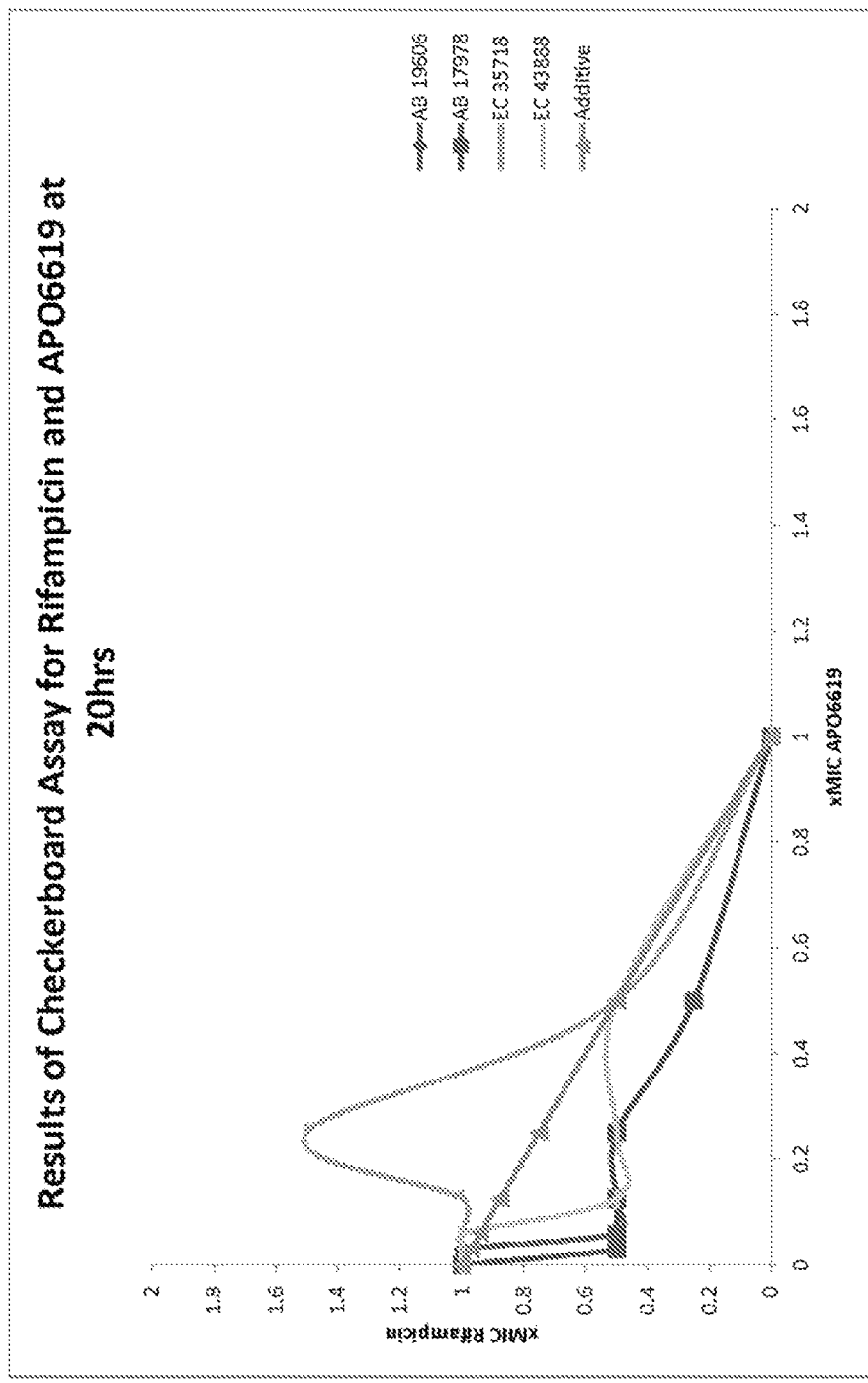
FIG. 23 is the isobologram graph showing MIC Apo6619 (x axis) plotted against MIC Rifampicin (y-axis).
Figure 24:
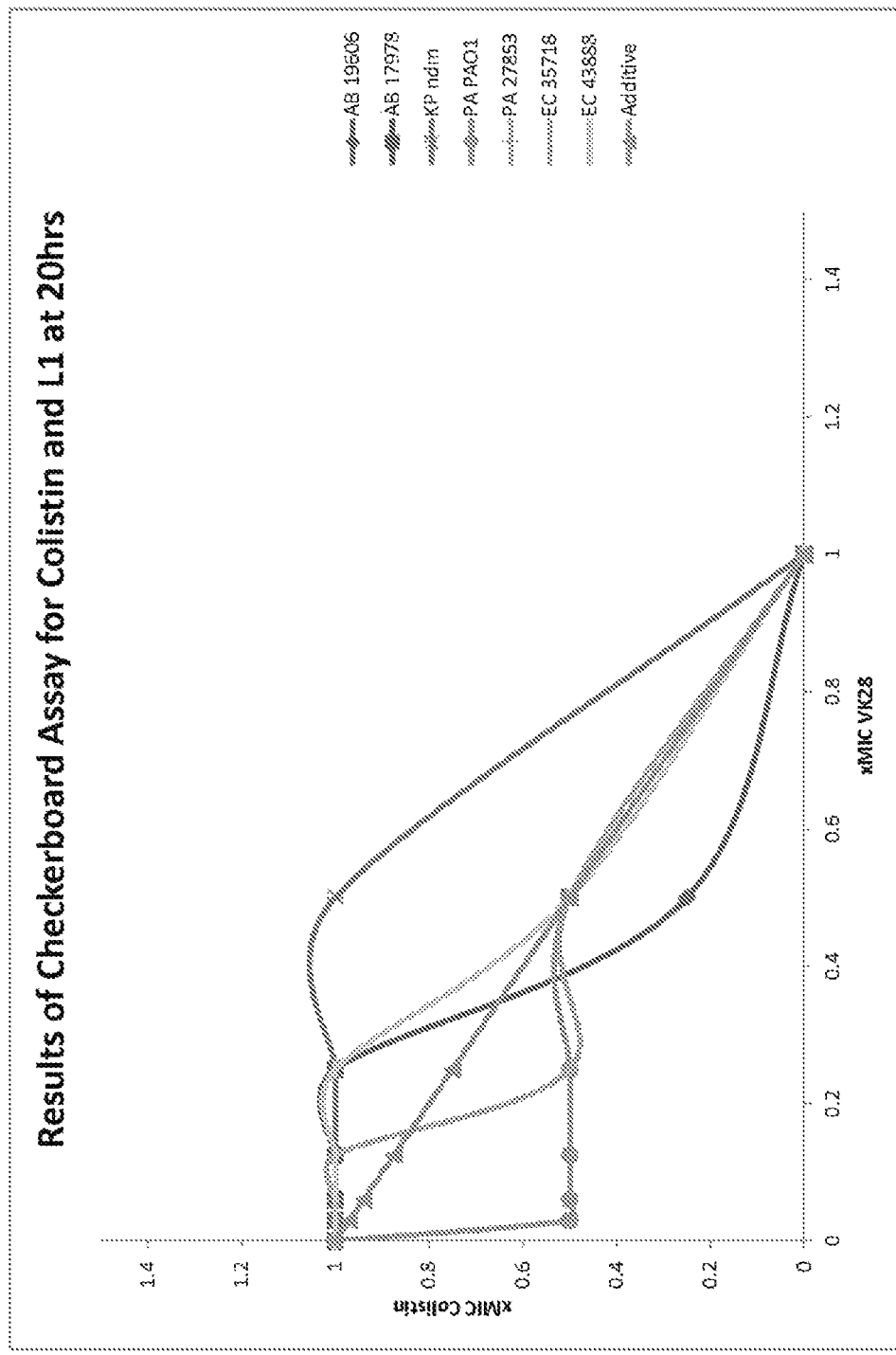
FIG. 24 is the isobologram graph showing MIC VK28 (x-axis) plotted against MIC Colistin (y-axis).
Figure 25:
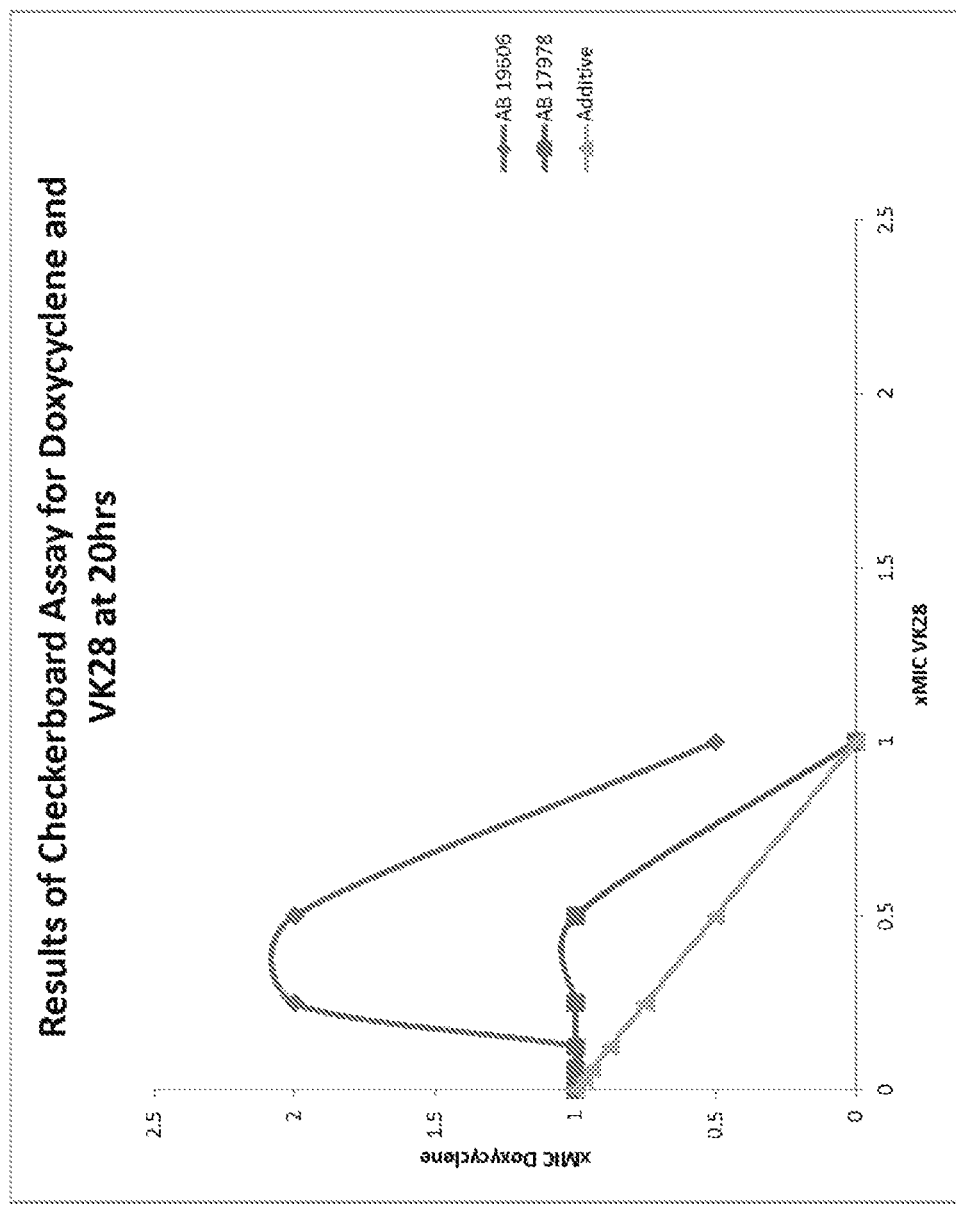
FIG. 25 is the isobologram graph showing MIC VK28 (x-axis) plotted against MIC Doxycycline (y-axis).
Figure 26:
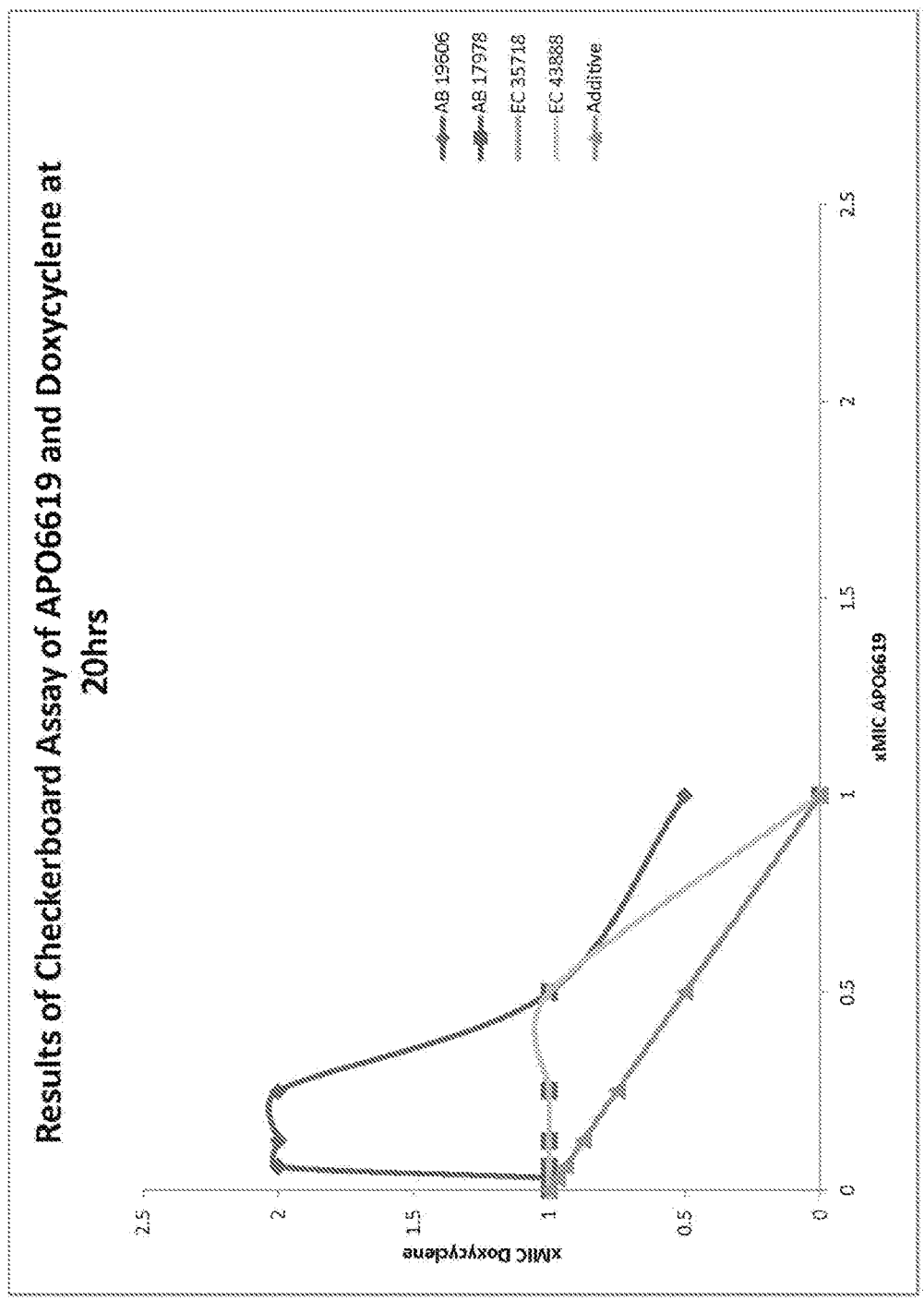
FIG. 26 is the isobologram graph showing MIC Apo6619 (x-axis) plotted against MIC Doxycycline (y-axis).
Figure 27:
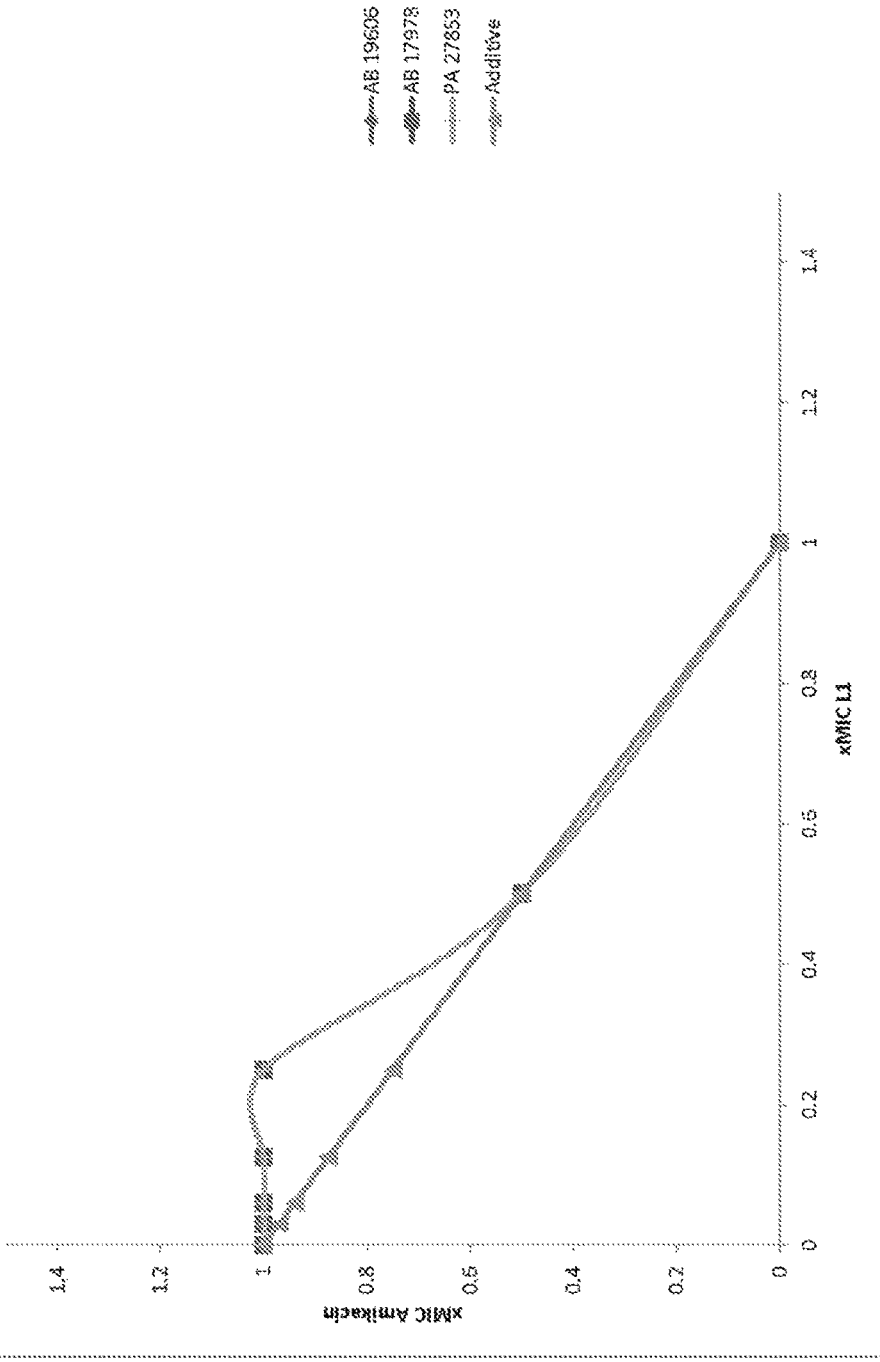
FIG. 27 is the isobologram graph of MIC ApoL1 (x-axis) plotted against MIC Amikacin (y-axis).
Figure 28:
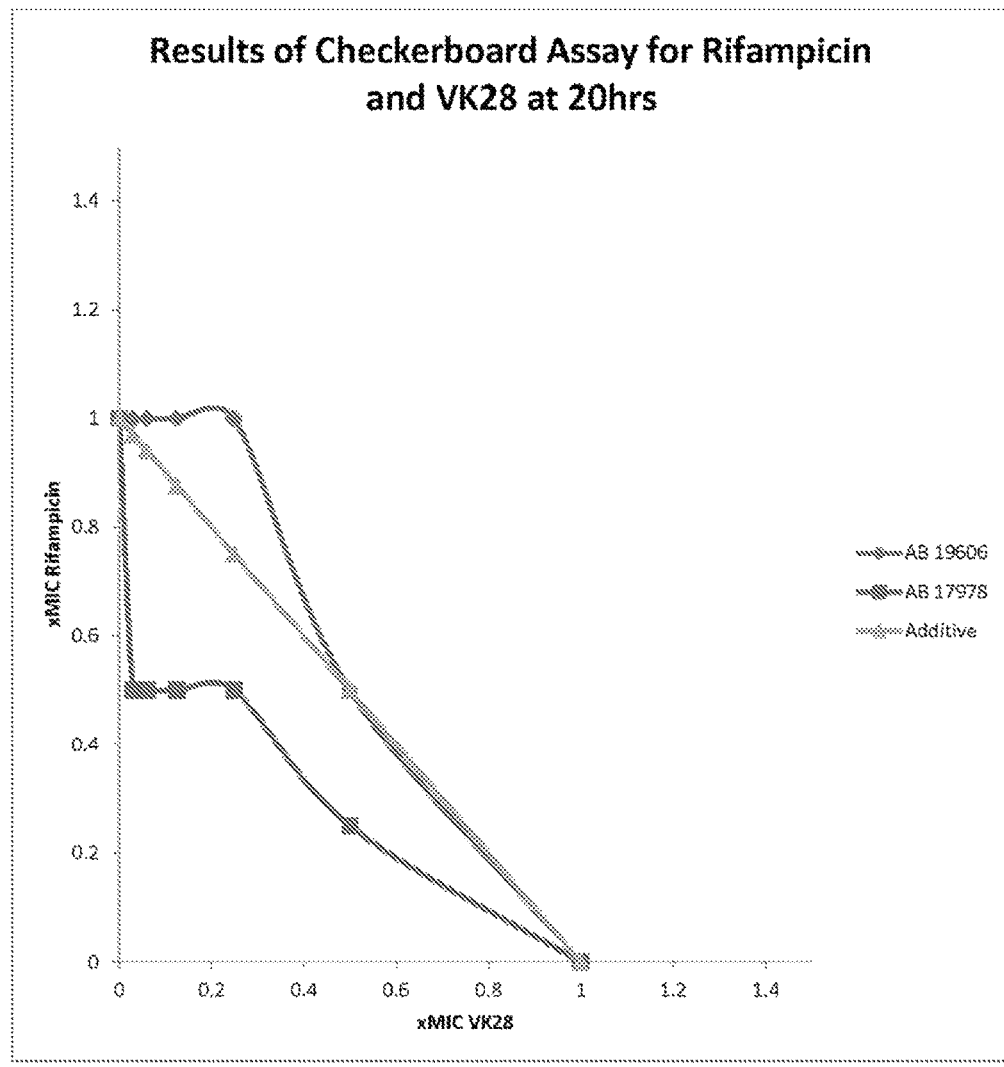
FIG. 28 is the isobologram graph of MIC VK28 (x-axis) plotted against MIC Rifampicin (y-axis).
Figure 29:
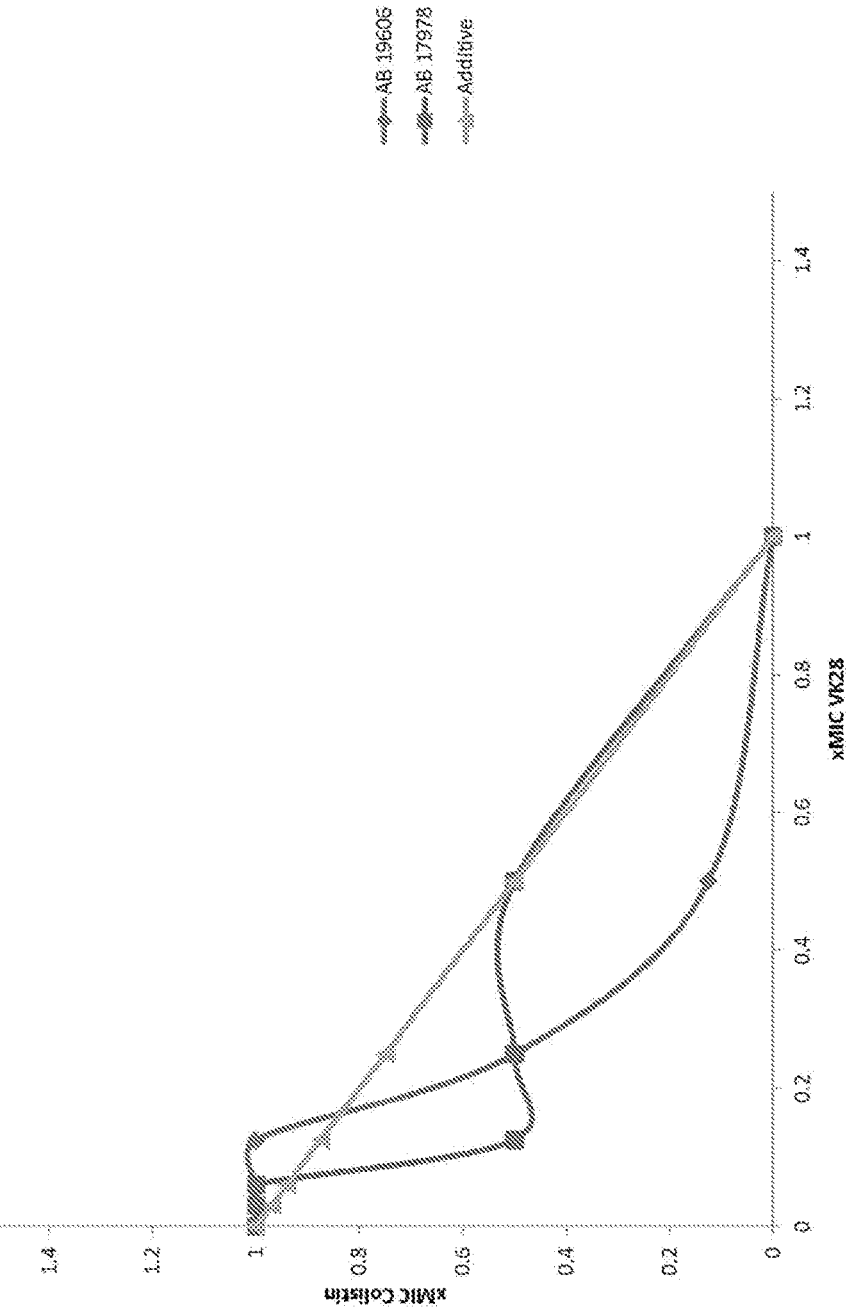
FIG. 29 is the isobologram graph of MIC VK28 (x-axis) plotted against MIC Colistin (y-axis).
Figure 30:
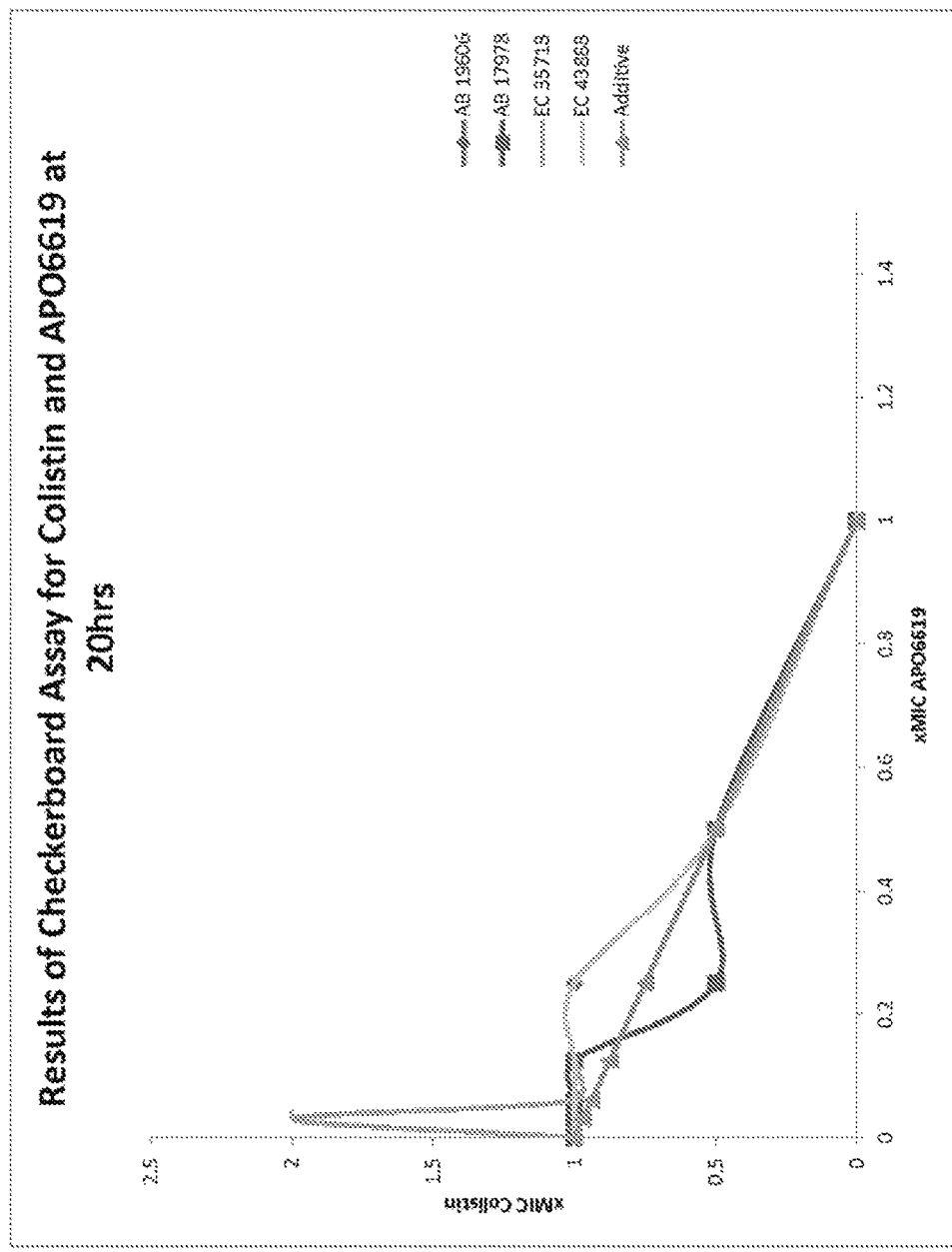
FIG. 30 is the isobologram graph of MIC Apo6619 (x-axis) plotted against MIC Colistin (y-axis).
Figure 31:
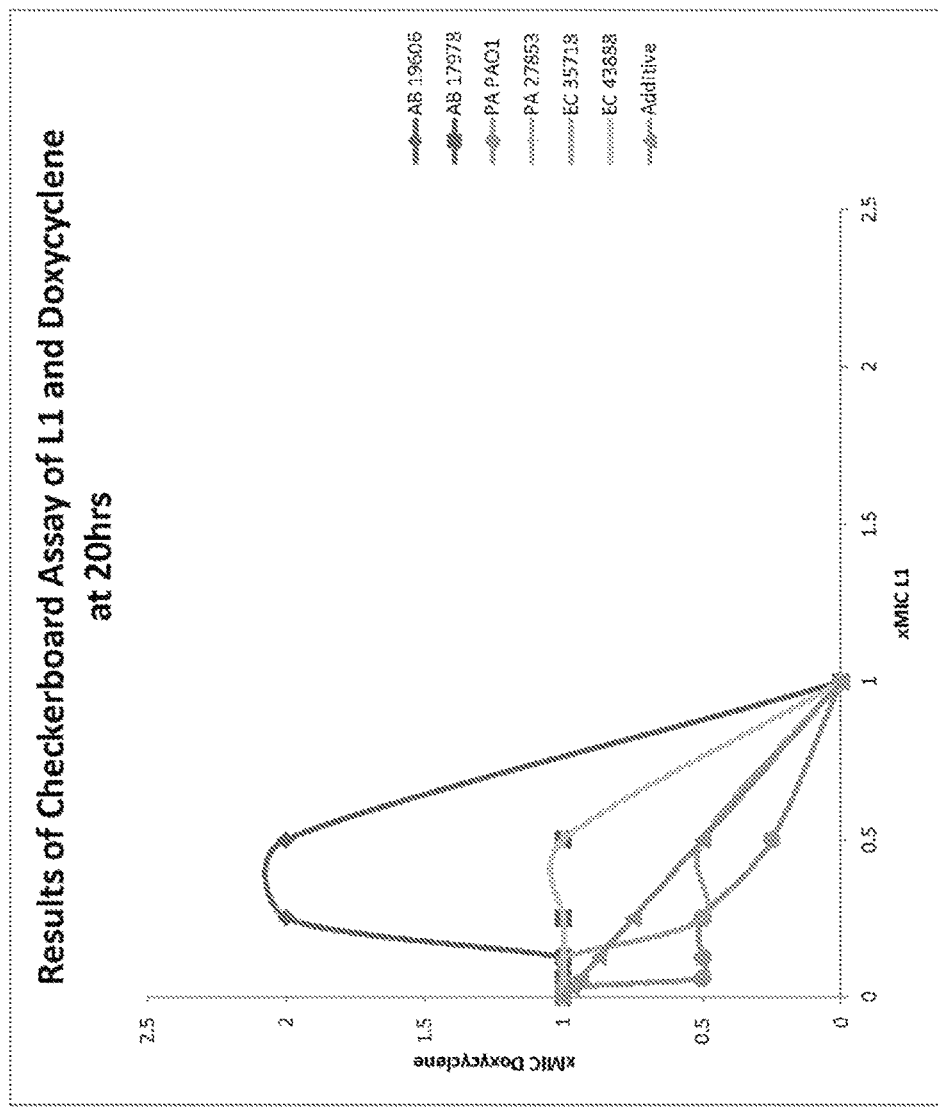
FIG. 31 is the isobologram graph of MIC ApoL1 (x-axis) and MIC Doxycycline (y-axis).
Figure 32:
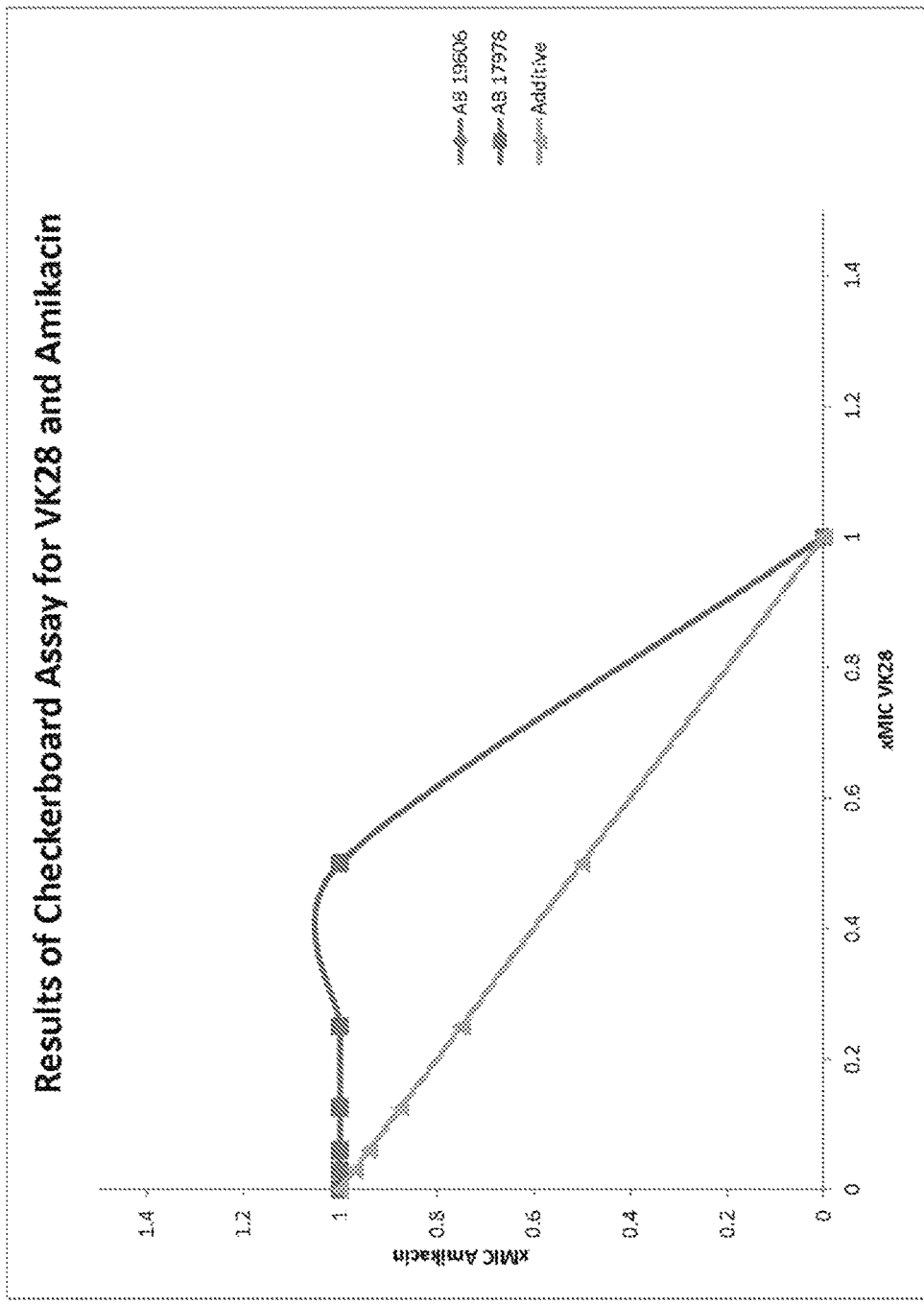
FIG. 32 is the isobologram graph of MIC VK28 (x-axis) plotted against MIC Amikacin (y-axis).

The results of the checkerboard assay are further demonstrated as isobolograms in FIGS. 22-33 for the different strains of bacteria at 20 hours. FIG. 22 is an isobologram showing MIC ApoL1 (x-axis) plotted against MIC Rifampicin (y-axis), FIG. 23 is the isobologram showing MIC Apo6619 (x axis) plotted against MIC Rifampicin (y-axis), FIG. 24 is the isobologram showing MIC VK28 (x-axis) plotted against MIC Colistin (y-axis); FIG. 25 is the isobologram showing MIC VK28 (x-axis) plotted against MIC Doxycyclene (y-axis); FIG. 26 is the isobologram showing MIC Apo6619 (x-axis) plotted against MIC Doxycyclene (y-axis); FIG. 27 is the isobologram of MIC ApoL1 (x-axis) plotted against MIC Amikacin (y-axis); FIG. 28 is the isobologram of MIC VK28 (x-axis) plotted against MIC Rifampicin (y-axis); FIG. 29 is the isobologram of MIC VK28 (x-axis) plotted against MIC Colistin (y-axis); FIG. 30 is the isobologram of MIC Apo6619 (x-axis) plotted against MIC Colistin (y-axis); FIG. 31 is the is the isobologram of MIC ApoL1 (x-axis) plotted against MIC Doxycyclene (y-axis); FIG. 32 is the isobologram of MIC VK28

Figure 33:
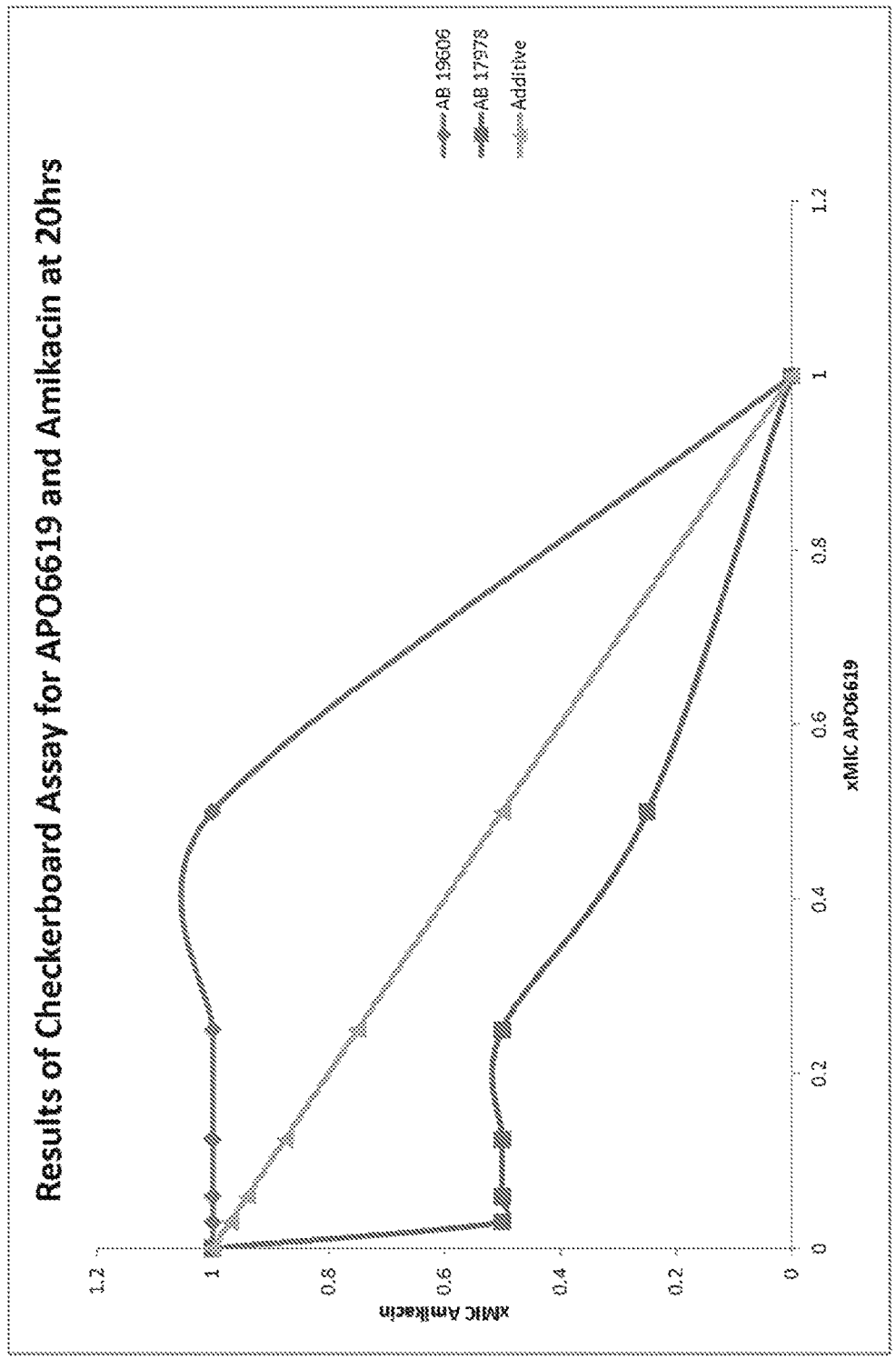
FIG. 33 is the isobologram graph of MIC Apo6619 (x-axis) plotted against MIC Amikacin (y-axis).

(x-axis) plotted against MIC Amikacin (y-axis); FIG. 33 is the isobologram of MIC Apo6619 (x-axis) plotted against MIC Amikacin (y-axis).

Example 14

Figure 11A:
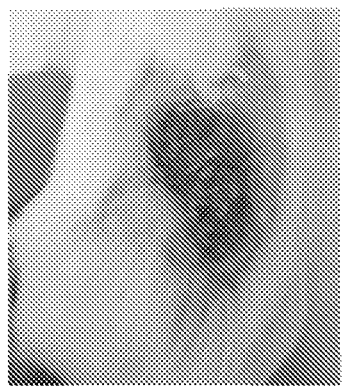
FIGS. 11A (control composition) and 11B (treated with VK28) show the wound treated with the control composition did not heal as well as the wound treated with the iron chelator composition.
Figure 11B:
FIG. 11 shows photographs of the results of in vivo evaluation of the effectiveness of VK28 in treating a bacterial infection in a wound of mice.

This example provides an in vivo evaluation of the effectiveness of VK28 in treating a bacterial infection. Mice were wounded with 6 mm punch biopsy and infected with AB5075 (MRSN959) and treated daily for 14 days with poloxamer F-127 gel alone as a control composition (FIG. 11A) or F-127 gel containing 5% VK28 (as a topical composition containing an iron chelator). FIGS. 11A and 11B show the wound treated with the control composition did not heal as well as the wound treated with the iron chelator composition. Healing scab and reduced wound size were observed on the treated mouse. In similar evaluations with other mice, a composition containing 1% VK28 was not particularly efficacious, but a composition containing 5% VK28 was efficacious in promoting wound healing.

Example 15

Figure 12:
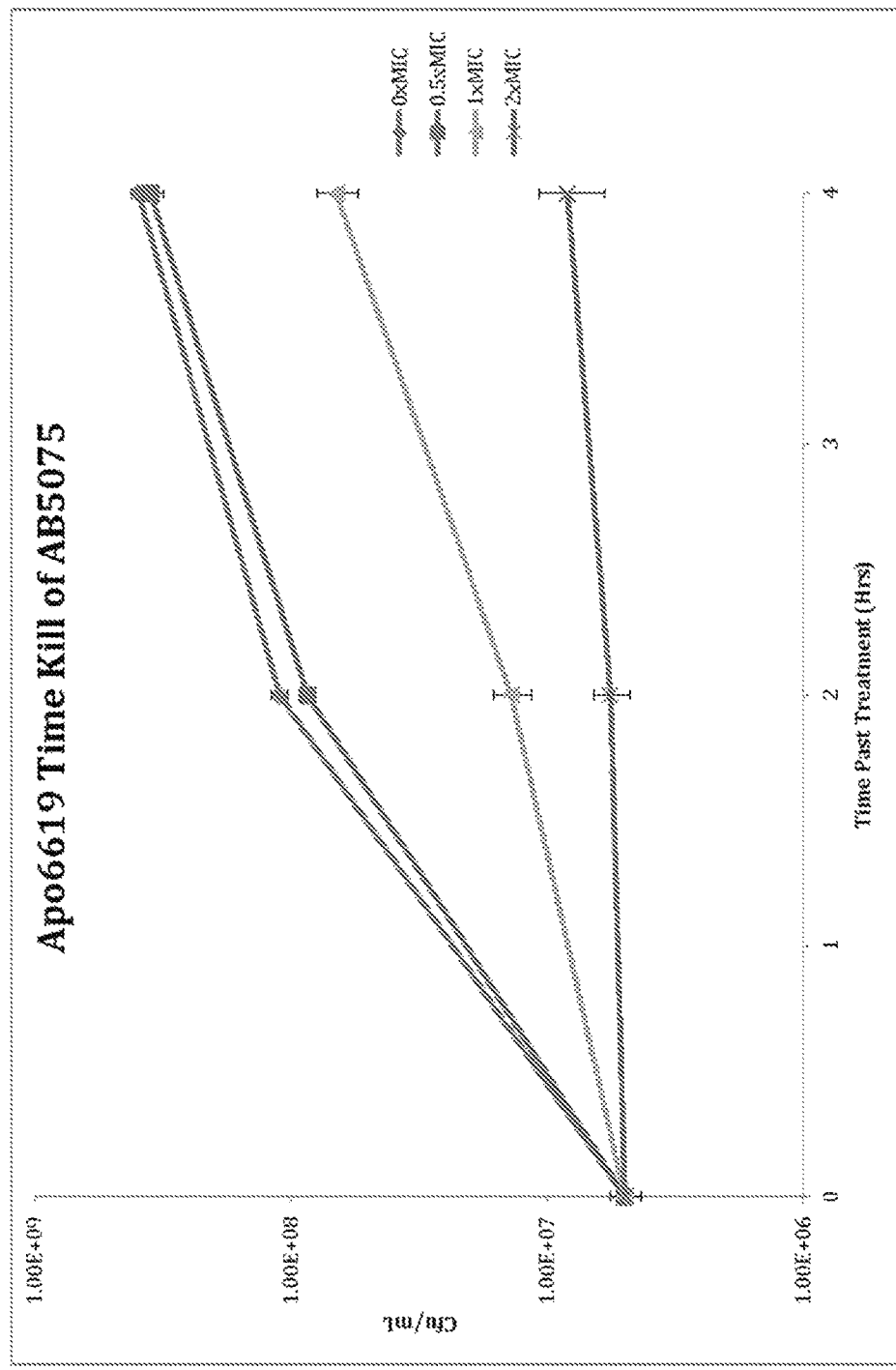
FIG. 12 shows a graph demonstrating the time kill curves for APO6619 against AB5075 bacteria cultures.

In this example, time-kill assays were performed as described in Example 9 using Apo6619 as the iron chelator against AB5075 (MRSN959), the MDR-clinical isolate of $A.$ $baumannii$. The initial inocula was $1\times10^6$ CFU/mL, and were challenged with 0.5×MIC, 1×MIC and 2×MIC of Apo6619. Time-kill results were analyzed by determining the change in log 10 numbers of CFU/mL at 0, 2 and 4 hours. FIG. 12 shows the time kill curves demonstrating that APO6619 demonstrated bactericidal effect.

Example 16

Figure 13:
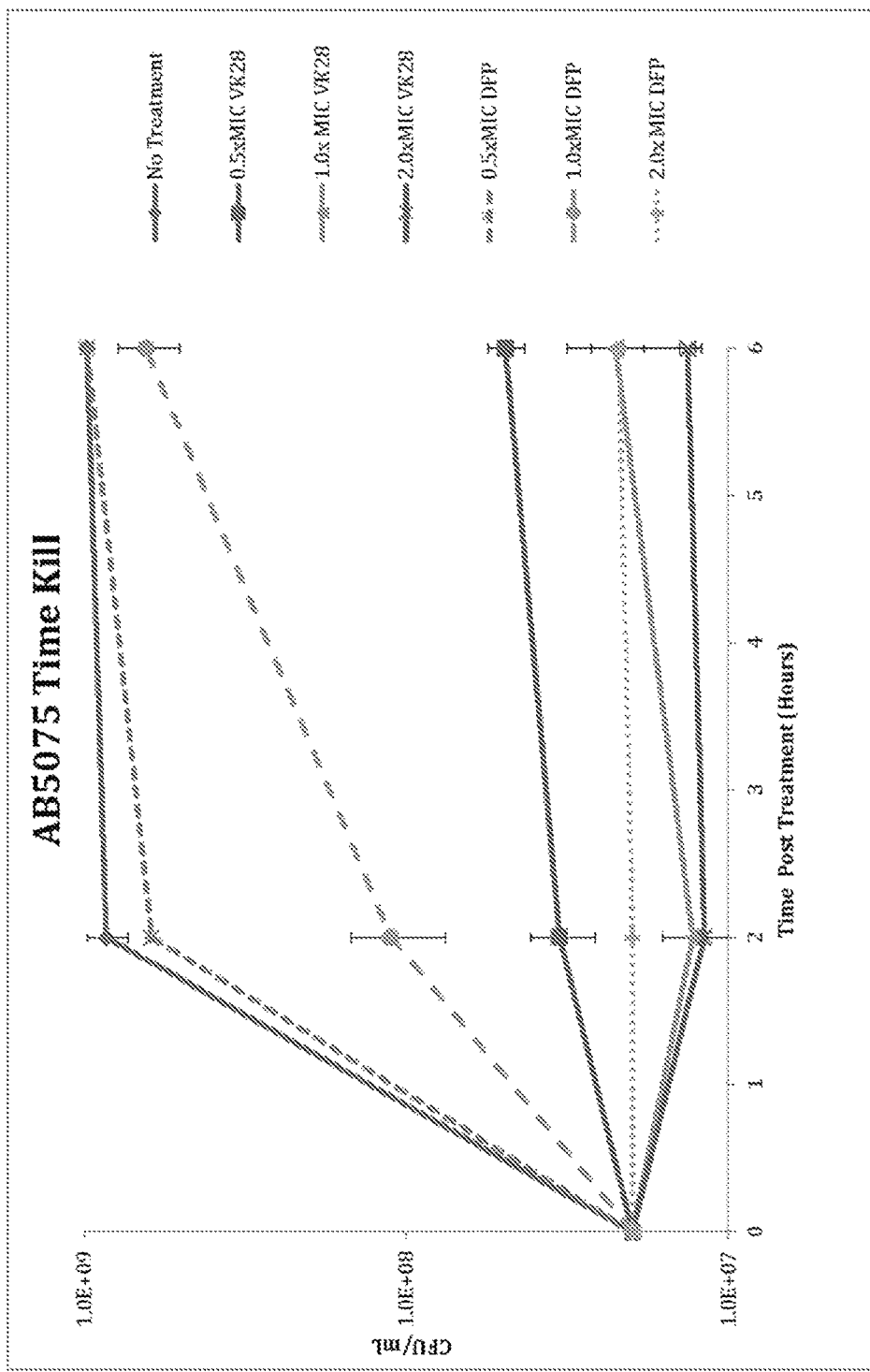
FIG. 13 shows a graph demonstrating the time kill curves for both VK28 and DFP at different concentrations in AB5075 bacteria cultures.

In this example, time-kill assays were performed as described in Example 9 using VK28 or DFP as the iron chelator against AB5075, the MDR-clinical isolate of $A.$ $baumannii$. The initial inocula was $1\times10^6$ CFU/mL, and were challenged with 0.5×MIC, 1×MIC and 2×MIC of either VK28 or DFP. Time-kill results were analyzed by determining the change in log 10 numbers of CFU/mL at 2 and 6 hours. FIG. 13 shows the time kill curves for both VK28 and DFP.

The untreated sample (♦) had about $1\times10^9$ CFU/mL after 6 hours. The sample treated with VK28 at 0.5 MIC (■), VK28 at 1×MIC (▲), and VK28 at 2×MIC (x) had an inhibitory effect on the CFU/ml. The samples treated with DFP showed a slight inhibitory effect at 1×MIC (circle, dotted line), and a stronger inhibitory effect at 2×MIC (+, dotted line).

Example 17

Figure 14:
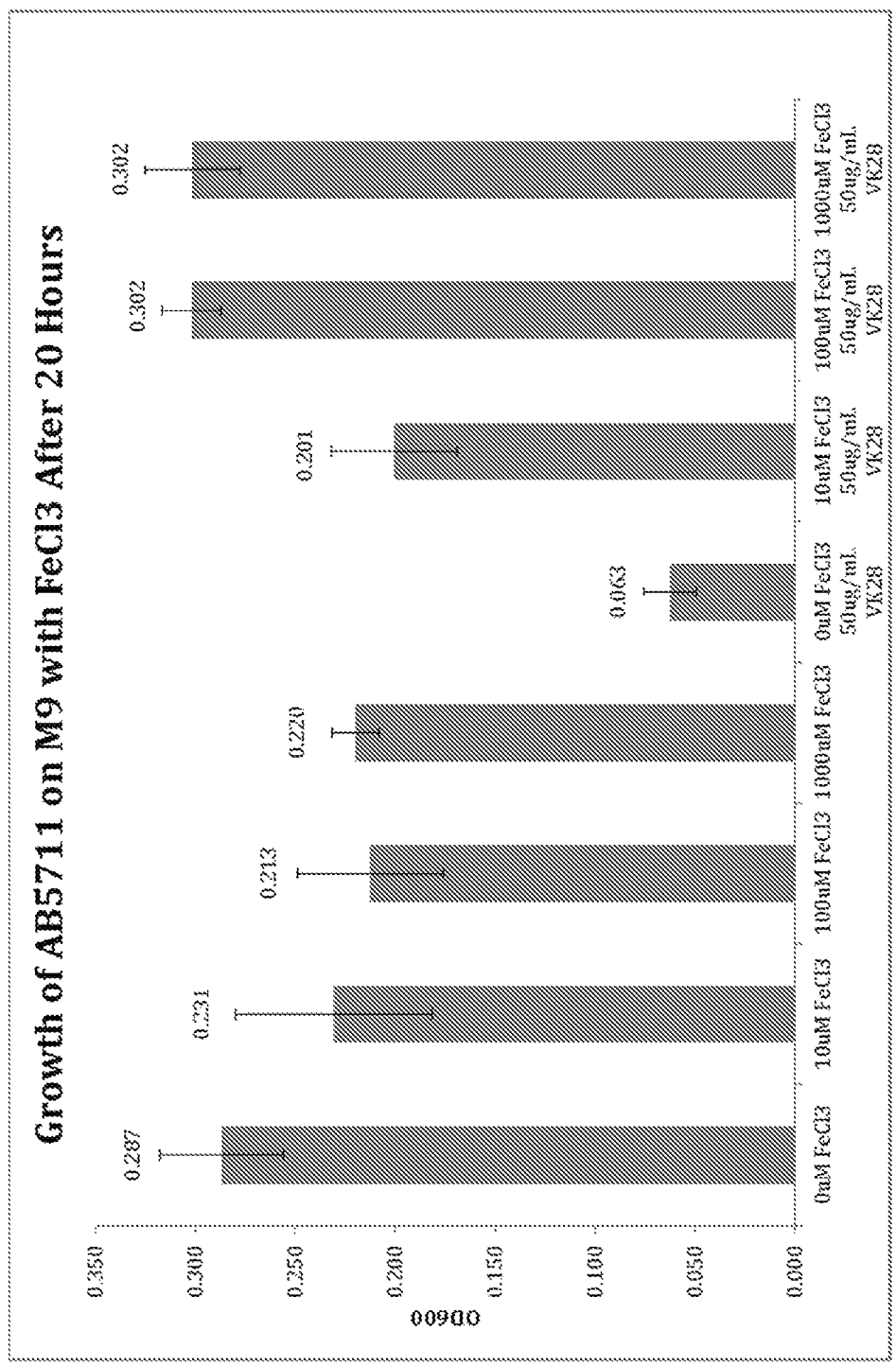
FIG. 14 is a bar graph depicting the results of growth of AB5711 bacteria cultures in the presence of $FeCl_3$ alone or VK28 with or without the addition of $FeCl_3$.

This example provides further evidence that the removal of iron is responsible for bacterial growth inhibition. $A.$ $baumannii$ isolate 5711 was grown in low iron M9 media supplemented with 0 μM, 10 μM, 100 μM, or 1000 μM $FeCl_3$ with and without the addition of 50 μg/ml of VK28 following 4 hr of growth. Growth was estimated by absorbance at 600 nm after 20 hours. FIG. 14 is a bar graph depicting the results, showing that the inhibition of growth can be rescued by the addition of $FeCl_3$ suggesting that VK28 plays a role in growth inhibition involving iron.

Example 18

Figure 15:
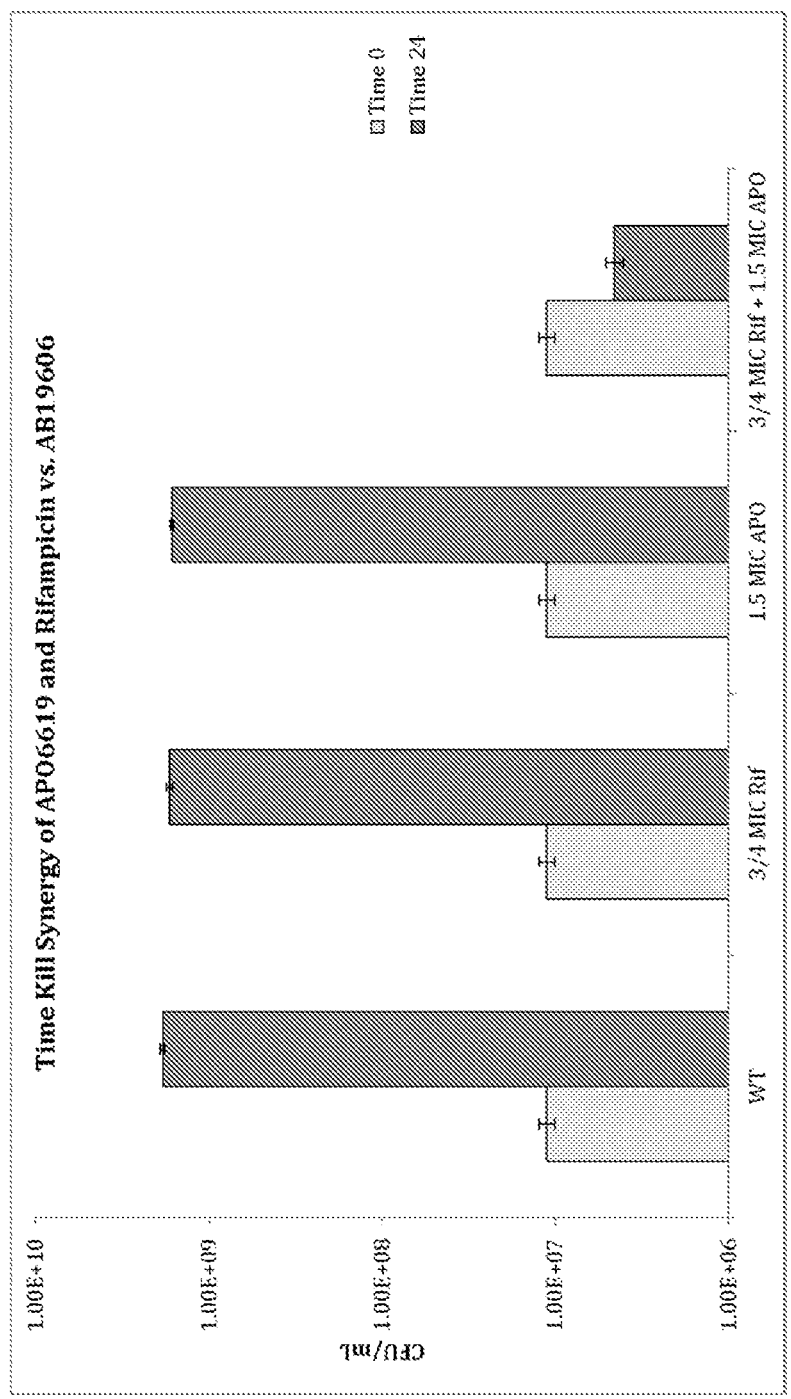
FIG. 15 is a bar graph that demonstrates the results of treatment of bacteria strains AB19606 with Rifampicin in combination with Apo6619 after 24 hours in culture.

This example demonstrated synergistic effect of APO6619 in combination with Rifampicin on the growth of AB19606, a strain of $A.$ $baumannii$. $1\times10^7$ CFU/ml were untreated (WT), treated with ¾×MIC Rifampicin, 1.5×MIC Apo6619, or a combination of ¾×MIC Rifampicin and 1.5×MIC Apo6619, and the growth was estimated by absorbance at 600 nm at time 0 hr and 24 hour. FIG. 15 demonstrates the results showing that Rifampicin in combination with Apo6619 have a synergistic effect in inhibiting growth of AB19606.

Example 19

Figure 16:
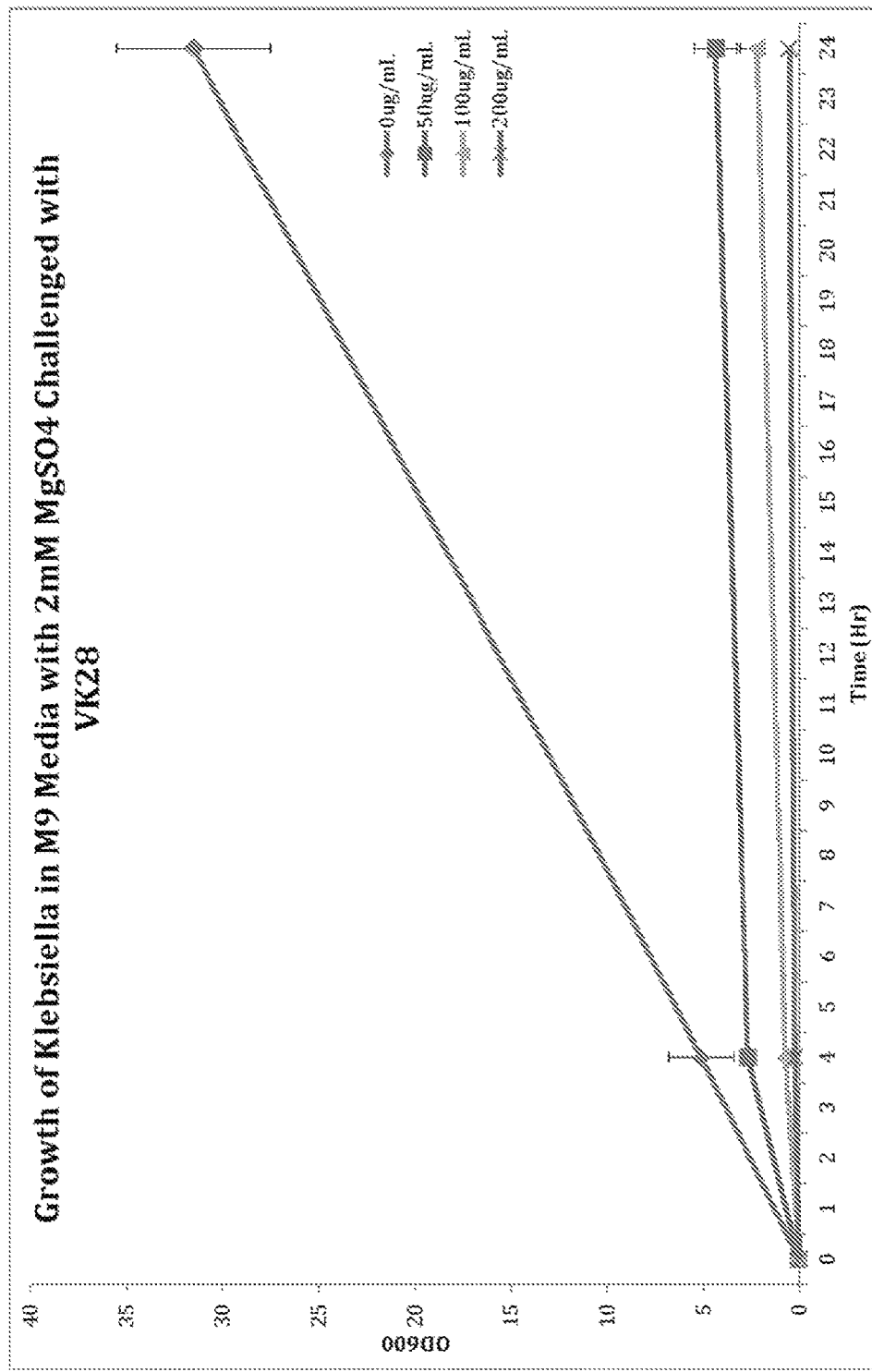
FIG. 16 is a growth curve graph that demonstrates the results of a time-kill assay for treatment of *Klebsiella* with VK28 in the presence of magnesium.

This example demonstrates VK28 can inhibition growth of $Klebsiella\ pneumonia$ in the presence of magnesium. $Klebsiella\ pneumonia$ was grown in M9 media containing 2 mM $MgSO_4$ for 24 hours in the presence of 0 μg/ml, 50 μg/ml, 100 μg/ml, or 200 μg/ml VK28. The $OD_{600}$ was measured at 0, 4, and 24 hour and the results are shown in the time-kill curves of FIG. 16. The results show that VK28 inhibition of growth is not reduced in the presence of magnesium.

Example 20

Figure 17:
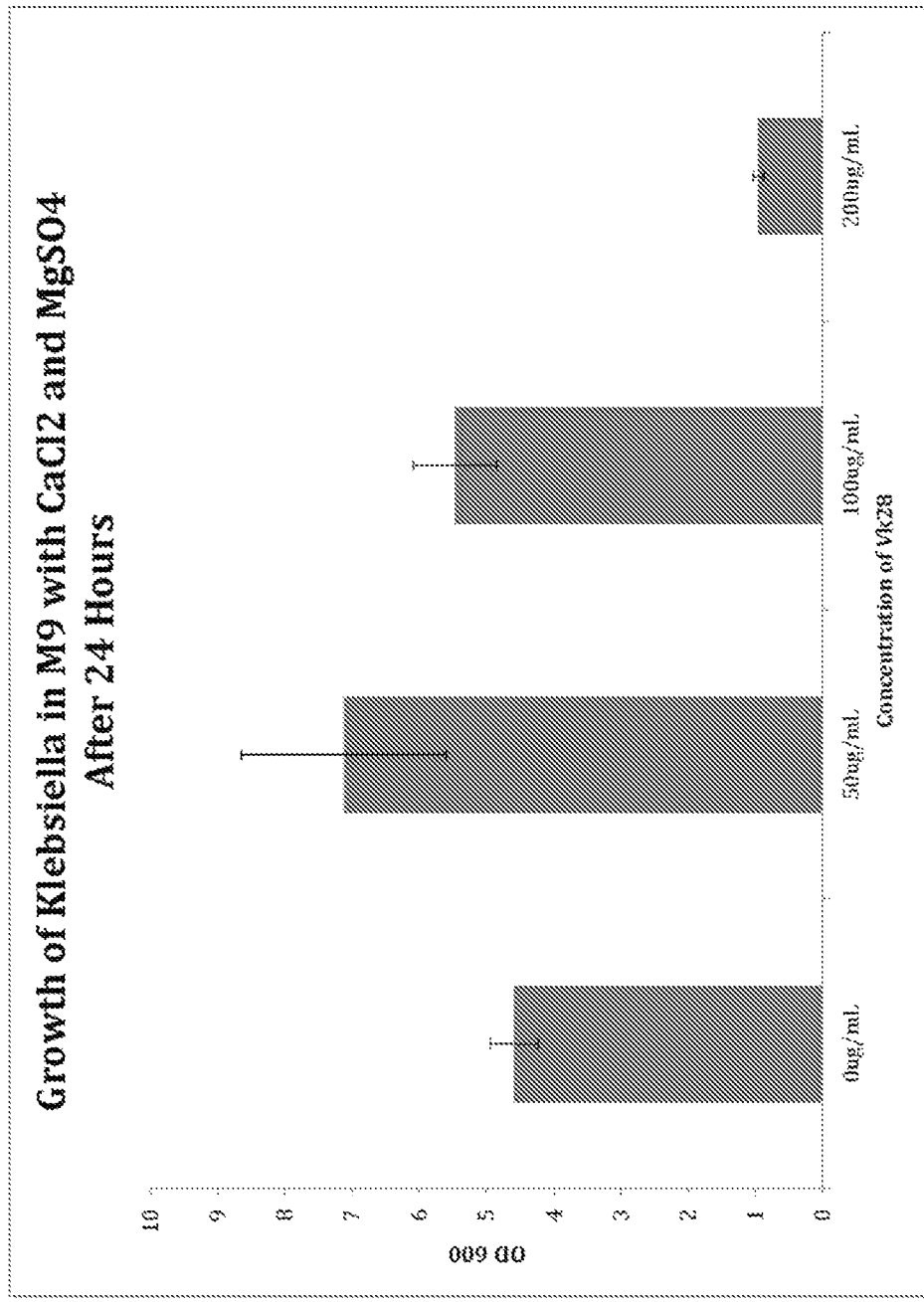
FIG. 17 is a bar graph that demonstrates the results of a time-kill assay for treatment of *Klebsiella* in the presence of magnesium and calcium.

This example demonstrates VK28 can inhibition growth of $Klebsiella\ pneumonia$ in the presence of calcium and magnesium. $Klebsiella\ pneumonia$ was grown similar to as described in Example 19 in M9 media containing 2 mM $MgSO_4$ and 1.34 mM $CaCl_2$ for 24 hours in the presence of 0 μg/ml, 50 μg/ml, 100 μg/ml, or 200 μg/ml VK28. The $OD_{600}$ was measured at 24 hour and the results are shown in the bar graph of FIG. 17. The results show that VK28 inhibition of growth is not reduced in the presence of magnesium and calcium.

Example 21

Figure 18:
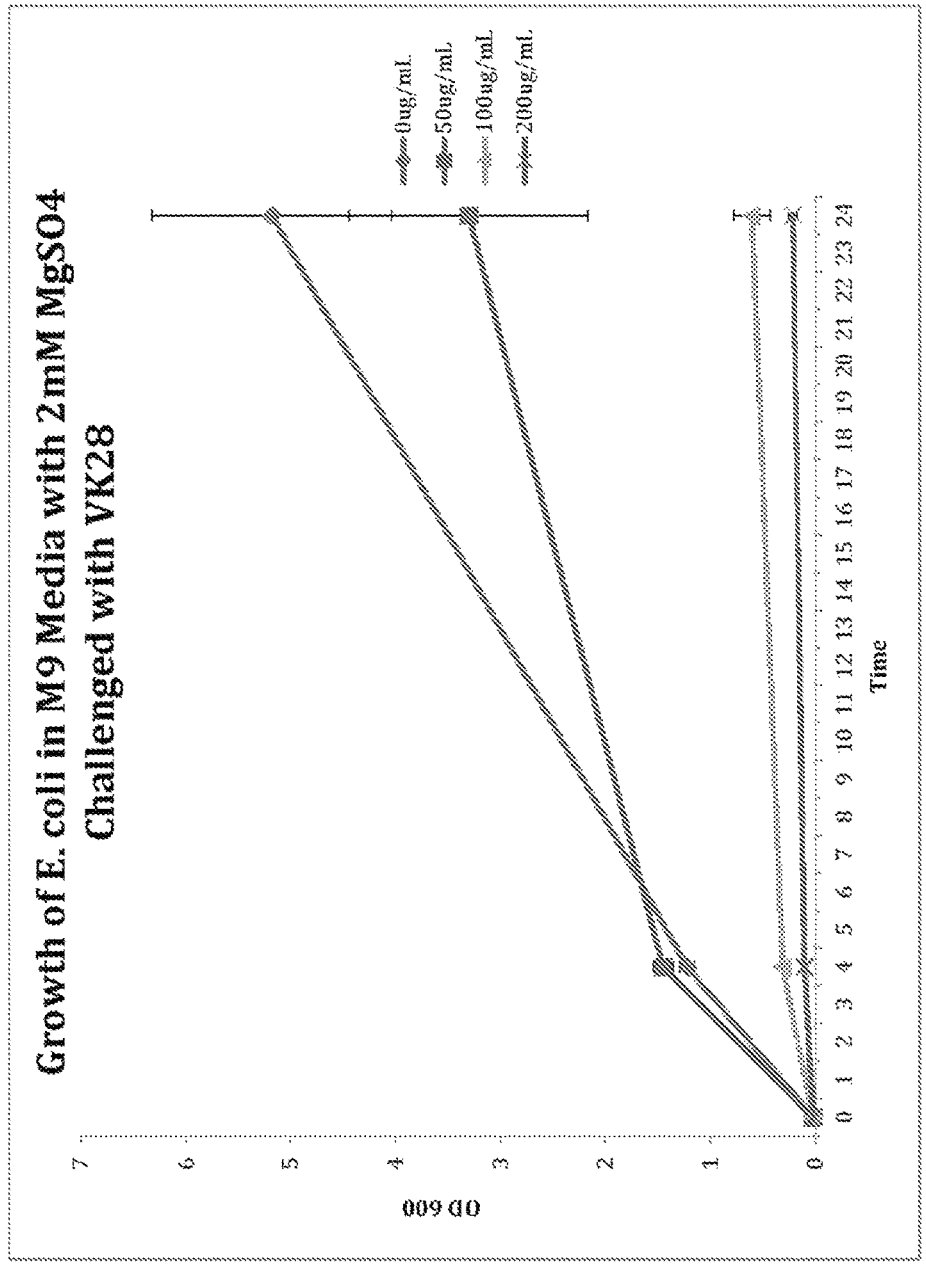
FIG. 18 is a growth curve graph that demonstrates the results of a time-kill assay for treatment of *E. Coli* with VK28 in the presence of magnesium and calcium.

In this example, time kill assays of VK28 in the presence of magnesium demonstrate that VK28 can inhibit growth of $Escherichia\ coli$ ($E.\ coli$) in the presence of magnesium. $Escherichia\ coli$ was grown similar to as described in Example 19 in M9 media containing 2 mM $MgSO_4$ for 24 hours in the presence of 0 μg/ml, 50 μg/ml, 100 μg/ml, or 200 μg/ml VK28. The $OD_{600}$ was measured at 0, 4, and 24 hour and the results are shown in the time-kill curves of FIG. 18. The results show that VK28 inhibition of growth of $E.\ coli$ is not reduced in the presence of magnesium and calcium.

Example 22

Figure 19:
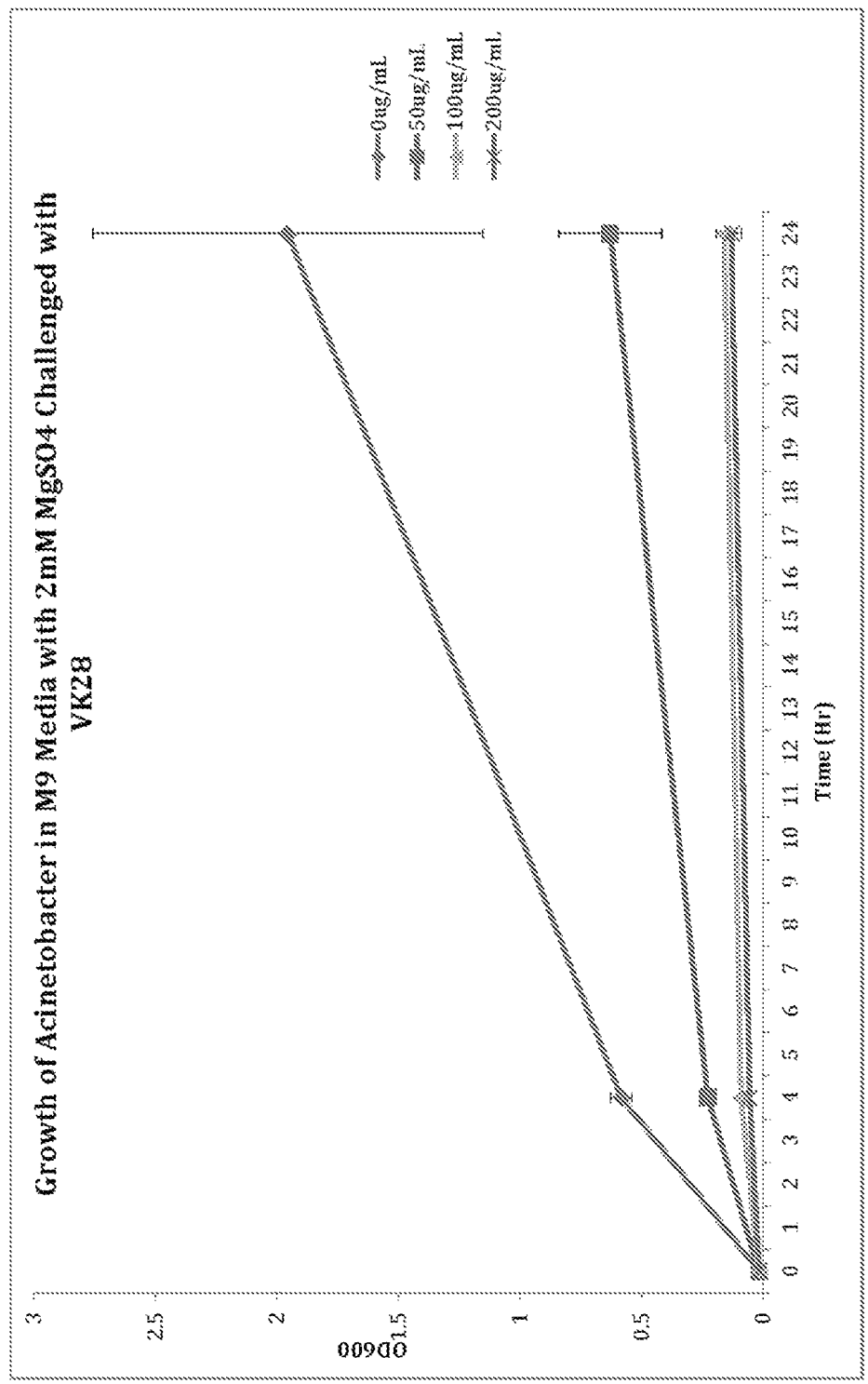
FIG. 19 is a growth curve graph that demonstrates the results of a time-kill assay for treatment of *Acinetobacter baumannii* with VK28 in the presence of magnesium.

This example demonstrates VK28 can inhibition growth of $Acinetobacter\ baumannii$ in the presence of magnesium. $Acinetobacter\ baumannii$ was grown similar to as described in Example 21 in M9 media containing 2 mM $MgSO_4$ for 24 hours in the presence of 0 μg/ml, 50 μg/ml, 100 μg/ml, or 200 μg/ml VK28. The $OD_{600}$ was measured at 0, 4, and 24 hour and the results are shown in the time-kill curves of FIG. 19. The results show that VK28 inhibition of growth of $Acinetobacter\ baumannii$ is not reduced in the presence of magnesium.

Example 23

Figure 20:
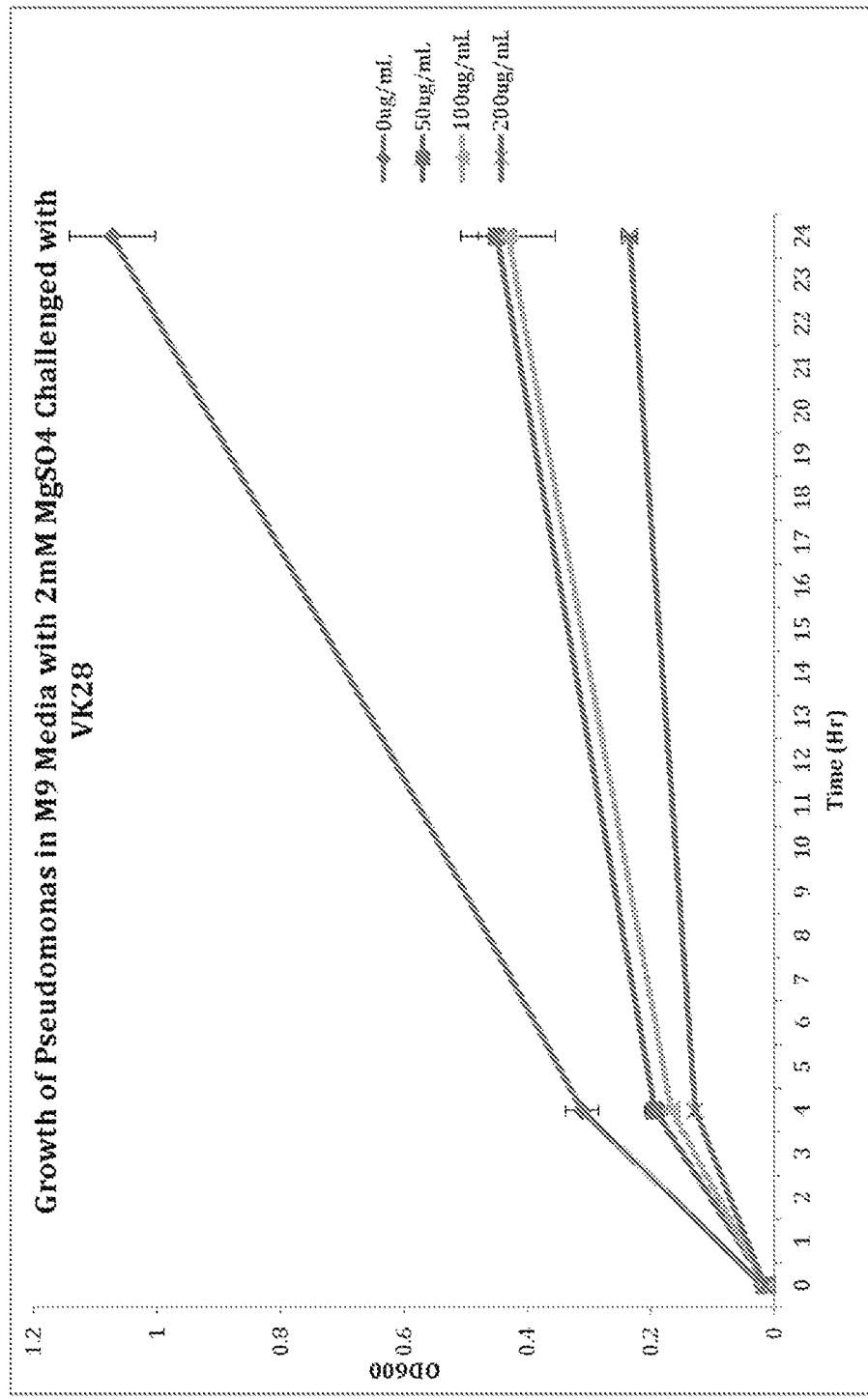
FIG. 20 is a growth curve graph that demonstrates the results of a time-kill assay for treatment of *Pseudomonas aeruginosa* with VK28 in the presence of magnesium.

This example demonstrates VK28 can inhibition growth of $Pseudomonas\ aeruginosa$ in the presence of magnesium. $Pseudomonas\ aeruginosa$ was grown similar to as described in Example 21 in M9 media containing 2 mM $MgSO_4$ for 24 hours in the presence of 0 μg/ml, 50 μg/ml, 100 μg/ml, or 200 μg/ml VK28. The OD$_{600}$ was measured at 0, 4, and 24 hour and the results are shown in the time-kill curves of FIG. 20. The results show that VK28 inhibition of growth of *Pseudomonas aeruginosa* is not reduced in the presence of magnesium.

Example 24

Figure 21:
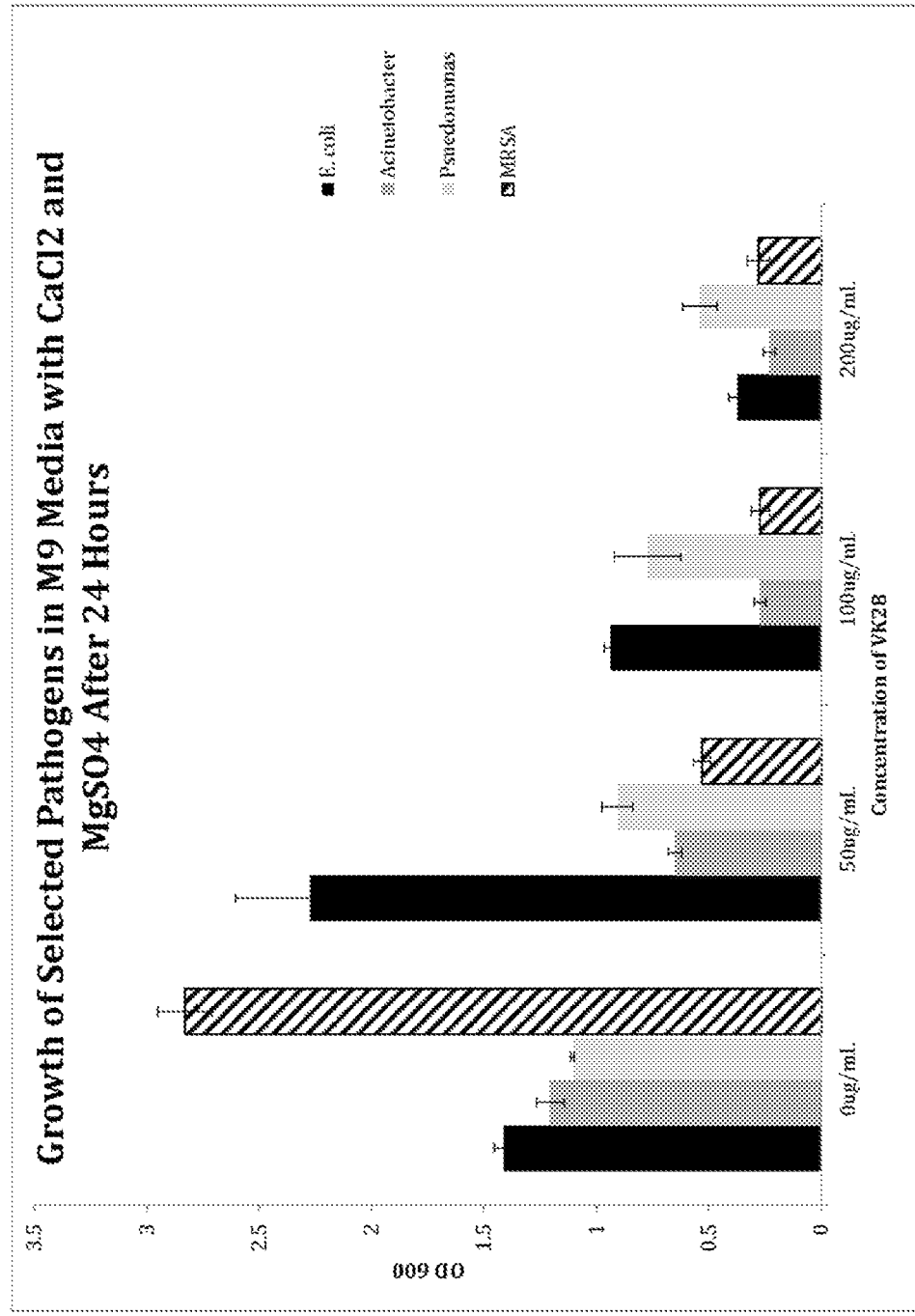
FIG. 21 is a bar graph that demonstrates VK28 inhibition of growth of a number of strains of bacteria in the presence of magnesium and calcium.

This example demonstrates the inhibitory effect of VK28 is not dependent on calcium or magnesium levels for the bacterial strains tested. In this example, strains of MR *Staphylococcus aureus* (MRSA), *Acinetobacter baumannii* (*Acinetobacter*), *Escherichia coli* (*E. coli*), and *Pseudomonas aeruginosa* (*Pseudomonas*) were grown in M9 media in the presence of 2 mM MgSO$_4$ and 1.35 mM CaCl$_2$ for 24 hours in the presence or absence of 0 μg/ml, 50 μg/ml, 100 μg/ml, or 200 μg/ml of VK28. The OD$_{600}$ was measured at 24 hour and the results are shown in the bar graph of FIG. 21. The results show that VK28 inhibition of growth of a number of strains of bacteria is not reduced in the presence of magnesium and calcium.

Example 25

Figure 34:
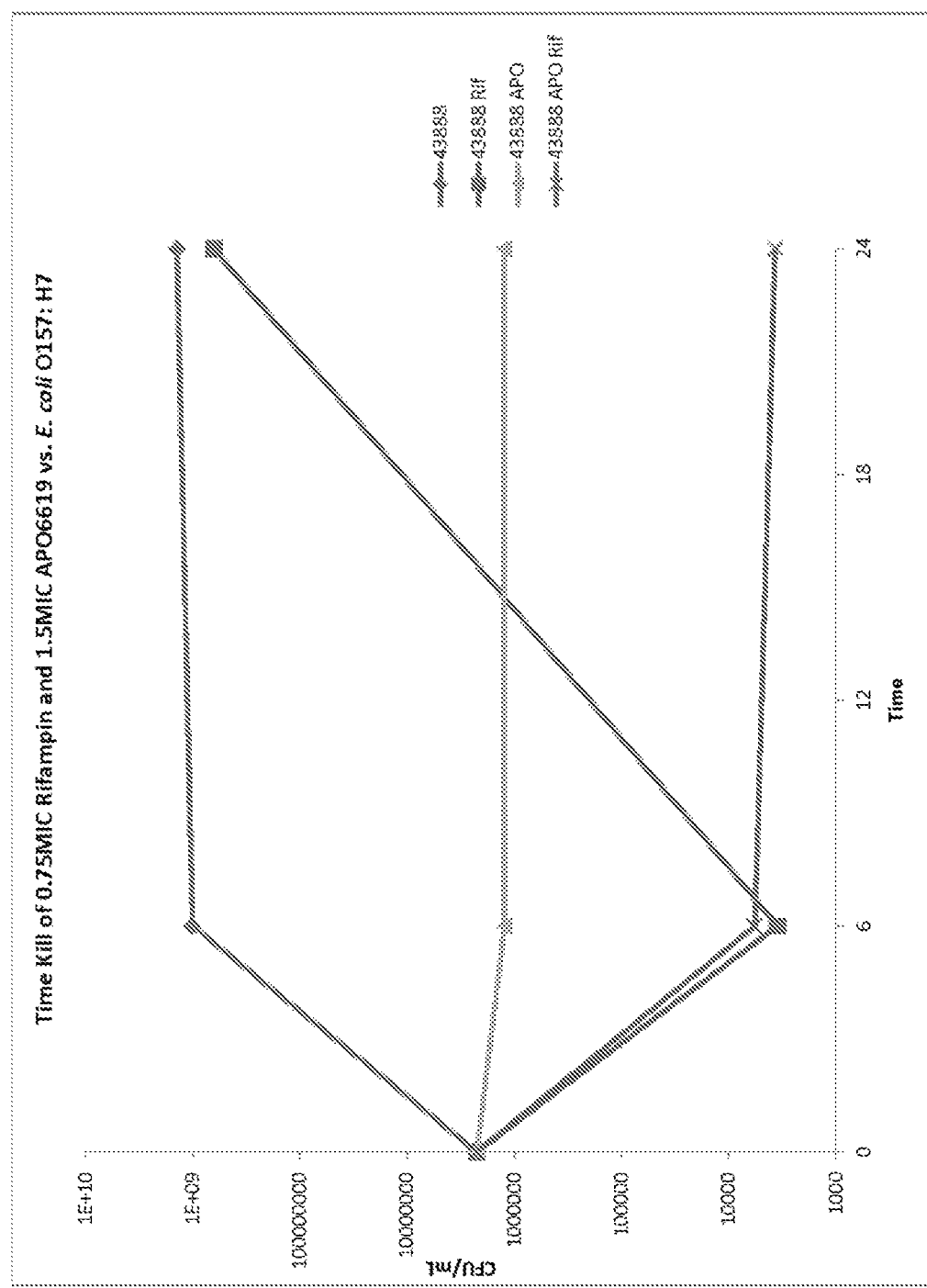
FIG. 34 shows the time kill curves demonstrating that combinational effect of Apo6619 and Rifampin of *E. coli* O157:H7.

In this example, time-kill assays were performed as described in Example 9 using Apo6619 as the iron chelator in combination with Rifampin against *E. coli* O157:H7. The initial inocula was 1×10^6 CFU/mL, and were challenged with 1.5×MIC Apo6619 alone, 0.75×MIC Rifampin alone, or a combination of 1.5×MIC Apo6619 and 0.75×MIC Rifampin. Time-kill results were analyzed by determining the change in log 10 numbers of CFU/mL at 0, 5 and 24 hours. FIG. 34 shows the time kill curves demonstrating that combinational effect of Apo6619 and Rifampin.

Example 26

Figure 35:
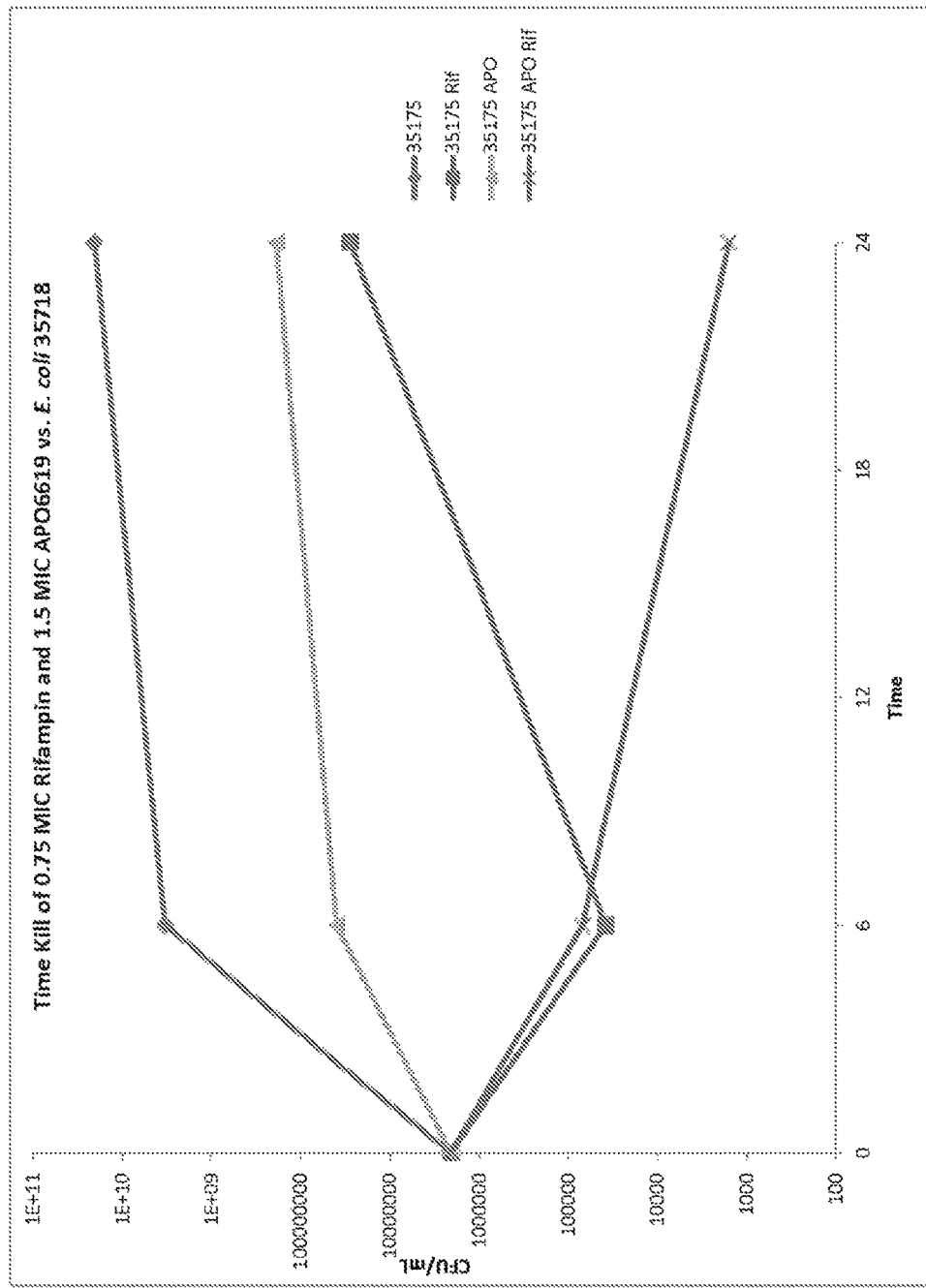
FIG. 35 shows the time kill curves demonstrating that combinational effect of Apo6619 and Rifampin of *E. coli* 35718.

In this example, time-kill assays were performed as described in Example 9 using Apo6619 as the iron chelator in combination with Rifampin against *E. coli* 35718. The initial inocula was 1×10^6 CFU/mL, and were challenged with 1.5×MIC Apo6619 alone, 0.75×MIC Rifampin alone, or a combination of 1.5×MIC Apo6619 and 0.75×MIC Rifampin. Time-kill results were analyzed by determining the change in log 10 numbers of CFU/mL at 0, 5 and 24 hours. FIG. 35 shows the time kill curves demonstrating that combinational effect of Apo6619 and Rifampin.

Example 27

Figure 36:
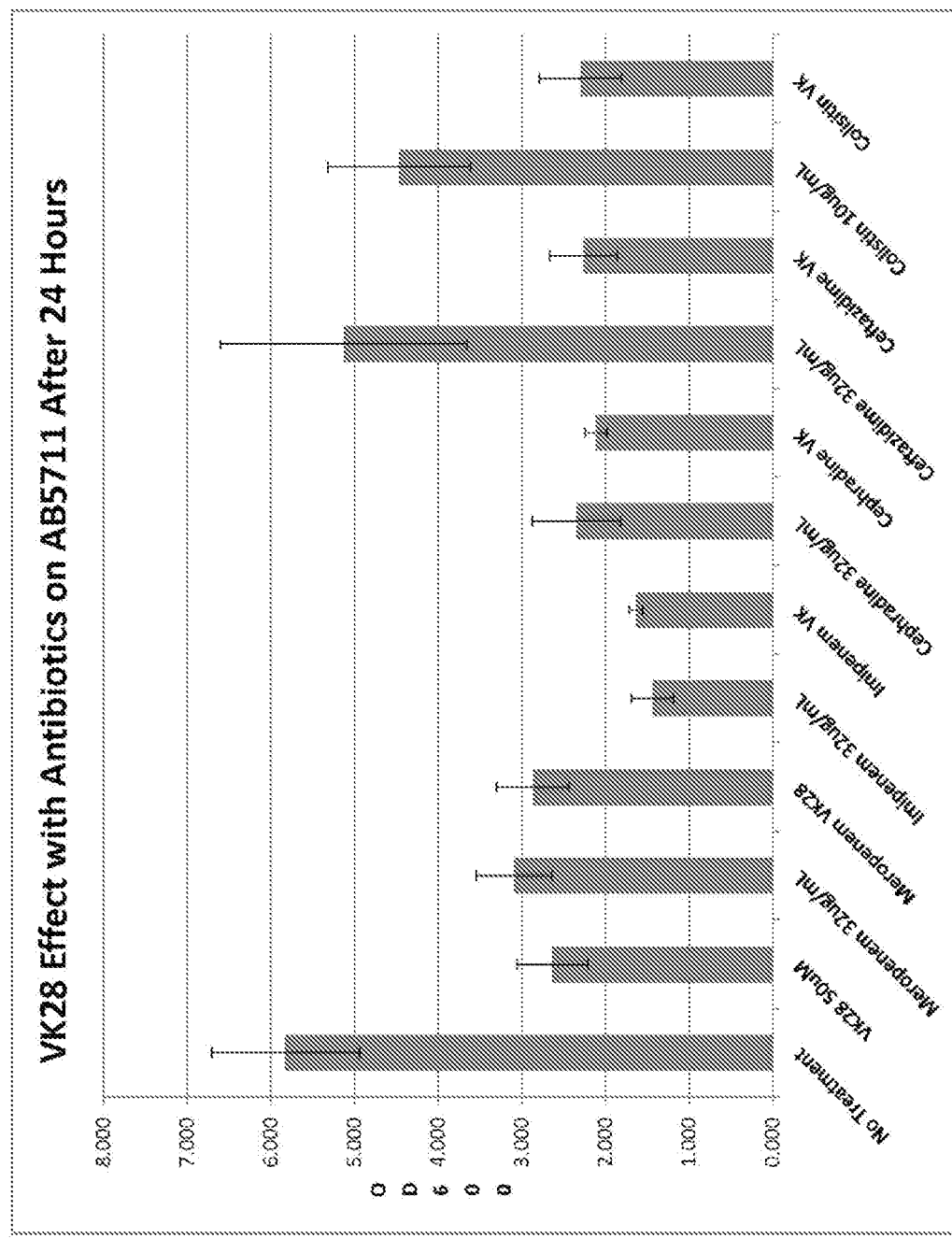
FIG. 36 is a bar graph demonstrating the effects of iron chelator VK28 on the activity of antibiotics.
Figure 37:
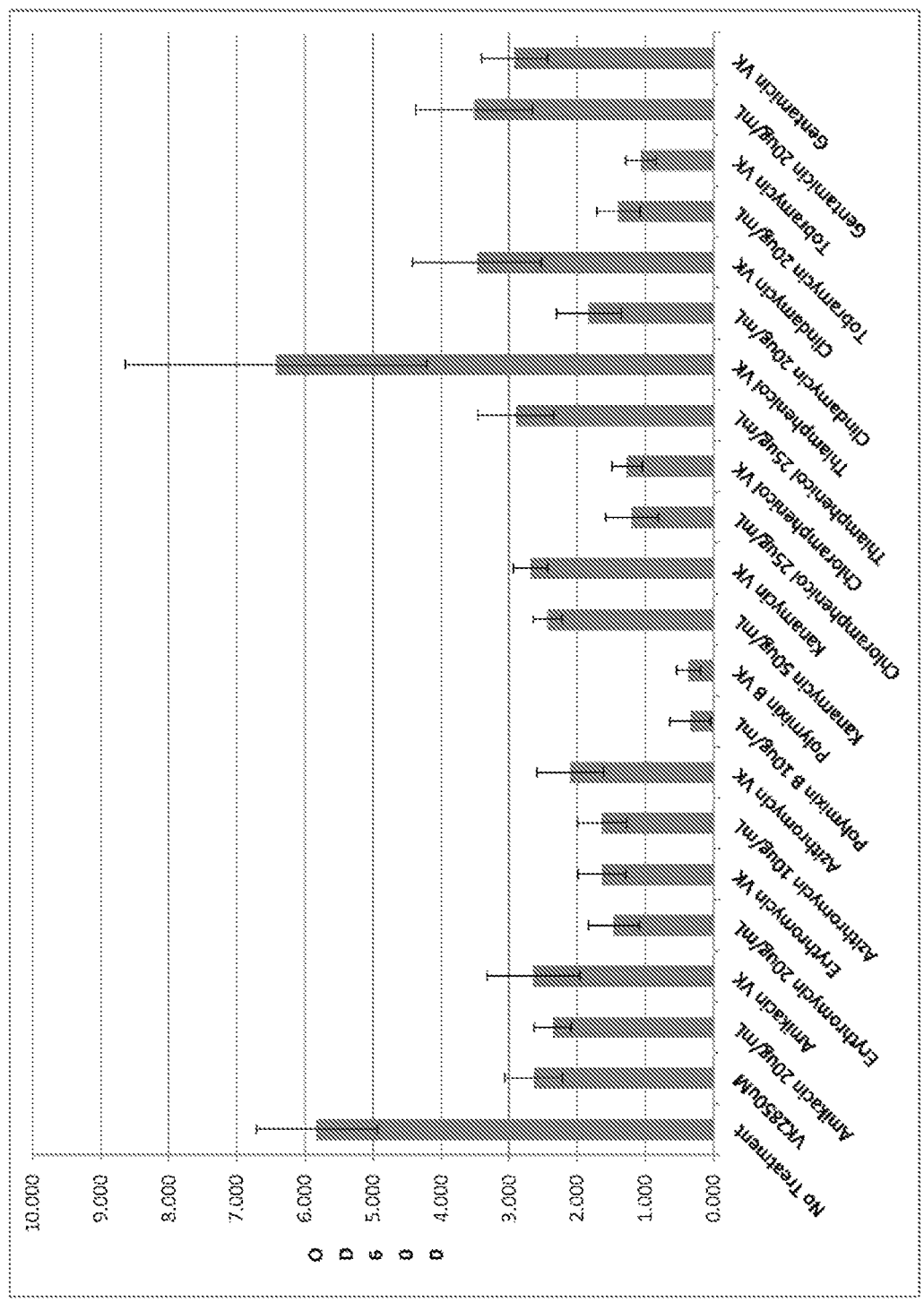
FIG. 37 is a bar graph demonstrating the effects of iron chelator VK28 on the activity of antibiotics.

In this example, culture of AB5711 was grown overnight in LB media at 37° C. and diluted 1:100 into Media A. Cells were allowed to grow for 4 hours at 37 in 96-well plates and were then treated with antibiotics with or without 50 μM VK28. Cells were then allowed to shake for an additional 20 hours, and OD600 measurements were taken. FIGS. 36 and 37 demonstrates the results of these experiments. The iron chelator VK28 was not shown to inhibit the activity of the antibiotics with the exception of Thiaphenicol.

Example 28

Synthesis of 5-(2-(4-(2-hydroxyethyl)piperazin-1-yl) ethyl)-8-quinolinol dihydrochloride (Herein Designated as Compound 4 Dihydrochloride)

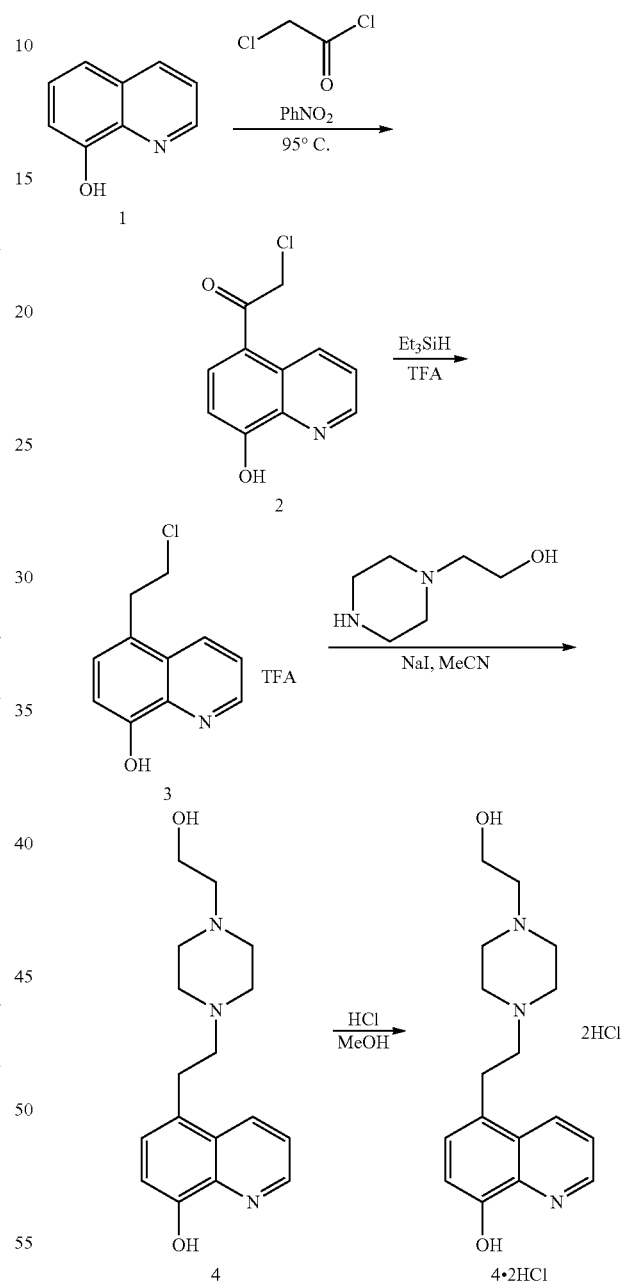

To a stirred solution of quinolin-8-ol (compound 1; 97 g, 0.669 mol, 1 eq.) in nitrobenzene (toxic and carcinogenic) was added chloro acetyl chloride (55.8 mL, 0.701 mol, 1.05 eq.) at 0° C. under argon, forming a yellow suspension. AlCl$_3$ (160 g, 1.2 mol, 1.79 eq.) was added portion wise and the suspension became clear upon stirring. The reaction mixture was heated to 100° C. for 36 hours. The reaction mixture was cooled down to room temperature and poured to mixture of HCl (450 mL, 6 N), ice (600 g) and methyl t-butyl ether (MTBE, 800 mL). The yellow precipitate was filtered via a filter paper, washed with MTBE (~500 mL) and dried. The precipitate was digested to break up the aluminum complex with 200 mL of 12 N HCl at room temperature for 3 days, filtered and washed with ethyl acetate (EA). The resulting solid salt was stirred with 10% NaOAc aqueous solution (enough to make pH=6, ~2 L used) to give a greenish suspension. The green precipitate was collected, dissolved in 1.8 L dichloromethane and dried over $MgSO_4$ anhydrous. Upon condensation, a yellow solid precipitated out, and the solution size was reduced to 500 mL. The yellow solid was filtered and washed with MTBE once and dried providing 58.5 g (38.5%) of compound 2 as a yellow solid.

Under argon protection, to a three neck round bottom flask containing compound 2 (58 g, 0.26 mol, 1 eq.) and chilled to 5° C. was added trifluoroacetic acid (TFA, 500 mL) followed by addition of triethylsilane (244 g, 2.1 mol, 8 eq.). The reaction was warmed to room temperature and heated to 60° C. overnight (16 hours). The mixture was cooled down to room temperature. The volatiles were first evaporated on rotary evaporator, and later using high vacuum at 30-40° C. The clear oil was decanted from the dark product residue and triturated with ether. The precipitated solid was filtered, rinsed with ether, and dried to provide 70 g (83.8%) of compound 3 as a yellow solid.

To a suspension of compound 3 (20 g, 62 mmol, 1 eq.) in anhydrous acetonitrile (200 mL) was added NaI (9.3 g, 62 mmol, 1 eq.) and 2-piperazin-1-yl-ethanol (140.4 g, 310 mmol, 5 eq.). The mixture was heated to 100° C. overnight (20 h) in a sealed reaction tube. The reaction mixture was cooled down to room temperature and the volatiles were evaporated. The residue was diluted with 500 mL water and extracted with dichloromethane (DCM) three times. The organic layer was washed with water, brine and dried over sodium sulfate anhydrous. The DCM solution was condensed to a crude brown solid. The resulting solid was dissolved in EA and triturated with hexanes to give 8.6 g (46%) of compound 4 as a yellow solid. Compound 4 (8.35 g, 27.7 mmol, 1 eq.) was dissolved in methanol (200 mL) and HCl in ether (27.7 mL, 55.4 mmol, 2 eq.) was added. The mixture was stirred at room temperature overnight (16 h), and a yellow suspension was formed. To the reaction mixture was added ether (400 mL) under vigorous stirring. The yellow precipitate was collected and freeze dried to afford 10.3 g (99%) of the final compound 4.2HCl salt as a light yellow solid.

Example 29

Figure 40:
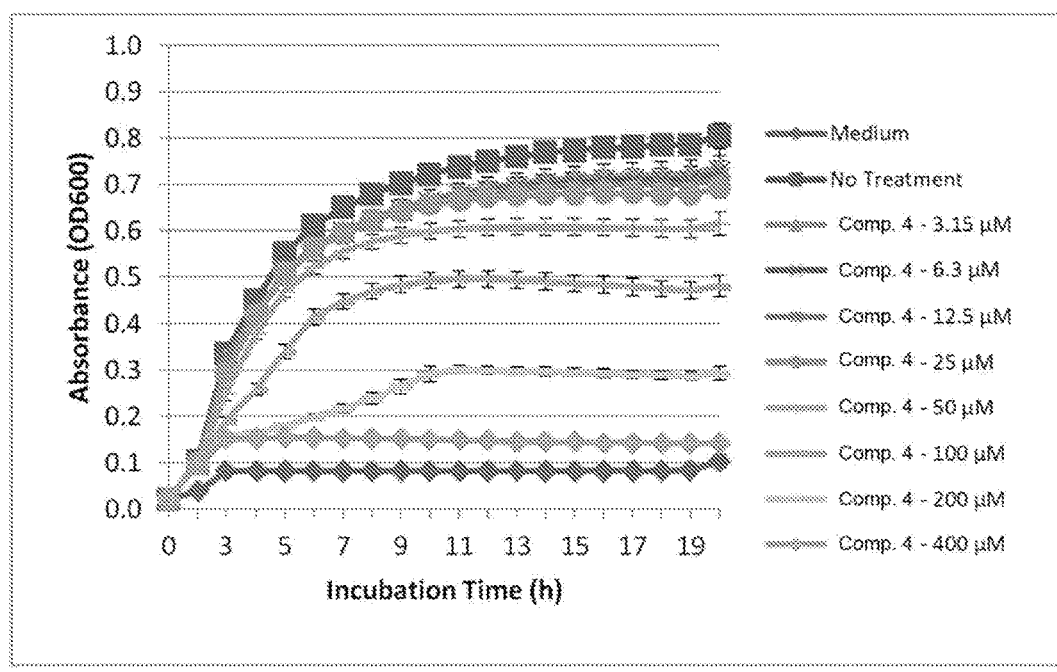
FIG. 40 is a graph depicting the growth curves of *A. baumannii* cultures in the presence of compound 4

The VK-28 derivative compound 4, which is highly stable in aqueous solution, has shown an antibacterial activity against *A. baumannii*, see FIG. 40. For example, in growth curves of *A. baumannii*, strain AB5711 in cationic—adjusted Mueller-Hinton Broth (CAMHB) media $OD_{600}$ was dramatically reduced by the presence of compound 4, FIG. 40. It should be noted that the inhibition occurred in a dose-responsive manner.

Example 30

Figure 41:
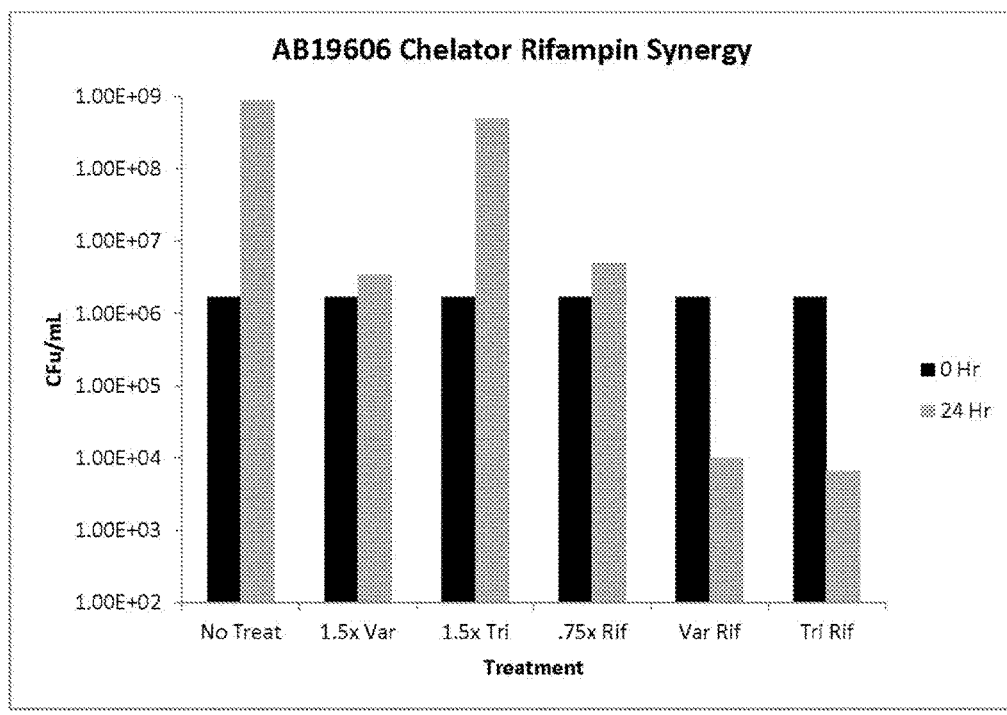
FIG. 41 is a bar graph depicting the growth of *A. baumannii* strain AB19606 in the presence of 1.5×MIC compound 4 (Var) or 1.5×MIC Triapine (Tri) with or without 0.75×MIC Rifampin (Rif).

This example shows that Compound 4 and Triapine work in synergy with Rifampin against *A. baumannii* strain AB19606. *A. baumannii* strain AB19606 was grown in CAMHB and challenged with 1.5×MIC compound 4 (Var) or 1.5×MIC Triapine (Tri) with or without 0.75×MIC Rifampin (Rif). Growth was estimated by absorbance at 600 nm (y-axis) at 0 or 24 hours. FIG. 41 shows the results. The administration of Rifampin, compound 4 or Triapine alone resulted in no reduction of bacteria, while the addition of either compound 4 or Triapine in combination with Rifampin (Var Rif or Tri Rif, respectively) resulted in a significant reduction in bacteria, suggesting that compound 4 in combination with Rifampin worked synergistically in preventing *A. baumannii* bacterial growth and that triapine in combination with Rifampin worked synergistically in preventing *A. baumannii* bacterial growth.

Example 31

Figure 42:
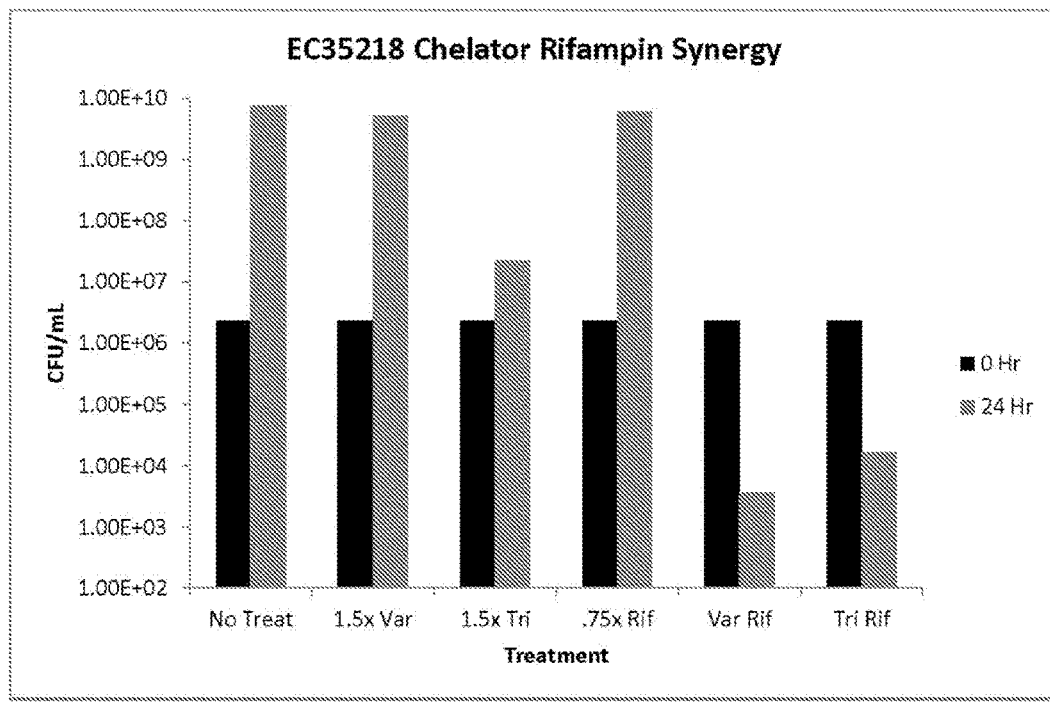
FIG. 42 is a bar graph depicting the growth of *E. coli* EC35718 in the presence of 0.5×MIC compound 4 (Var) or 1.5×MIC Triapine (Tri) with or without 0.75×MIC Rifampin (Rif).

This example shows that Compound 4 and Triapine work in synergy with Rifampin against *E. coli* strain EC35218. *E. coli* strain EC35218 was grown in CAMHB and challenged with 1.5×MIC compound 4 (Var) or 1.5×MIC Triapine (Tri) with or without 0.75×MIC Rifampin (Rif). Growth was estimated by absorbance at 600 nm (y-axis) at 0 or 24 hours. FIG. 42 shows the results. The administration of Rifampin, compound 4 or Triapine alone did not result in a reduction of bacteria, while the addition of either compound 4 or Triapine in combination with Rifampin (Var Rif or Tri Rif, respectively) resulted in a significant reduction in bacteria, suggesting they work synergistically in preventing *E. coli* bacterial growth.

Example 32

This example demonstrates that the addition of an iron chelator to antibiotic treatment of a bacterial strain inhibits the formation of antibiotic-resistant strains. Cultures of AB5075, a stain of *A. baumannii* (Ab), was cultured in the presence of Rifampin alone, the iron chelator ApoL1 alone or Rifampin combination with ApoL1 for 7 days. $OD_{600}$ was measured at days 0, 1, 2, and 7 and the time-kill graphs are shown in FIG. 43. FIG. 43 demonstrates without the addition of an ApoL1, antibiotic-resistant strains of Ab develop in less than one day in the presence of rifampin alone. Unexpectantly, the addition of ApoL1 to treatment with Rifampin results in the inhibition of rifampin-resistant strains of Ab over the 7 days.

While particular embodiments of the present invention have been shown and described, it will be obvious to those skilled in the art that changes and modifications may be made without departing from the true spirit and scope of this invention. Other embodiments and uses of the invention will be apparent to those skilled in the art from consideration of the specification and practice of the invention disclosed herein. All references cited herein, including all publications, U.S. and foreign patents and patent applications are specifically and entirely incorporated by reference. It is intended that the specification and examples be considered exemplary only with the true scope and spirit of the invention indicated by the following claims. The use of the singular includes the plural unless the context indicates otherwise. Furthermore, the term "comprising of" includes the terms "consisting of" and "consisting essentially of."

REFERENCES

S. Yeoh-Ellerton, M. C. Stacey, "Iron and 8-Isoprostane Levels in Acute and Chronic Wounds," *The Journal of Investigative Dermatology*, Vol. 121, No. 4, pp. 918-925 (2003), D. W. Reid, C. O'May, S. M. Kirov, L. Roddam, I. L. Lamont, K. Sanderson, "Iron chelation directed against biofilms as an adjunct to conventional antibiotics," *Am. J. Physiol. Lung Cell Mol. Physiol.*, Vol. 296: 857-858 (2009)—doi: 10.1152/ajplung.00058.2009, D. B. Shachar, N. Kahana, V. Kampel, A. Warshawsky, M. B. Youdim, "Neuroprotection by a novel brain permeable iron chelator, VK-28, against 6-hydroxydopamine lesion in rats," *Neuropharmacology*, 2004 February; 46(2):254-63, abstract found 25 Jan. 2011 on-line at http://www.ncbi.nlm.nih.gov/pubmed/14680763.

U.S. Pat. No. 7,446,089 (Singh et al.), "Methods of Inhibiting and Treating Bacterial Biofilms by Metal Chelators," issued 4 Nov. 2008, All patents, publications and other references, and the teachings set forth therein, which cited throughout this application are incorporated herein by reference in their entirety.

I claim:

1. A method for treating a bacterial infection, wherein said method comprises administering an effective amount of 5-((4-(2-hydroxylethyl)piperazin-1-yl)methyl)-8-hydroxyquinoline (VK28), or pharmaceutically acceptable salt thereof, to a patient in need of treatment for said bacterial infection, further comprising administering an effective amount of an antibiotic to the patient, wherein the said antibiotic is colistin or tetracycline and wherein the bacterial infection is caused by *Acinetobacter baumannii*.

2. The method of claim 1, wherein said bacterial infection is in a wound.

3. The method of claim 1, wherein said method comprises administering to the patient before or after surgery.

4. The method of claim 1, wherein the patient is identified as having a heightened risk of a bacterial infection.

5. The method of claim 1, wherein the antibiotic is: tetracycline or a pharmaceutically acceptable salt thereof.

6. A method of treating patient infected with drug-resistant bacteria, the method comprising the steps of: determining whether the patient is infected by bacteria having resistance to one or more antibiotics; administering an effective amount of 5-((4-(2-hydroxylethyl)piperazin-1-yl)methyl)-8-hydroxyquinoline (VK28), or pharmaceutically acceptable salt thereof, to a patient; and administering to the patient an antibiotic to which the bacteria has resistance, wherein the said antibiotic is colistin or tetracycline and wherein the bacterial infection is caused by *Acinetobacter baumannii*.

7. A method for treating bacterial infection, wherein said method comprises administering an effective amount of 5-((4-(2-hydroxylethyl)piperazin-1-yl)methyl)-8-hydroxyquinoline (VK28), or pharmaceutically acceptable salt thereof, to a patient in need of treatment for said bacterial infection, further comprising administering an effective amount of an antibiotic to the patient; wherein the antibiotic is tetracycline and wherein the bacterial infection is caused by *Acinetobacter baumannii*.

8. The method of claim 7, wherein said bacterial infection is in a wound.

9. The method of claim 7, wherein said method comprises administering to the patient before or after surgery.

* * * * *